(12) United States Patent
Zheng et al.

(10) Patent No.: US 12,246,267 B2
(45) Date of Patent: Mar. 11, 2025

(54) METHOD OF CAPTURING AND/OR PURIFYING A TARGET

(71) Applicant: Agency for Science, Technology and Research, Singapore (SG)

(72) Inventors: Zi Ying Zheng, Singapore (SG); Wei Zhang, Singapore (SG)

(73) Assignee: Agency For Science, Technology and Research, Singapore (SG)

( * ) Notice: Subject to any disclaimer, the term of this patent is extended or adjusted under 35 U.S.C. 154(b) by 527 days.

(21) Appl. No.: 17/440,374

(22) PCT Filed: Mar. 20, 2020

(86) PCT No.: PCT/SG2020/050150
§ 371 (c)(1),
(2) Date: Sep. 17, 2021

(87) PCT Pub. No.: WO2020/190216
PCT Pub. Date: Sep. 24, 2020

(65) Prior Publication Data
US 2022/0184526 A1    Jun. 16, 2022

(30) Foreign Application Priority Data
Mar. 21, 2019  (SG) .......................... 10201902549Y

(51) Int. Cl.
*B01D 15/18*    (2006.01)
*B01D 15/36*    (2006.01)
(Continued)

(52) U.S. Cl.
CPC ....... *B01D 15/1864* (2013.01); *B01D 15/363* (2013.01); *B01D 15/3804* (2013.01); *C07K 1/36* (2013.01); *G01N 30/20* (2013.01)

(58) Field of Classification Search
CPC ....... B01D 15/1864; C07K 1/36; G01N 30/46
See application file for complete search history.

(56) References Cited

U.S. PATENT DOCUMENTS

| 6,344,172 B1 | 2/2002 | Afeyan et al. |
| 2017/0010243 A1 | 1/2017 | Gaita et al. |
| 2019/0072464 A1 | 3/2019 | Wiederin et al. |

FOREIGN PATENT DOCUMENTS

| CN | 103189390 A | 7/2013 |
| CN | 109030686 A | 12/2018 |

(Continued)

OTHER PUBLICATIONS

Yoshimoto, Noriko, et al. "Salt tolerant chromatography provides salt tolerance and a better selectivity for protein monomer separations." Biotechnology Journal 10.12 (2015): 1929-1934. (Year: 2015).*

(Continued)

*Primary Examiner* — Bradley R Spies
(74) *Attorney, Agent, or Firm* — Hamilton, Brook, Smith & Reynolds, P.C.

(57) ABSTRACT

There is provided a chromatography system comprising a first valve in fluid connection to a first chromatography column and/or a second valve; the second valve in fluid connection to a second chromatography column and the first valve; wherein the first valve and the second valve are operable to provide: a mode that selectively allows a fluid to flow from the first chromatography column to the second chromatography column; and one or more modes that selectively allows the fluid to bypass the first chromatography column and/or the second chromatography column. Also disclosed is a method of capturing and/or purifying a target from a sample thereof. In one embodiment, an acidic protein, alpha-1 anti-trypsin (A1AT), is purified by a tandem column configuration using anion exchange chromatography, whereby a first chromatography column is added in between the sample pump and an injection valve, or replaced the sample loop of AKTA system.

18 Claims, 25 Drawing Sheets

(51) Int. Cl.
    *B01D 15/38*    (2006.01)
    *C07K 1/36*     (2006.01)
    *G01N 30/20*    (2006.01)

(56) References Cited

FOREIGN PATENT DOCUMENTS

| WO | 2015/094094 A1 | 6/2015 | | |
|---|---|---|---|---|
| WO | 2015/121425 A1 | 8/2015 | | |
| WO | WO-2015135884 A1 | * | 9/2015 | .............. B01J 39/26 |
| WO | 2015144481 A1 | 10/2015 | | |

OTHER PUBLICATIONS

European Supplementary Search Report for EP Application No. 20 77 4389, "A Method of Capturing and/or Purifying a Target", date of completion: Oct. 26, 2022, 10 pages.

Notification of Transmittal of the International Search Report and the Written Opinion of the International Searching Authority, or the Declaration for International Application No. PCT/SG2020/050150, "A Method of Capturing and/or Purifying a Target", date of mailing: Sep. 8, 2020.

* cited by examiner

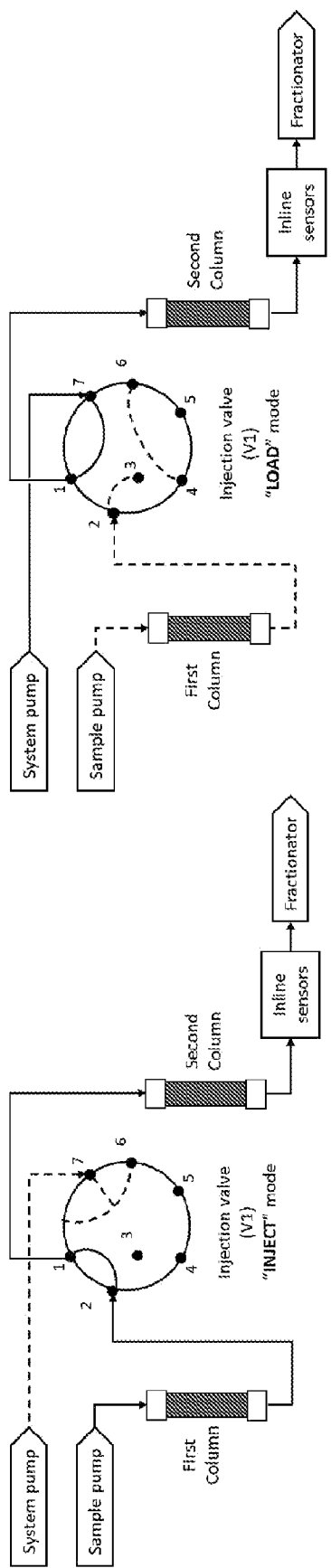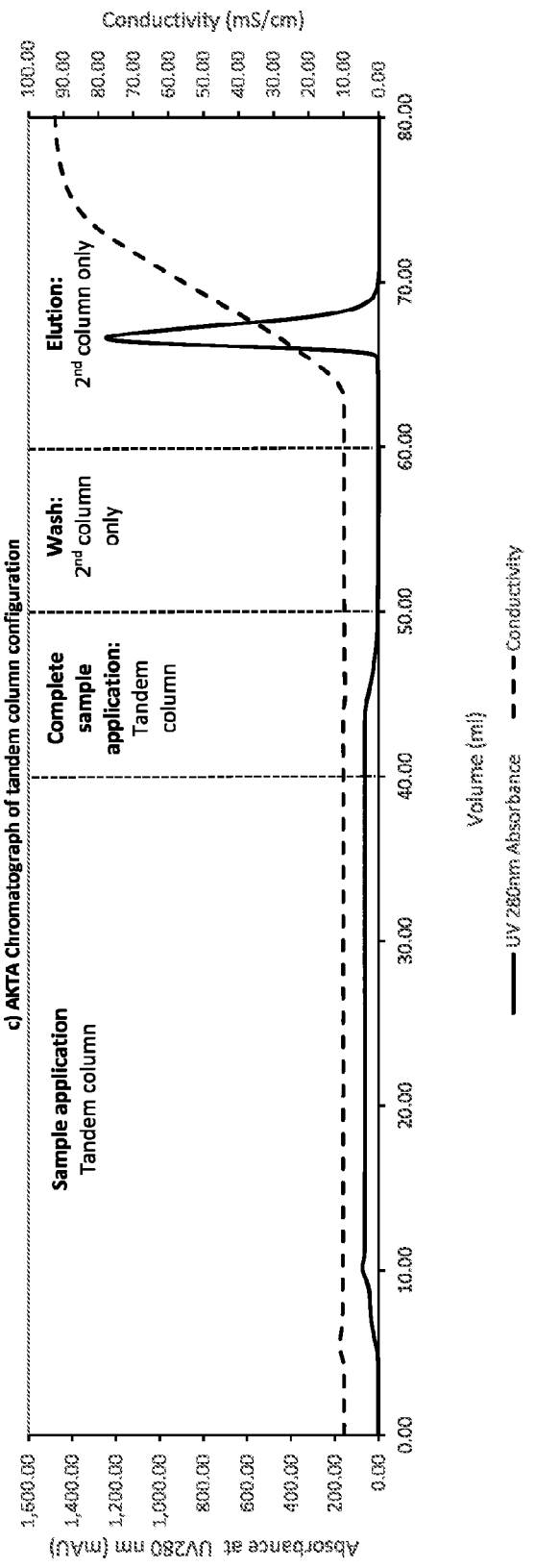
FIG. 2

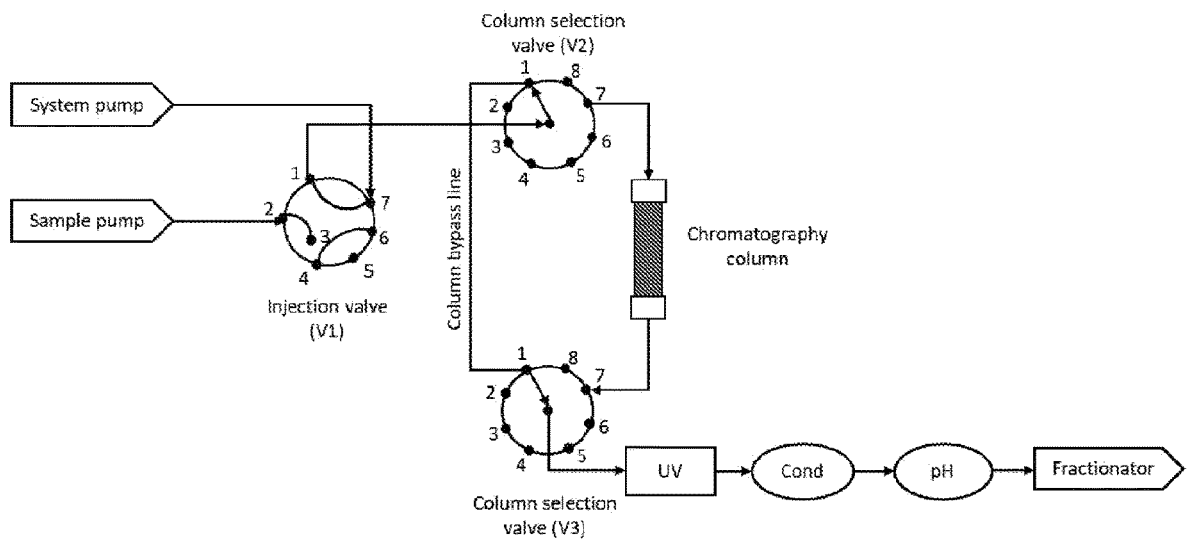
FIG. 3.1
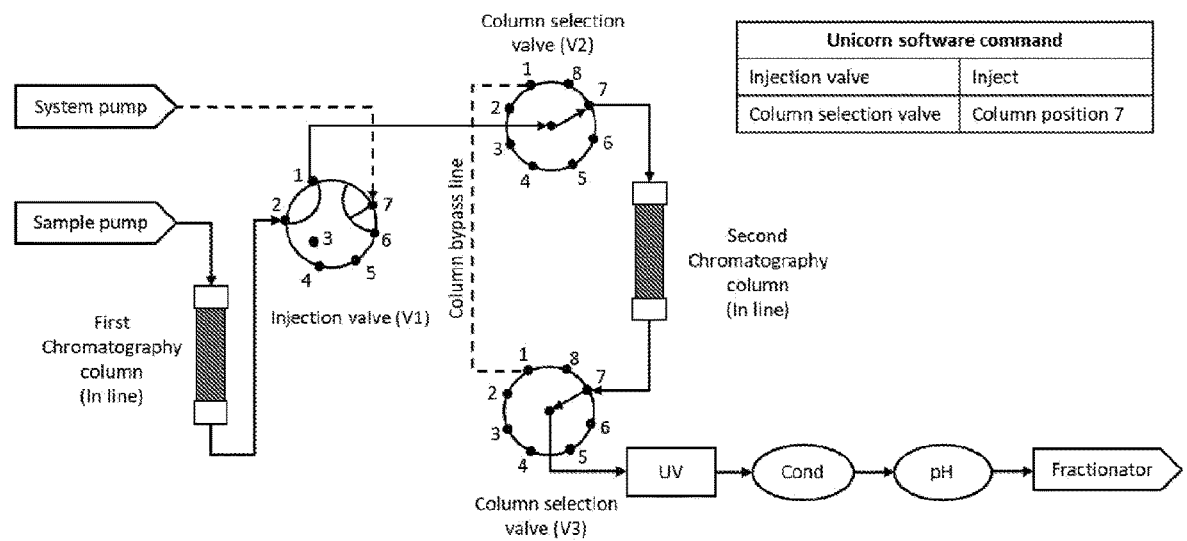
FIG. 3.2

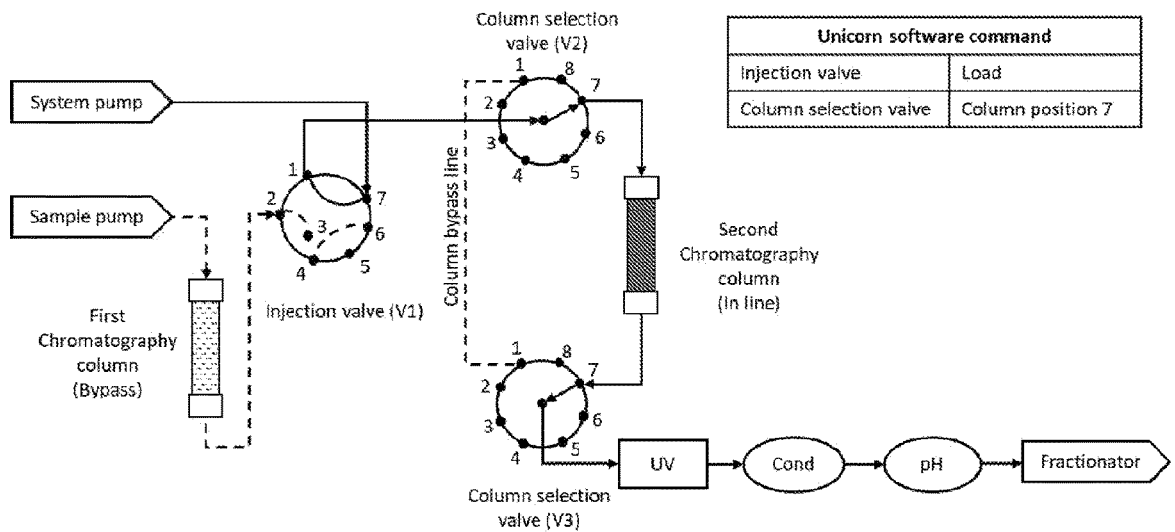
FIG. 3.3
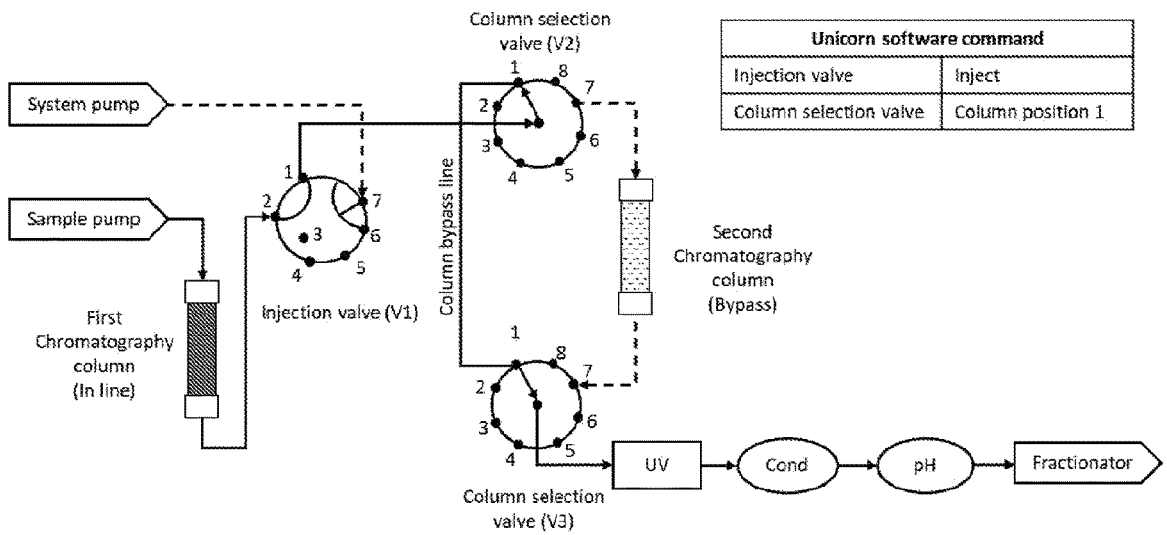
FIG. 3.4

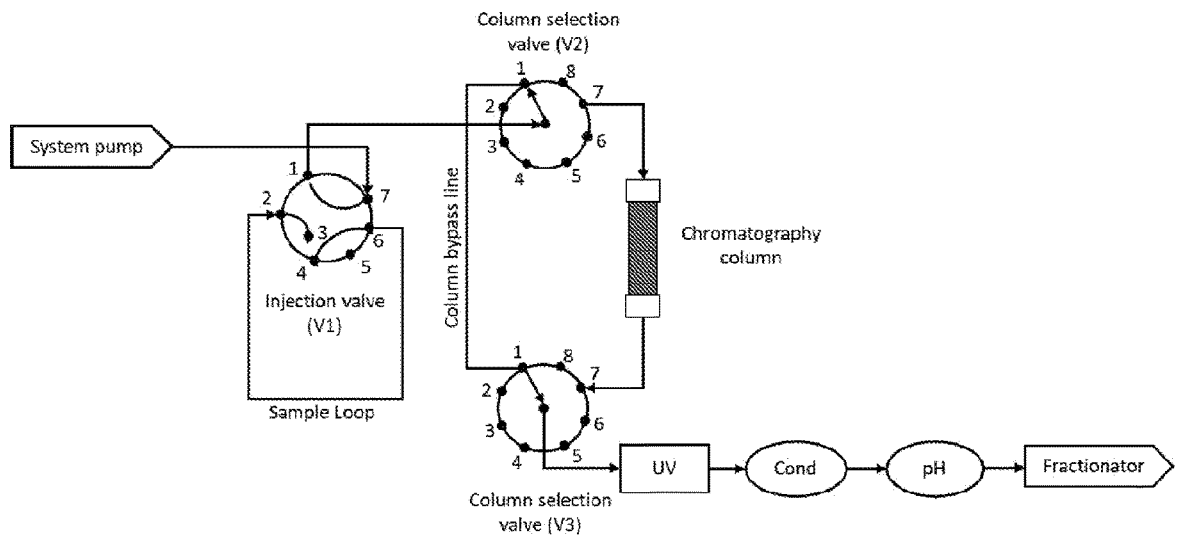
FIG. 4.1
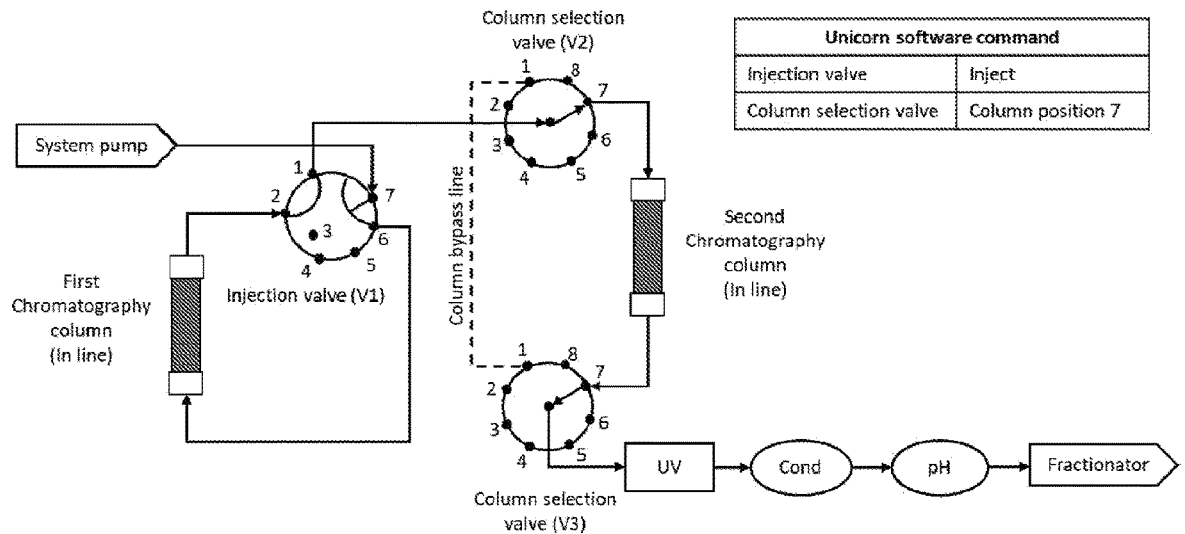
FIG. 4.2

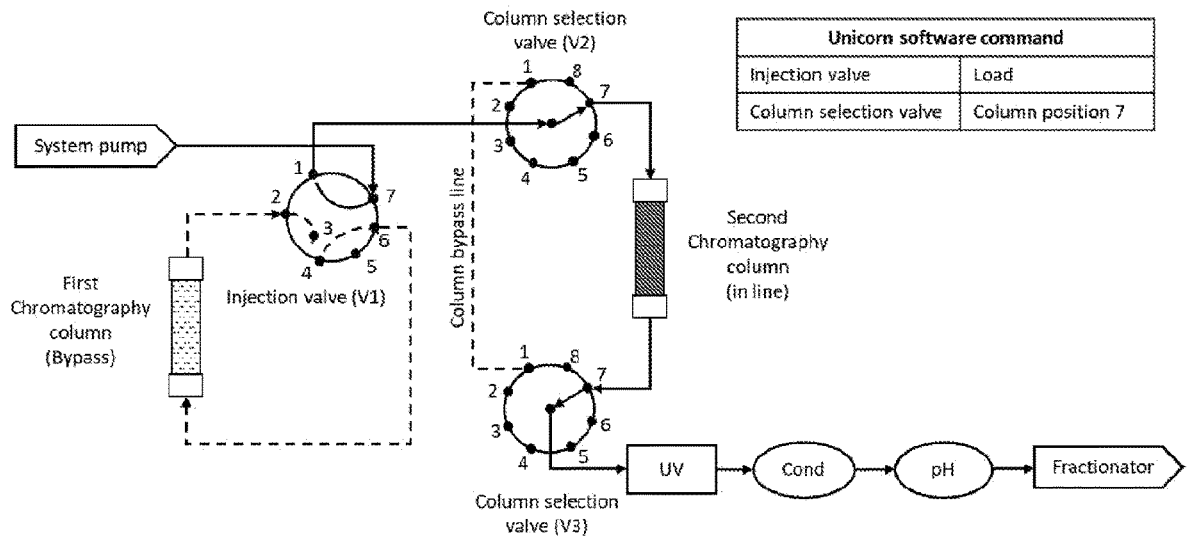
FIG. 4.3
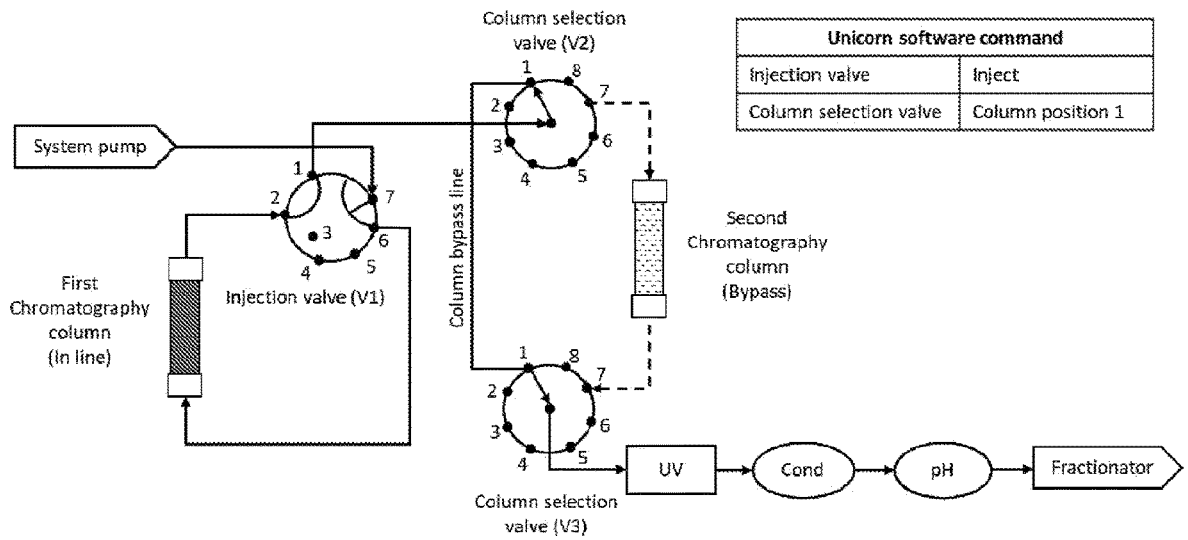
FIG. 4.4

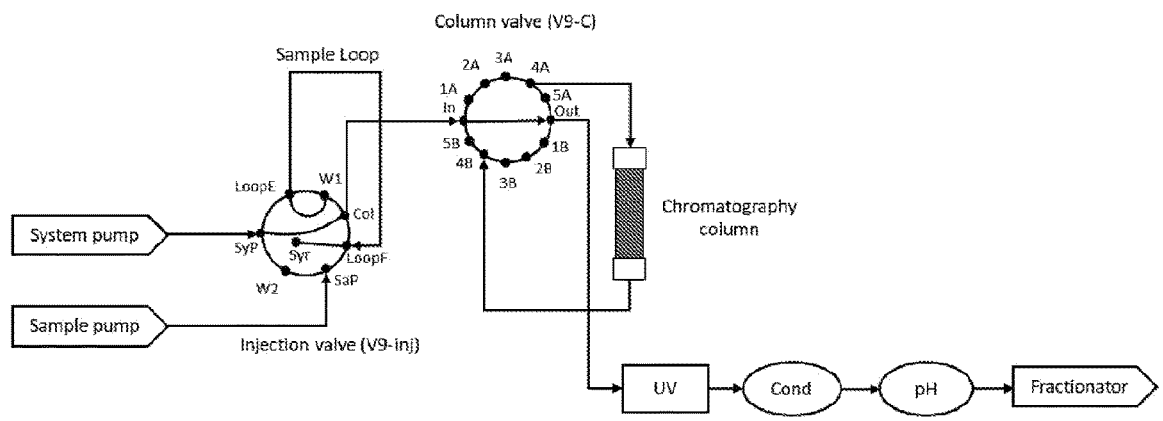
FIG. 5.1
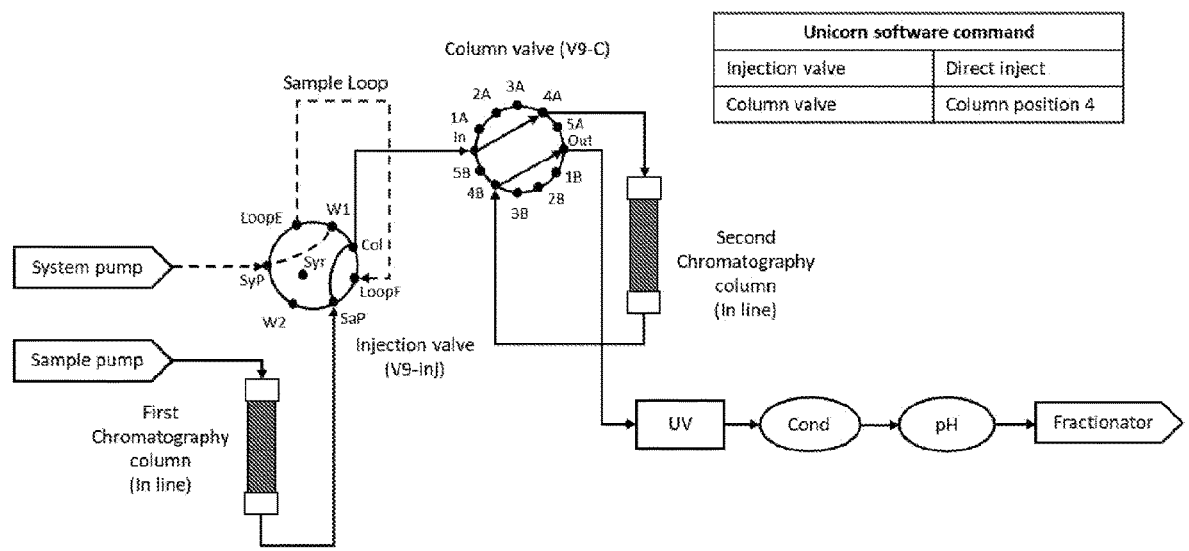
FIG. 5.2

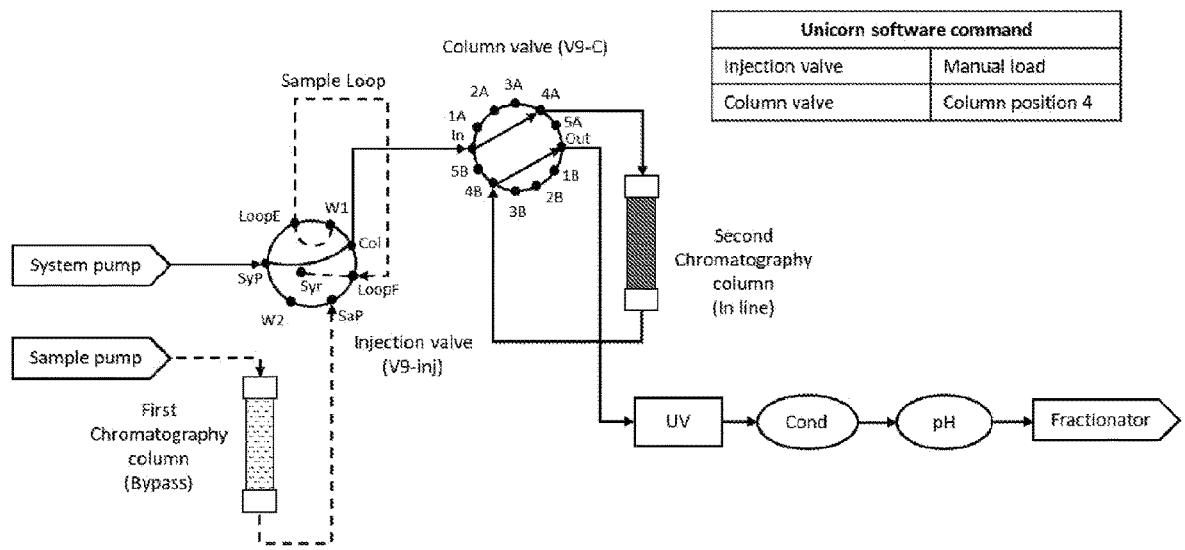
FIG. 5.3
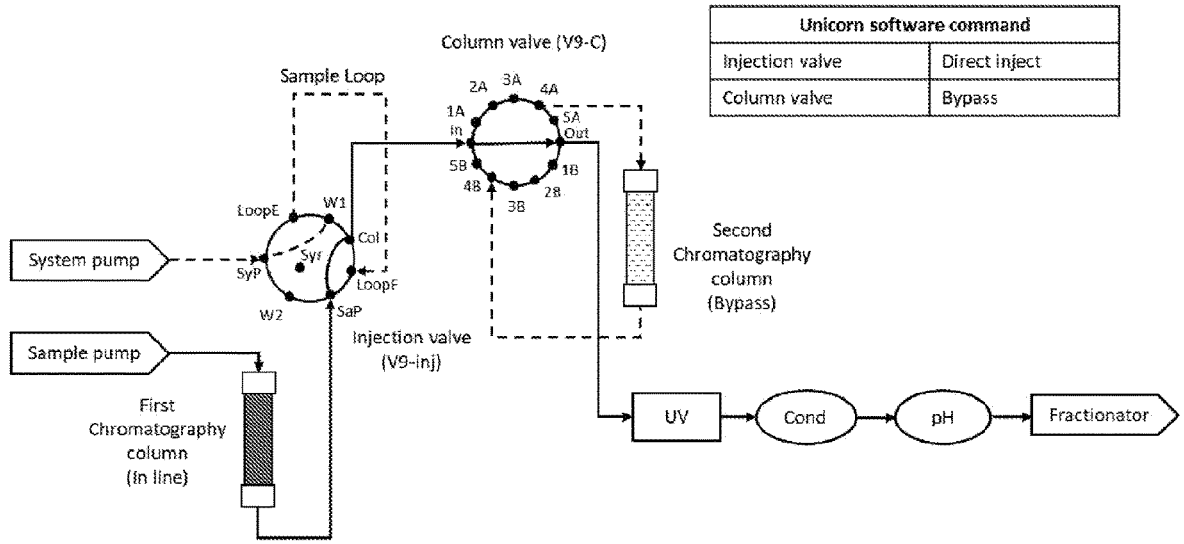
FIG. 5.4

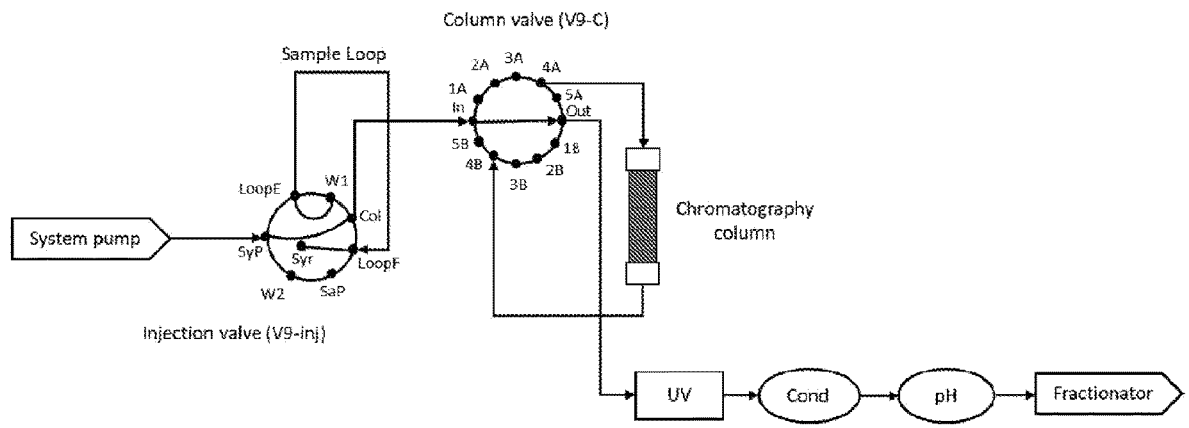
FIG. 6.1
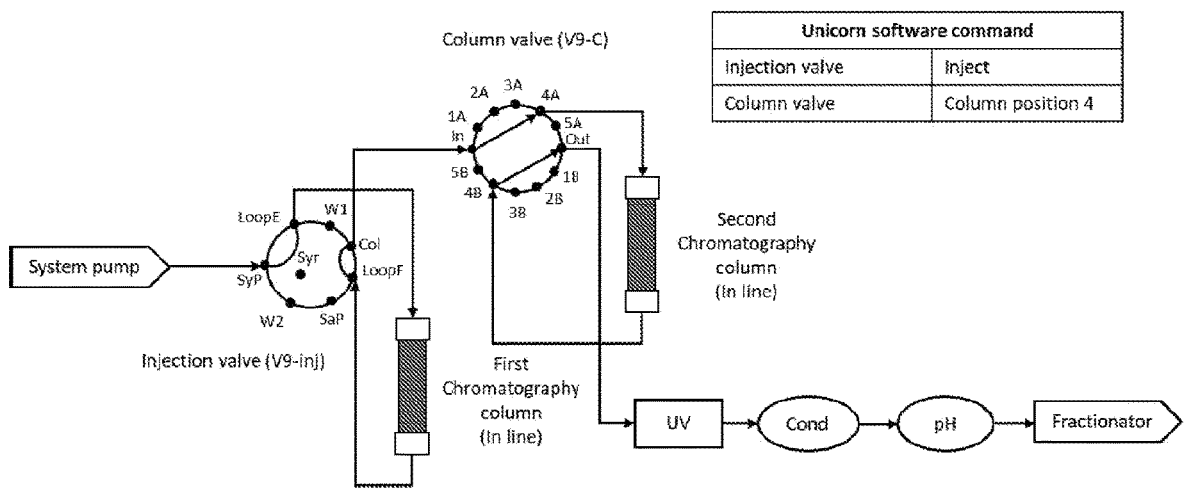
FIG. 6.2

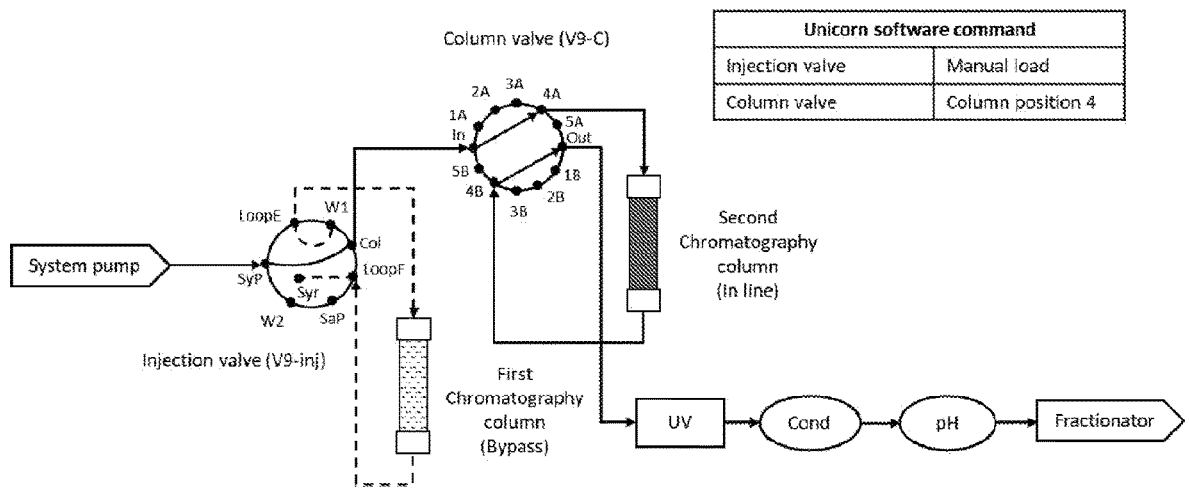
FIG. 6.3
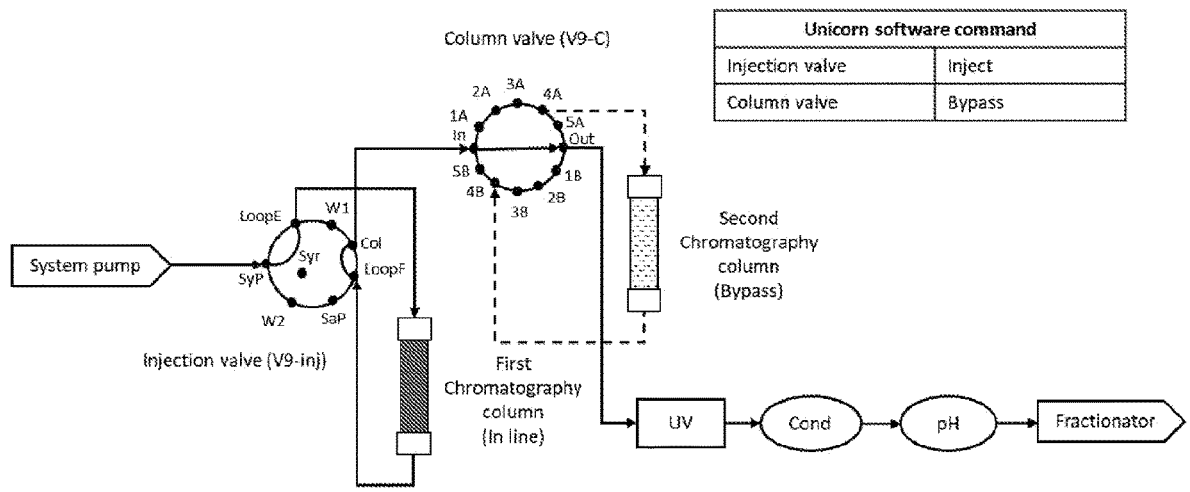
FIG. 6.4

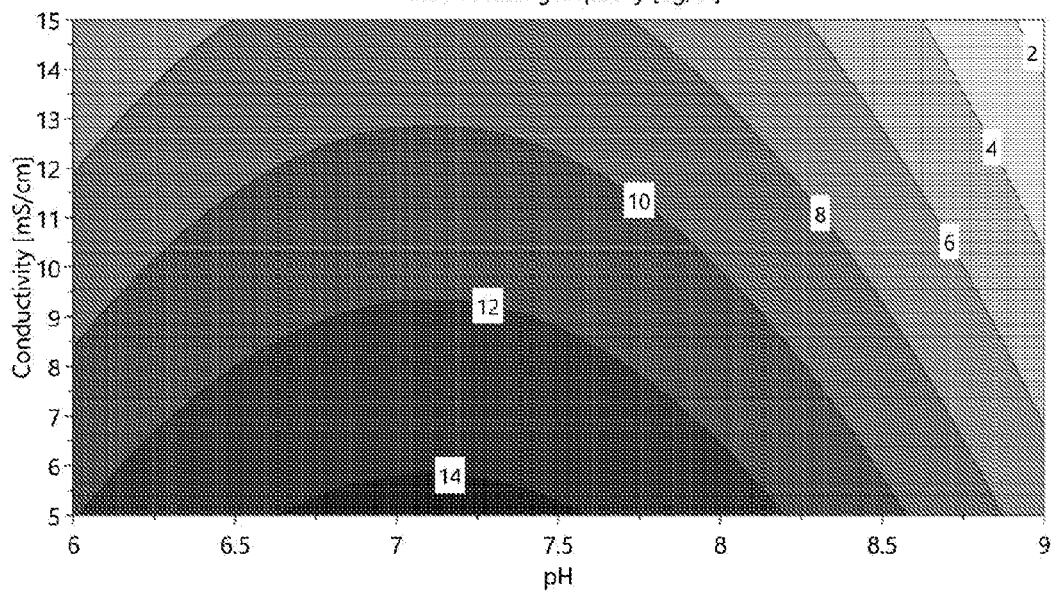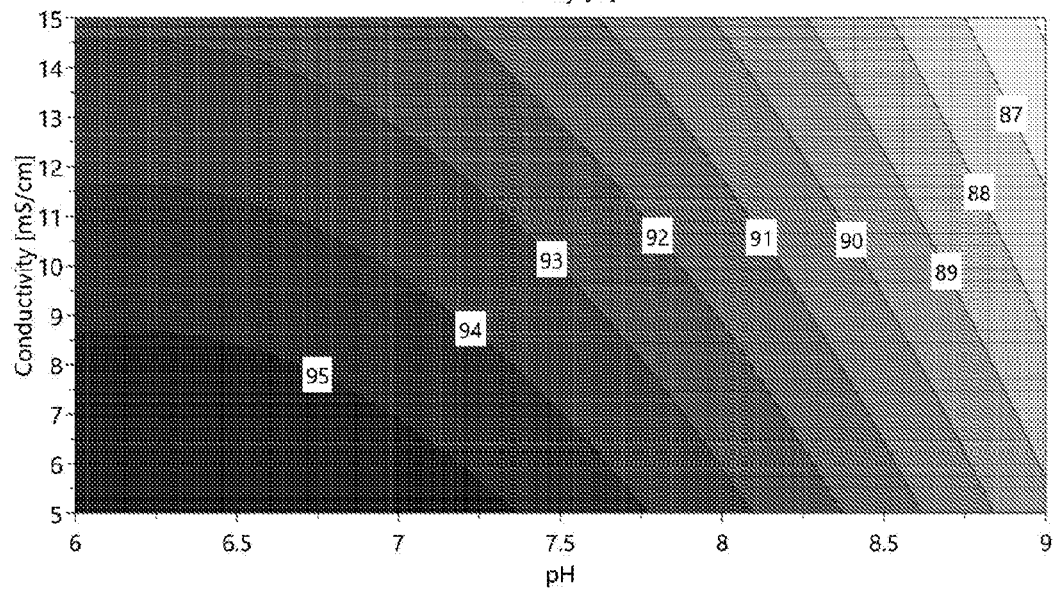
FIG. 9

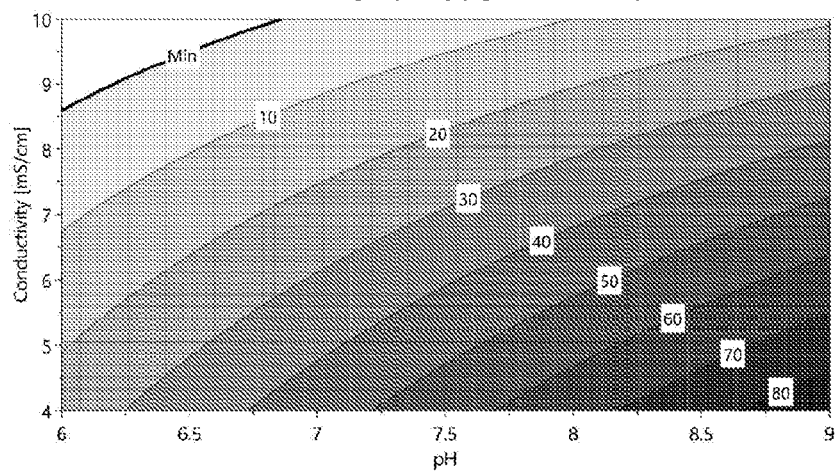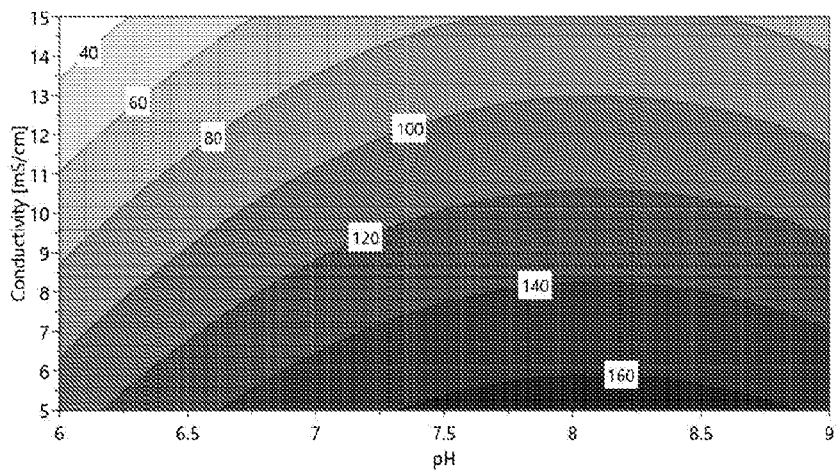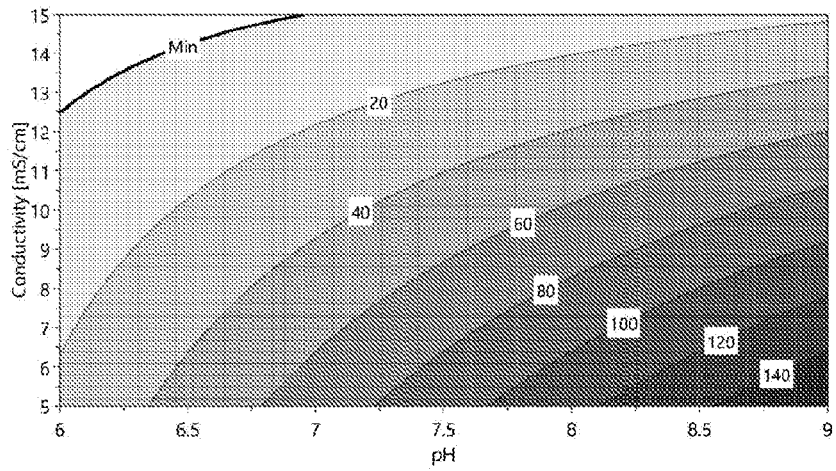
FIG. 11

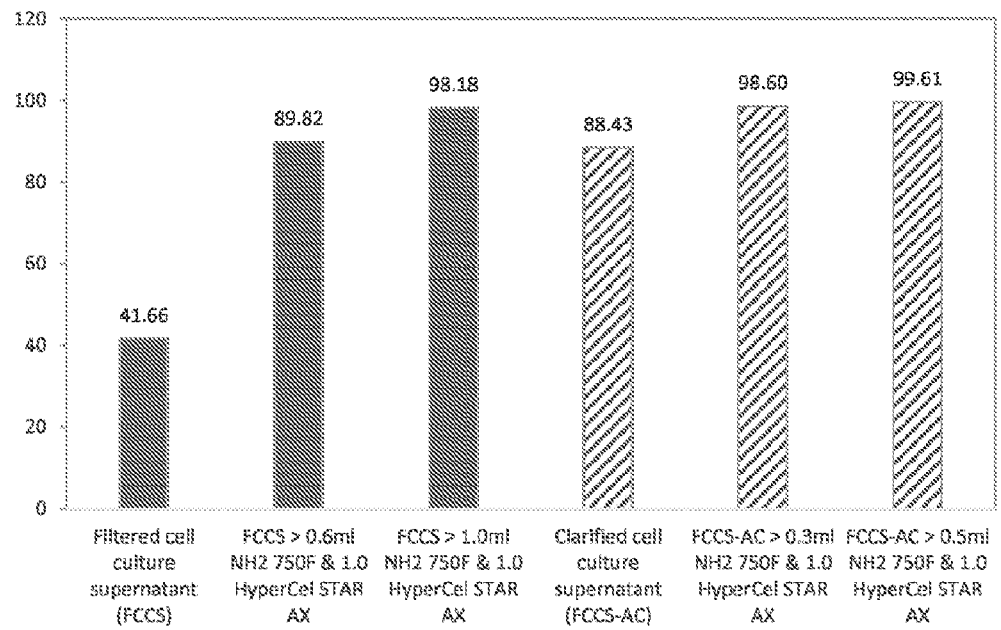
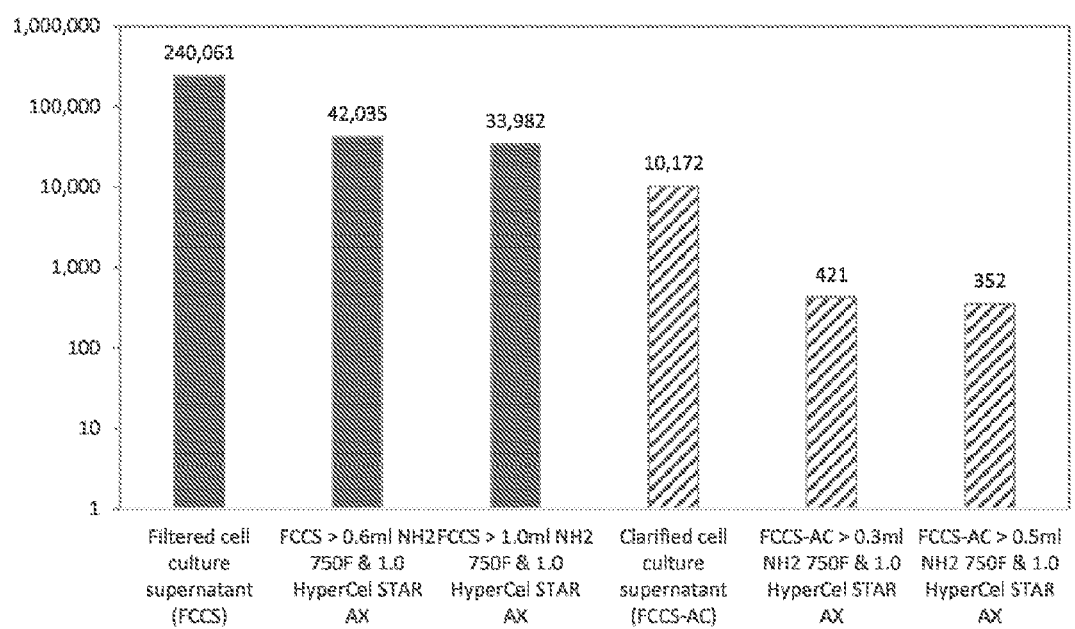
FIG. 12

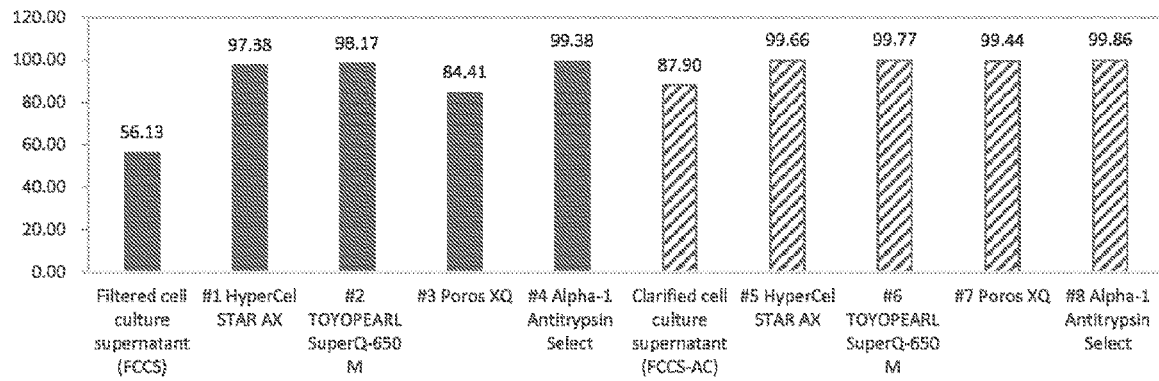
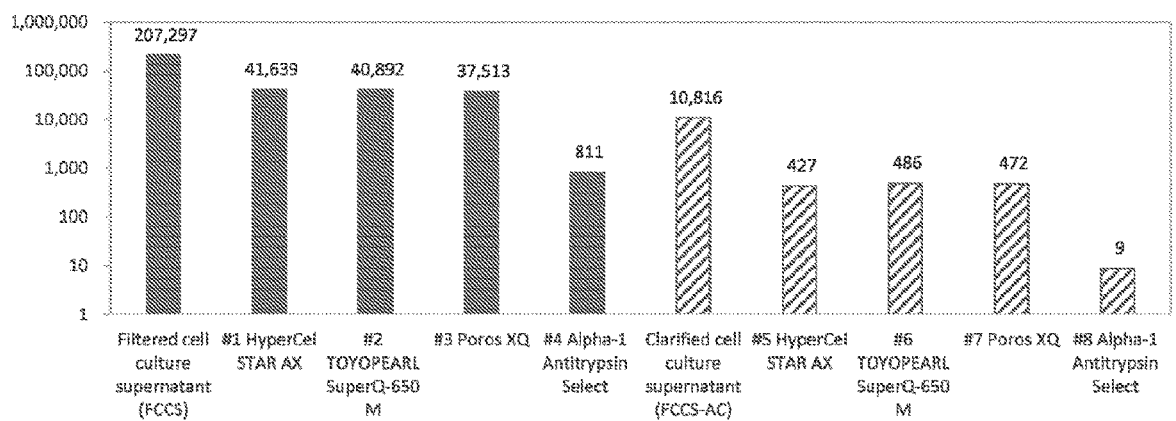
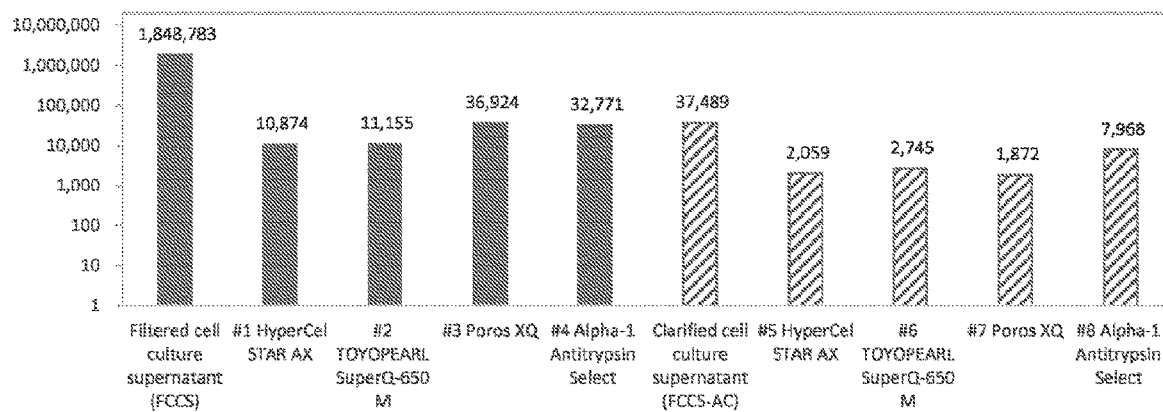
FIG. 14

METHOD OF CAPTURING AND/OR PURIFYING A TARGET

RELATED APPLICATIONS

This application is the U.S. National Stage of International Application No. PCT/SG2020/050150, filed Mar. 20, 2020, which designates the U.S., published in English, and claims priority under 35 U.S.C. § 119 or 365(c) to Singapore Application No. 10201902549Y, filed Mar. 21, 2019. The entire teachings of the above applications are incorporated herein by reference.

TECHNICAL FIELD

The present disclosure relates broadly to processes for the purification of targets. In particular methods of purifying and/or capturing a target using chromatography columns.

BACKGROUND

Traditionally, protein purification is operated in batch mode with a single column used in each unit operation. For recombinant proteins that are produced in cell culture supernatants, various purification techniques are required to remove process-related impurities (viruses, host cell proteins inclusive of high and low molecular weight species, host DNA/RNA and/or media components) and product-related impurities (aggregated proteins, fragments and/or product variants). Based on the characteristics of target proteins, potential purification techniques include affinity chromatography, ion-exchange chromatography, hydrophobic interaction chromatography, size exclusion chromatography, immobilized metal affinity chromatography, hydroxyapatite chromatography or multimodal chromatography.

Protein purification of recombinant proteins holds great promises in therapeutic applications. As an example, Alpha-1 antitrypsin (A1AT) is a protein that is produced mainly by the liver and that protects the body's own tissues from being damaged by infection-fighting agents released by its immune system. A1AT deficiency may lead to lung or liver diseases. Presently, intravenous infusion of A1AT concentrate extracted from human blood plasma is used as replacement therapy for A1AT deficiency. Recombinant A1AT is an attractive alternative as it potentially offers greater production capability and eliminates the risk associated with components in blood plasma such as immunoglobulin A.

Current purification methods of recombinant A1AT expressed in Chinese Hamster Ovary (CHO) cell culture rely on either anion exchange chromatography, affinity chromatography or size exclusion chromatography. However, these methods suffer from certain shortcomings. An anion exchanger typically binds any molecules with negative net surface charge; it is not specific to any target protein, and hence, an anion exchanger gives low purity. On the other hand, although affinity chromatography may exhibit high selectivity, it is typically costly and inefficient in removing aggregated proteins. Size exclusion chromatography is able to purify proteins depending on molecular weight difference but it has limited loading volume and flow rate in order to achieve good resolution.

In view of the above therefore, there is a need to provide an alternative system of capturing and/or purifying a target from a sample.

SUMMARY

In one aspect, there is provided a chromatography system comprising a first valve in fluid connection to a first chromatography column and/or a second valve; the second valve in fluid connection to a second chromatography column and the first valve; wherein the first valve and the second valve are operable to provide: i. a mode A that selectively allows a fluid to flow from the first chromatography column to the second chromatography column; ii. a mode B that selectively allows the fluid to bypass the first chromatography column; and/or iii. a mode C that selectively allows the fluid to bypass the second chromatography column.

In some embodiments, the first valve in fluid connection to the first chromatography column and the second valve in fluid connection to the second chromatography column are in tandem arrangement. In some embodiments, the first valve is operable to selectively allow fluid flow to flow through the first chromatography column; or to bypass the first chromatography column.

In some embodiments, an outlet of the first valve is linked to an inlet of the second valve.

In some embodiments, the second valve is operable to selectively allow fluid flow to flow through the second chromatography column or to bypass the second chromatography.

In some embodiments, i. in the mode A, the first valve directs the fluid to flow from the first chromatography column connected to the first valve to the second chromatography column connected to the second valve; ii. in the mode B, wherein the first valve directs the fluid to bypass the first chromatography column, thereby directing the fluid to flow from the first valve to the second chromatography column connected to the second valve; and iii. in the mode C, wherein the first valve directs the fluid to flow through the first chromatography column connected to the first valve to the second valve that directs the solution to bypass the second chromatography column.

In some embodiments, the first valve is an injection valve, optionally the second valve is a column valve.

In some embodiments, the first chromatography column is a flow-through chromatography column or a bind & elute chromatography column and the second chromatography column is a flow-through chromatography column or a bind & elute chromatography column In some embodiments, the first chromatography column is a flow-through chromatography column and the second chromatography column is a bind & elute chromatography column. In some embodiments, the system directs fluid to flow in mode A and in mode B, sequentially.

In some embodiments, the second valve is a column valve.

In some embodiments, the first chromatography column is a bind & elute chromatography column and the second chromatography column is a flow-through chromatography column. In some embodiments, the system directs fluid to flow in mode C and in mode A, sequentially.

In some embodiments, the first chromatography column is a bind & elute chromatography column and the second chromatography column is a bind & elute chromatography column. In some embodiments, the system directs fluid to flow in mode C, in mode A and in mode B, sequentially.

In some embodiments, the system further comprises one or more valve, optionally the valve is selected from the group consisting of an injection valve and a column valve.

In some embodiments, the first chromatography column and/or the second chromatography column is an affinity or non-affinity chromatography.

In some embodiments, the first chromatography column and/or the second chromatography column is an anion exchange chromatography.

In some embodiments, the first chromatography column is a high salt tolerant anion exchanger and/or the second chromatography column is a conventional anion exchange chromatography, high salt tolerant anion exchange chromatography and/or an affinity chromatography.

In some embodiments, the first chromatography column is a Toyopearl NH2 750F, optionally the second chromatography column is a bind & elute chromatography column selected from the group consisting of a conventional anion exchanger, a high salt tolerant anion exchanger, and an affinity chromatography.

In some embodiments, the first chromatography column is a Toyopearl NH2-750F and/or the second chromatography column is selected from the group consisting of Toyopearl Super Q-650, Capto Q, Q Sepharose, Mustang® Q, Sartobind Q, HyperCel™ Star AX, Poros XQ, and Alpha-1 Antitrypsin Select.

In another aspect, there is provided a method of purifying a target from a sample comprising providing a system according to any one of the preceding claims, and collecting the target from the system.

In some embodiments, the first chromatography column is a flow-through chromatography column or a bind & elute chromatography column and the second chromatography column is a flow-through chromatography column or a bind & elute chromatography column.

In some embodiments, the first chromatography column is a flow-through chromatography column and the second chromatography column is a bind & elute chromatography column. In some embodiments, when the system directs fluid to flow in mode A and in mode B, sequentially, the target is collected in mode B by disassociating the target from the second chromatography column.

In some embodiments, the first chromatography column is a bind & elute chromatography column and the second chromatography column is a flow-through chromatography column. In some embodiments, when the system directs fluid to flow in mode C and in mode A, sequentially, the target is collected in mode A by dissociating target from the first chromatography column and flow through the second chromatography column.

In some embodiments, the first chromatography column is a bind & elute chromatography column and the second chromatography column is a bind & elute chromatography column. In some embodiments, when the system directs fluid to flow in mode C, in mode A and in mode B, sequentially, the target is collected in mode B by disassociating the target from the second chromatography column.

In some embodiments, the target is a target protein, optionally an acidic protein. In some embodiments, the target is a recombinant acidic protein, optionally an alpha-1 anti-trypsin (A1AT).

In some embodiments, the purification is no less than about 90% pure, or no less than about 91%, or no less than about 92%, or no less than about 93%, or no less than about 94% or no less than about 95%, or no less than about 96%, or no less than about 97%, or no less than about 98%, or no less than about 99%.

In some embodiments, the sample is a supernatant (such as cell culture supernatant).

In some embodiments, the first valve, the second valve, the first chromatography column and the second chromatography column are integrated in a single closed- and self-contained apparatus.

Definitions

The term "micro" as used herein is to be interpreted broadly to include dimensions from about 1 micron to about 1000 microns.

The term "nano" as used herein is to be interpreted broadly to include dimensions less than about 1000 nm.

The term "particle" as used herein broadly refers to a discrete entity or a discrete body. The particle described herein can include an organic, an inorganic or a biological particle. The particle used described herein may also be a macro-particle that is formed by an aggregate of a plurality of sub-particles or a fragment of a small object. The particle of the present disclosure may be spherical, substantially spherical, or non-spherical, such as irregularly shaped particles or ellipsoidally shaped particles. The term "peptide" or "polypeptide" refers to a polymer of two or more of the natural amino acids or non-natural amino acids. The term "recombinant protein" or "recombinant polypeptide" refers to a polypeptide expressed from a host cell that has been genetically engineered to express that polypeptide. The recombinant expressed polypeptide can be identical or similar to polypeptides that are normally expressed in the host cell. The recombinant expressed polypeptide can also be foreign to the host cell. In some examples, the recombinant expressed polypeptide can be chimeric in that portions of the polypeptide contain amino acid sequences that are identical or similar to polypeptides normally expressed in the host cell, while other portions are foreign to the host cell. The polypeptide may be expressed from a gene that is endogenous to the host cell, or from a gene that is introduced into the host cell through genetic engineering.

The term "size" when used to refer to the particle broadly refers to the largest dimension of the particle. For example, when the particle is substantially spherical, the term "size" can refer to the diameter of the particle; or when the particle is substantially non-spherical, the term "size" can refer to the largest length of the particle.

The term "chromatography" refers to equipment and/or methods and/or techniques used in the separation of an analyte/a target (such as compounds and/or molecules and/or peptides of interest) from other molecules present in a mixture and/or in a solution. In some examples, the target of interest is separated from other molecules as a result of differences in binding affinity. The "binding" of a molecule to chromatography resin means exposing the molecule to chromatography resin under appropriate conditions known in the art (such as pH/ion concentration/conductivity) such that the molecule is reversibly immobilized in or on the chromatography resin by virtue of ligand-protein interactions. In some examples, the interactions may include, but is not limited to, ionic interactions between the molecule and a charged group or charged groups of the ion exchange material and a protein. In various embodiments, the chromatography may include, but is not limited to, flow-through chromatography and/or bind & elute chromatography. As used herein, the term "flow-through", or "flow-through process", or "flow-through chromatography", or "flow-through mode" may be used interchangeably to refer to a product separation technique or chromatography technique in which at least one analyte (for example a target peptide) contained in a sample is intended to flow-through a chromatographic resin or media, while at least one potential impurity (or contaminant) binds to the chromatographic resin or media. As used herein, the term "bind & elute chromatography" or "bind-elute" refers to a product separation technique in which at least one analyte (for example a target peptide) contained in a sample selectively binds to the separation chromatographic resin, whilst any impurities in the mixture flow through the chromatographic resin. In bind & elute chromatography, the analyte is then collected from a bind & elute chromatography by applying elution solution/medium/buffer.

The terms "coupled" or "connected" or "in fluid connection" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

The inventors of the present disclosure found a surprisingly simple chromatography system that has the flexibility to switch on or off a chromatography column depending on the operational needs of the system. As described in detail in the Examples section below, the present disclosure provides for a process design of a single system that elegantly allows for a chromatography column to be placed in line or bypassed depending on the process performed. The inventors of the present disclosure found that a combination of the first valve and the second valve advantageously provides four purification modes, which rely largely on the general ability of the system of the present disclosure to allow three different manners such as (1) both first and second chromatography columns are in line and are receiving fluid/solution/sample flow, (2) first chromatography column is bypassed while the second chromatography column is in line and is receiving fluid/solution/sample flow, (3) first chromatography column is in line (thus capable receiving fluid/solution/sample) and the second chromatography column is bypassed.

As such, in one aspect, there is provided a chromatography system comprising a first valve in fluid connection to a first chromatography column and/or a second valve; the second valve in fluid connection to a second chromatography column and the first valve; wherein the first valve and the second valve are operable to provide: i. a mode A that selectively allows a fluid to flow from the first chromatography column to the second chromatography column; ii. a mode B that selectively allows the fluid to bypass the first chromatography column; and/or iii. a mode C that selectively allows the fluid to bypass the second chromatography column.

In various embodiments, the first valve in fluid connection to the first chromatography column and the second valve in fluid connection to the second chromatography column are in tandem arrangement. As used herein, the phrase "tandem arrangement" refers to a technique or arrangement where two or more chromatography are coupled together. Thus, in various embodiments, the system as described herein may comprise two chromatography columns that are arranged one after another (or used in conjunction one another) and are in connection or coupled to one another by the use of one or more valve.

As used herein, the term "valve" refers to a component that is capable of allowing the selection of alternate flow routes through an instrument or an apparatus.

The inventors of the present disclosure found that the first valve may be conveniently positioned parallel to the first chromatography column. That is, the flow of fluid (that may comprise the sample) may be as follows: system pump to first valve with the first chromatography column in line to the second valve (see for example FIG. 4.2, FIG. 6.2, and the like). For example, during sample application via system pump, the first chromatography column is connected to a valve (such as an injection valve) in a parallel manner. That is, the first chromatography column is parallel to a valve (i.e. both inlet and outlet of column is connected to the valve (such as an injection valve)). Alternatively, first valve may be conveniently positioned after first chromatography column. That is, the flow of fluid (that may comprise the sample) may flow from the sample pump to the first chromatography column to the first valve then to the second valve (see for example FIG. 3.2, FIG. 5.2, and the like). For example, during sample application via sample pump, the first chromatography column is connected to a valve (such as an injection valve) in series. That is, the first chromatography column is in series with a valve (i.e. outlet of column is connected to inlet of the valve (such as an injection valve)).

When the first chromatography column is to be bypassed, the first valve would change internal flow path and direct fluid/solution from a pump (such as a system pump) to flow from first valve directly to the second valve, thus bypassing the first chromatography column. Therefore, in various embodiments, the first valve is operable to selectively allow fluid to (i) flow through the first chromatography column; or (ii) to bypass the first chromatography column. In various embodiments, the first valve is operable to selectively allow fluid to (i) flow through the first chromatography column to the second valve; or (ii) to bypass the first chromatography column to the second valve.

In various embodiments, an outlet of the first valve or the first chromatography column is in fluid connection to (or coupled to or linked to) an inlet of the second valve. In various embodiments, an outlet of the first valve is linked to an inlet of the second valve. For example, in FIG. 3.2, FIG. 3.3, FIG. 3.4, FIG. 4.2, FIG. 4.3, FIG. 4.4 and the like, position '1' is the outlet of first valve (Injection valve, V1) which channels flow directly to the inlet of the second valve (Column selection valve, V2). In FIG. 5.2, FIG. 5.3, FIG. 5.4, FIG. 6.2, FIG. 6.3, FIG. 6.4, and the like, position 'col' is the outlet of the first valve (Injection valve, V9-inj) which channels flow directly to the inlet of the second valve (Column valve, V9-C).

Upon receiving fluid from the first valve and/or the first chromatography column, the second valve may then allow fluid to the appropriate flow path depending on whether the second chromatography column is to be bypassed. If the second chromatography column is to be bypassed, the second valve would selectively allow fluid to flow directly to means for monitoring fluid/solution content. In various embodiments, where the second chromatography is to receive the fluid (i.e. in line), the second valve would selectively allow fluid to flow through the second chromatography column. Therefore, in various embodiments, the second valve is operable to selectively allow fluid to (i) flow through the second chromatography column or (ii) to bypass the second chromatography column (for example, to allow fluid from the second valve to flow directly to means for monitoring fluid/solution content).

In various embodiments, the system as described herein provides i. in the mode A, the first valve directs the fluid to flow from the first chromatography column connected to the first valve to the second chromatography column connected to the second valve; ii. in the mode B, wherein the first valve directs the fluid to bypass the first chromatography column, thereby directing the fluid to flow from the first valve to the second chromatography column connected to the second valve; and iii. in the mode C, wherein the first valve directs the fluid to flow through the first chromatography column connected to the first valve to the second valve that directs the solution to bypass the second chromatography column.

In some embodiments, the valve is an injection valve and/or a column valve. Without wishing to be bound by theory, whilst the use of injection valve and column valve is known in the art, the present inventors have found a surprisingly simple but effective configuration where a column (such as a chromatography column) is coupled/connected/installed on one or more valve (such as an injection valve) would be useful in providing a single (and closed) chromatography system that allows a seamless purification and/or selection of an analyte/target.

In some embodiments, the method provides an injection valve and a column valve.

In some embodiments, the valve is an injection valve. In various embodiments, the method comprises use of an injection valve to bypass the first column. In some examples, the valve is a commercially available injection valve in the art. In some embodiments, the valve comprises a plurality of port valves selected from the group consisting of 4 port valves, 6 port valves, 8 port valves, and 10 port valves.

In various embodiments, the first chromatography column is a flow-through chromatography column or bind & elute chromatography column and the second chromatography column is a flow-through chromatography column or bind & elute chromatography column.

In various embodiments, the first valve is an injection valve, optionally the second valve is a column valve.

In various embodiments, the first chromatography column is a flow-through chromatography column and the second chromatography column is a bind & elute chromatography column. In various embodiments, the system directs fluid to flow in mode A and in mode B, sequentially. That is, in some examples, the system directs the sample to flow from the sample pump or system pump into the first chromatography column, allowing any impurities (non-target components of a sample) to bind to the flow-through chromatography column and the target to flow through the first chromatography column. The first valve then allows the solution/fluid that flows through the first chromatography column to be directed into the second valve, which would direct the flow into the second chromatography column, which is a bind & elute chromatography, to thereby allowing the target to bind to the bind & elute chromatography column. Subsequently, in various embodiments, the first valve will redirect the flow as such the first chromatography column is bypassed and buffer (such as elution buffer) will come in contact with second chromatography column directly. As a result, target will dissociate from the second chromatography column.

In various embodiments, the first valve is an injection valve, optionally the second valve is a column valve.

In various embodiments, wherein the first chromatography column is a flow-through chromatography column and the second chromatography column is a flow-through chromatography column. In various embodiments, the system directs fluid to flow in mode A. That is, in some examples, the system directs the sample to flow from the sample pump or system pump into the first chromatography column followed by second chromatography column, allowing any impurities (non-target components of a sample) to bind to either the first or second flow-through chromatography column.

In various embodiments, the first valve is an injection valve, optionally the second valve is a column valve.

In various embodiments, the first chromatography column is a bind & elute chromatography column and the second chromatography column is a flow-through chromatography column. In various embodiments, the system directs fluid to flow in mode C and in mode A, sequentially. That is, in some examples, the system directs the sample to flow from the sample pump or system pump into the first chromatography column while bypassing second chromatography column, allowing target to bind to first bind & elute chromatography column only. Subsequently, the second valve will redirect the flow such that fluid will flow from first chromatography to second chromatography column. As a result, target will dissociate from first column and flow through second chromatography column in which residual impurities will bind to the second chromatography column.

In various embodiments, the first valve is an injection valve, optionally the second valve is a column valve.

In various embodiments, the first chromatography column is a bind & elute chromatography column and the second chromatography column is a bind & elute chromatography column.

In various embodiments, the system directs fluid to flow in mode C, in mode A and in mode B, sequentially. That is, in some embodiments, the system directs the sample to flow from the sample pump or system pump into the first chromatography column while bypassing second chromatography column, allowing target to bind to first bind & elute chromatography column only. Subsequently, the second valve will redirect the flow such that fluid will flow from first chromatography to second chromatography column. As a result, target will dissociate from first chromatography column and come in contact with the second chromatography column in which target will bind to the second chromatography column. Lastly, the first valve will redirect the flow such that first chromatography column is bypassed and fluid only flow through the second chromatography column. Hence, the target will dissociate from the second chromatography column.

In some examples, the system may provide two or more, or three or more, or four or more, or five or more valves. As such, in various embodiments, the system further comprises one or more valve, optionally the valve is selected from the group consisting of an injection valve, a column valve, and a flow channeling valve.

In various embodiments, the first chromatography column and/or second chromatography is an affinity or non-affinity chromatography column.

In various embodiments, the first chromatography column and/or the second chromatography column is an anion exchange chromatography.

In various embodiments, the first chromatography column is a high salt tolerant anion exchanger and/or the second chromatography column is a conventional anion exchange chromatography, high salt tolerant anion exchanger and/or an affinity chromatography.

In various embodiments, the first chromatography column is a non-affinity chromatography column while second chromatography column is an affinity chromatography column. In various embodiments, the first and/or second column comprises non-affinity chromatography. The performance of embodiments of the method which use non-affinity chromatography are comparable to affinity chromatography.

In various embodiments, the first column and the second column use anion exchange chromatographic resins. Advantageously, for anion exchange chromatographic resins, the flowrate is dependent on the residence time while the sample volume is affected by its dynamic binding capacity. Unlike other resin, e.g. size exclusion column, the flowrate is not a substantial limiting factor on the scalability of the method. By using anion exchanger in comparison with affinity chromatography, problems such as weak alkaline tolerance and antibody ligand leakage can also be eliminated.

In some embodiments, the first chromatography column is a high salt tolerant anion exchanger and/or the second chromatography column is a conventional anion exchanger chromatography, high salt tolerant anion exchange chromatography and/or an affinity chromatography.

In some embodiments, the first and/or second chromatography column is selected from the group consisting of Toyopearl Super Q-650, Capto Q, Q Sepharose, Mustang® Q, Sartobind Q, Toyopearl NH2-750F, HyperCel™ Star AX, Poros XQ, and Alpha-1 Antitrypsin Select. In some embodiments, the first chromatography column is a Toyopearl NH2-750F and/or the second chromatography column is Toyopearl Super Q-650, Capto Q, Q Sepharose, Mustang® Q, Sartobind Q, HyperCel™ Star AX, Poros XQ, and Alpha-1 Antitrypsin Select.

As would be appreciated, the chromatography system as disclosed herein would be useful when used in methods that purify/select/enrich a target from a sample. Thus, in another aspect, there is provided a method of purifying a target from a sample comprising a) providing a system according to any one of the preceding claims, and b) collecting the target from the system.

In various embodiments, the first chromatography column is a flow-through chromatography column and the second chromatography column is a bind & elute chromatography column. In various embodiments, when the system directs fluid to flow in mode A and in mode B, sequentially, the target is collected in mode B by disassociating the target from the second chromatography column.

In various embodiment, when the first chromatography column is a flow-through column, the first chromatography column may be a Toyopearl NH2 750F. In various embodiment, when the second chromatography column is a bind & elute mode, the second chromatography column may be selected from the group consisting of conventional anion exchanger (such as Toyopearl Super Q-650, Capto Q, Q Sepharose, Mustang® Q, Sartobind Q), high salt tolerant anion exchanger (such as HyperCel™ Star AX, Poros XQ), affinity chromatography (such as Alpha-1 Antitrypsin Select), and the like.

In various embodiments, the first chromatography column comprises Toyopearl NH2-750F is known as a high salt tolerant anion exchanger which can function in both flow-through and bind & elute mode to remove impurities for protein purification under appropriate conditions. Based on common knowledge of downstream processing, anion exchanger at pH 7 should bind to acidic protein target (protein with isoelectric point lower than 7), acting as bind and elute mode. In contrast, anion exchanger should not bind to alkaline protein target (protein with isoelectric point greater than 7), acting as flow-through mode. At the same time, Toyopearl NH2-750F also unexpectedly did not bind A1AT well under the conditions which it should bind based on common knowledge of downstream processing. Nevertheless, the present disclosure demonstrated that Toyopearl NH2-750F has an ability to preferentially bind impurities (such as aggregates) at pH greater than the pI of A1AT. As such, Toyopearl NH2-750F is surprisingly operating in pseudo flow-through mode and pose as a possible useful first chromatography candidate.

In various embodiments, the first chromatography column is a Toyopearl NH2 750F, optionally the second chromatography column is a bind & elute chromatography column selected from the group consisting of Toyopearl Super Q-650, Capto Q, Q Sepharose, Mustang® Q, Sartobind Q, HyperCel™ Star AX, Poros XQ, and Alpha-1 Antitrypsin Select, and the like.

In various embodiments, the first chromatography column is a Toyopearl NH2-750F and/or the second chromatography column is Toyopearl Super Q-650, Capto Q, Q Sepharose, Mustang® Q, Sartobind Q, HyperCel™ Star AX, Poros XQ, and Alpha-1 Antitrypsin Select.

In various embodiments of the methods as disclosed herein, the first chromatography column is a bind & elute chromatography column and the second chromatography column is a flow-through chromatography column. In various embodiments, in this method, when the system directs fluid to flow in mode C and in mode A, sequentially, the target is collected in mode A by disassociating target from the first chromatography column and (allowing the target to) flow through the second chromatography column.

In various embodiments of the methods as disclosed herein, the first chromatography column is a bind & elute chromatography column and the second chromatography column is a bind & elute chromatography column. In various embodiments, in this method, when the system directs fluid to flow in mode C, in mode A and in mode B, sequentially, the target is collected in mode B by disassociating the target from the second chromatography column.

As illustrated in the Examples section, the system and/or method as described herein not only provides the user with a convenient single system, it also provides a purification system and/or method that yields high separation or purification of target of interest. As such, in various embodiments, the system and/or method as described herein provides separation (or purification) that is no less than about 90% pure, or no less than about 91%, or no less than about 92%, or no less than about 93%, or no less than about 94% or no less than about 95%, or no less than about 96%, or no less than about 97%, or no less than about 98%, or no less than about 99%. As used herein, the term "purified" or "to purify" or any grammatical variations thereof, refers to the removal of impurities or other molecules that is not of the desired target. As such, the term "purifying" refers to the process of enriching a desired target relative to other components in a sample. For example, the present disclosure contemplates purification wherein the desired target is present in amounts that represent a fraction of the total components in a sample. In some embodiments, the purification process (or separation method or enrichment method/process) results in no less than 90% pure, or no less than about 91%, or no less than about 92%, or no less than about 93%, or no less than about 94% or no less than about 95%, or no less than about 96%, or no less than about 97%, or no less than about 98%, or no less than about 99%. That is, greater than 90%, or greater than 91%, or greater than 92%, or greater than 93%, or greater than 94%, or greater than 95%, or greater than 96%, or greater than 97%, or greater than 98%, or greater than 99% of impurities/contaminants are removed.

In various embodiments, the method is capable of achieving high monomer purity of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or at least about 100%.

In various embodiments, the method is capable of achieving high recovery of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or at least about 100%.

In some embodiments, the method is repeated one or more times, or two or more times, or three or more times. For example, the method is applied to one or more purification stages.

Without wishing to be bound by theory, it is believed that a method of purifying a target from a sample or recovering a purified protein product from a sample can be broadly separated into three different stages of 1) a capture stage, 2) an intermediate stage, and 3) a polishing stage. A capture stage isolates concentrates and stabilizes target. As such, capture stage prioritizes product recovery over purity and is typically also referred to as the initial recovery step. An intermediate stage removes bulk impurities. A polishing stage removes the most difficult impurities such as aggregates of the target.

In some examples, the method is applied to one or more purification stages selected from the group consisting of a capture stage, an intermediate stage, and a polishing stage.

In some embodiments, the method may be repeated once, twice, thrice, or more, in each purification stage. Thus, in some examples, the method may be repeated one time during one of capture stage, intermediate stage or polishing stage. In some examples, the method may be repeated two times during a capture stage, intermediate stage or polishing stage. In some examples, the method may be repeated one time during capture stage and intermediate stage and two times during polishing stage. In some examples, the method may only be repeated in one of capture stage or polishing stage. From the teaching of the present disclosure, other possible permutations of the number of repeats would not be beyond the skill of the person in the art.

As would be understood by the person skilled in the art, non-target impurity includes but is not limited to viruses, non-target proteins (such as host cell proteins of high and/or low molecular weight species), nucleic acids (such as (host cell) DNA, RNA, mRNA, and the like), aggregate (such as aggregated proteins), fragments and media components. In some examples, an "aggregate" may refer to an amorphous particle that forms from the association of two or more components (such as two or more proteins). The association may either be covalent or non-covalent and may be direct between the two or more components (such as proteins) or indirect between the two or more components (such as via other molecules that link the components together). Examples of the indirect association may include but are not limited to disulfide linkages via other proteins, hydrophobic associations via lipids, charge associations via DNA, affinity associations via leached component of the column, or mixed mode associations via multiple components. Heat and chemical denaturation may be the most common process that can lead to the formation of aggregate.

In some embodiments, the target is a target protein, optionally an acidic protein. In some embodiments, the target is a recombinant acidic protein, optionally an alpha-1 anti-trypsin (A1AT).

In some embodiments, the sample may be a supernatant (such as cell culture supernatant). As illustrated in the Examples section of the present disclosure, all parts of the system, apparatus, or component of the methods herein are part of an integrated, single closed or self-contained apparatus. Thus, in various embodiments, the first valve, the second valve, the first chromatography column and the second chromatography column are integrated in a single closed- and self-contained apparatus. As such, advantageously, embodiments of the method are able to integrate two purification steps within single operation, achieving pretreatment and initial recovery in single step purification.

Advantageously, embodiments of the methods are compatible with existing injection valve and column valve on Fast Protein Liquid Chromatography (FPLC) systems (e.g. GE Healthcare ÄKTA Explorer/Purifier/Pure/Avant/Bio-Rad NGC). Embodiments of the method may be easily implemented in conventional FPLC systems without the need to take columns offline physically and without the need for hardware modification. In various embodiments, the method does not require the installation of additional control valve or physical removal of the column.

In some examples, there is provided an apparatus configured to operate the chromatography system as disclosed herein. In some examples, there is also provided an apparatus for separating (or purifying) a target in a sample comprising a first column, a second column, and a valve, wherein the first column may be configured to bind non-target impurities and the second column may be configured to bind the target, and wherein the valve may be configured to allow the sample to flow from the first column to a second column. The apparatus of the present disclosure allows for the removal of non-target impurities (or contaminants or undesired components) from a sample.

In some examples, the first column may remove the non-target impurities from the original material by binding to the non-target impurities. In some examples, the second column may remove the target from the original material by capturing (or binding) the target. In some examples, the first column may be a negative chromatography or a flow-through chromatography. In some examples, the second column may be a positive chromatography or a bind & elute chromatography or a capture column.

In some examples, the valve may be configurable to allow a solution to flow through the first column followed by the second column. In some examples, the valve may be configured to allow a solution (such as equilibration buffer or sample) to flow through the first column followed by the second column.

In some examples, the valve may be further configurable to allow a solution to flow through the second column without flowing through the first column. In some examples, the valve may be configured to allow a solution (such as wash buffer or elution buffer) to flow to the second column and bypassing the first column. In some examples, the valve may be further configured to allow a second solution (or buffer or wash buffer or elution buffer) through the second column without directing through the first capture column.

In some examples, the first and/or second column may be a column chromatography. In some examples, the column chromatography may include micro-sized particles in a packed-bed column, a membrane column, or a monolith column/chromatography.

In some examples, the first and second columns may be arranged in a series (such as in tandem configuration). In some examples, the first and the second columns may be non-affinity columns.

In some embodiments, the first and/or second chromatography column is selected from the group consisting of Toyopearl Super Q-650, Capto Q, Q Sepharose, Mustang® Q, Sartobind Q, Toyopearl NH2 750F, HyperCel™ Star AX, Poros XQ, and Alpha-1 Antitrypsin Select In some embodiments, the first chromatography column is a Toyopearl NH2-750F and/or the second chromatography column is Toyopearl Super Q-650, Capto Q, Q Sepharose, Mustang® Q, Sartobind Q, HyperCel™ Star AX, Poros XQ, and Alpha-1 Antitrypsin Select.

In various embodiments, wherein the first chromatography column is a flow-through column and the second chromatography column is a bind & elute mode. In various embodiment, wherein the first chromatography column is a flow-through column and the first chromatography column is a Toyopearl NH2 750F. In various embodiment, wherein the second chromatography column is a bind & elute mode, the second chromatography column is selected from the group consisting of conventional anion exchanger (such as Toyopearl Super Q-650, Capto Q, Q Sepharose, Mustang® Q, Sartobind Q), high salt tolerant anion exchanger (such as HyperCel™ Star AX, Poros XQ), affinity chromatography (such as Alpha-1 Antitrypsin Select) and the like.

In some examples, the first column may be a Toyopearl NH2-750F and/or the second column is a Toyopearl Super Q-650. In some examples, the first column may be a Toyopearl NH2-750F and/or the second column may be HyperCel™ Star AX. In some examples, the first column may be a Toyopearl NH2-750F and/or the second column may be Poros XQ. In some examples, the first column may be a Toyopearl NH2-750F and/or the second column may be Alpha-1 Antitrypsin Select.

In some examples, the valve may be an injection valve. As such, in some examples, the first column may be connected to an injection valve.

In some examples, the apparatus may further comprise a column valve. As such, in some examples, the second column may be configured to be downstream of the first column. In some examples, the second column may be coupled to the first column via an optional column valve. In some examples, the first column in tandem configuration to the second column may be connected to an injection valve and the second column is located downstream from the first column with or without a column valve.

In some examples, the valve may be an injection valve with a plurality of port valves, such as but is not limited to 4 port valves, 6 port valves, 8 port valves, 10 port valves, and the like.

In some examples, the apparatus or system or method as described herein may further comprise one or more components such as but is not limited to a pressure monitor, a sample pump, a sample inlet valve, an inlet valve, a system pump, a mixer, a column valve, a UV monitor, a conductivity monitor, a pH monitor, a fractionator, and the like. Examples of liquid flow path in an apparatus is shown in the figures section.

In some examples, a system for separating (or purifying) a target from a sample comprising a first column for binding a non-target impurity, a second column for binding the target, and directing means for directing (or channeling or passing) the sample (to flow) from the first column to the second column. In some examples, the system may further allow for the directing means to direct a solution (or buffer or wash buffer or elution buffer) to the second column without directing through the first capture column. In some examples, the directing means is configured to allow a second solution (or buffer or wash buffer or elution buffer) through the second column without directing through the first capture column.

In some examples, the first column removes the non-target impurity by binding to the non-target impurity. In some examples, the second column removes the target by capturing (or binding) the target.

In some examples, the present disclosure also envisage a method of separating (or purifying) a target from a sample comprising a. contacting the sample comprising the target to a first column, wherein the first column captures (or bind to or removes) non-target impurities in the sample, b. contacting the target containing flow-through sample from a. to a second column, wherein the second column captures (or bind to or removes) the target from the sample, and c. eluting the target from the second column.

In some examples, c. comprises directing (or passing or channeling) a solution (to flow) to the second column without flowing through the first column to thereby elute the target from the second column. In some examples, the method further comprising directing (or passing or channeling) the solution (such as wash buffer or elution buffer) to the second column and bypassing the first column. In some examples, the method further comprises allowing a second solution (or buffer or wash buffer or elution buffer) through the second column without directing through the first column.

In some examples, the directing (or passing or channeling) of sample and/or solution (such as wash buffer or elution buffer) is achieved by the use of a valve. In some examples, the valve is an injection valve. In some examples, the first column is connected to an injection valve.

In some examples, the directing (or passing or channeling) a solution (to flow) to the second column without flowing through the first column is achieved by the use of an injection valve.

In some examples, the second column is located (or placed) downstream of the first column.

In some examples, the second column is coupled to the first column via an optional column valve. In some examples, the first column in tandem configuration may be connected to an injection valve and the second column is located downstream with or without column valve.

In some examples, the valve is configurable to allow a solution to flow through the first column followed by the second column. In some examples, the valve is configured to allow a solution (such as equilibration buffer or sample or wash buffer) to flow through the first column followed by the second column.

In some examples, the equilibration and sample application step in the method of the present disclosure may be illustrated in the Examples section. In some example, the equilibration and sample application and wash steps may include one or more of the following steps:
1. Set injection valve to "Inject" mode;
2. If column valve is used, set column to desired column position;
3. Introduce equilibration buffer; in some example, liquid flow path will direct solution from System pump→Injection valve with first chromatography column in line→Second chromatography column;
4. Once the columns are equilibrated, change equilibration buffer to sample in which sample will flow from first chromatography column to second chromatography column; and
5. Once sample application is completed, change sample to wash buffer.

In some example, the equilibration and sample application and wash steps may include one or more of the following steps:
1. Set injection valve to "Inject" mode;
2. If column valve is used, set column to desired column position;
3. Introduce equilibration buffer; in some example, liquid flow path will direct solution from Sample pump→Injection valve with first chromatography column in line→Second chromatography column;
4. Once the columns are equilibrated, change equilibration buffer to sample in which sample will flow from first chromatography column to second chromatography column; and
5. Once sample application is completed, change sample to wash buffer.

In some examples, the step of eluting the target from the second column comprises contacting the second column to an elution buffer. In some examples, the elution of anion exchange chromatography may be triggered by one or combination of the following condition:
1. Increasing the conductivity of buffer; and/or
2. Decreasing pH value of buffer to be lower than the pI of target protein.

In some examples, the elution step in the method of the present disclosure may be illustrated in the Examples section. In some example, the elution step may include one or more of the following steps:
1. Set injection valve to "Load" mode in order to bypass the first column;
2. Change the wash buffer to elution buffer; in some example, liquid flow path will direct solution from System pump→Injection valve bypassing first chromatography column→Second chromatography column; and
3. Collect the eluate.

In some examples, the buffer comprises one or more components of buffering ions and counterions. In some example, the buffering ion may include but is not limited to 2-Morpholinoethanesulfonic Acid (or MES), 4-(2-hydroxyethyl)-1-piperazineethanesulfonic acid (or HEPES) or Trisaminomethane (or Tris) and the counterion or salt ion may include but is not limited to Sodium Chloride (NaCl).

In some examples, the buffer (for example equilibration buffer or running buffer or binding buffer or wash buffer) may comprise about 10 mM to 50 mM buffering ions and an appropriate concentration of counterions. In some example, the pH of buffer is higher than theoretical pI of target and pH 2.0 units higher is preferred. In some example, the conductivity of buffer maybe no more than 10 mS/cm for conventional anion exchange chromatography and no more than 15 mS/cm for high salt tolerant anion exchange chromatography. In some example, the equilibration buffer and/or binding buffer may be 10 mM to 50 mM Tris, pH 7 to 9, and 0 mM to 150 mM NaCl; or 15 mM to 45 mM Tris, pH 8 to 8.5, and 10 mM to 130 mM NaCl; or 50 mM Tris, pH 8.2, and 125 mM NaCl.

In some examples, the elution buffer has pH of about 3.0 to 10.0 and/or higher counterion concentration than equilibration buffer. In some examples, at pH higher than the theoretical pI of target, conductivity of elution buffer will be higher than that of equilibration buffer. For instance, the elution buffer at pH 9 with 1M NaCl may be able to trigger protein elution due to change in ionic strength of buffer. In some examples, at pH lower than the theoretical pI of target, any conductivity is appropriate for elution due to change in net charge of protein. For instance, elution buffer at pH 3.0 with no NaCl may be able to trigger protein elution as target protein has a net positive charge at pH lower than pI of the protein.

In some examples, the sample is a supernatant (such as cell culture supernatant).

Also described herein are apparatus, system, or methods as described in the figures or any parts of the disclosure herein.

BRIEF DESCRIPTION OF FIGURES

FIG. 2 illustrates the fluid flow path in ÄKTA Purifier/Explorer for sample application using sample pump a) using sample pump during equilibration and sample application and b) using system pump during wash and elution, and the c) corresponding ÄKTA chromatograph of a tandem column using flow-through chromatography in series with bind & elute chromatography in accordance with embodiments of the method. Inline sensors refer to pH, conductivity and UV sensors. pH: inline pH monitoring of sample and buffer; conductivity: inline conductivity monitoring of sample and buffer; UV: inline UV absorbance to monitor the presence of proteins and other components such as DNA and media components. In the context of protein purification, UV absorbance at 280 nm is used to trace the presence of proteins; Fractionator: collect samples in fractions.

FIG. 3.1 is a conventional fluid flow path diagram in ÄKTA Purifier/Explorer using both system pump and sample pump.

FIG. 3.2 is an example of fluid flow path in ÄKTA Purifier/Explorer using both system pump and sample pump for first manner (mode A) which allows a flow from the first chromatography column to the second chromatography column.

FIG. 3.3 is an example of fluid flow path in ÄKTA Purifier/Explorer using both system pump and sample pump for second manner (mode B) which first chromatography column is bypassed and flow only goes through second chromatography column.

FIG. 3.4 is an example of fluid flow path in ÄKTA Purifier/Explorer using both system pump and sample pump for third manner (mode C) which allows a flow through the first chromatography column while second chromatography column is bypassed.

FIG. 4.1 is a conventional fluid flow path in ÄKTA Purifier/Explorer using system pump only.

FIG. 4.2 is an example of fluid flow path in ÄKTA Purifier/Explorer using system pump only for first manner (mode A) which allows a flow from the first chromatography column to the second chromatography column.

FIG. 4.3 is an example of fluid flow path in ÄKTA Purifier/Explorer using system pump only for second manner (mode B) which first chromatography column is bypassed and flow only goes through second chromatography column.

FIG. 4.4 is an example of fluid flow path in ÄKTA Purifier/Explorer using system pump only for third manner (mode C) which allows a flow through the first chromatography column while second chromatography column is bypassed.

FIG. 5.1 is a conventional fluid flow path in ÄKTA Pure/Avant using both system pump and sample pump.

FIG. 5.2 is an example of fluid flow path in ÄKTA Pure/Avant using both system pump and sample pump for first manner (mode A) which allows a flow from the first chromatography column to the second chromatography column.

FIG. 5.3 is an example of fluid flow path in ÄKTA Pure/Avant using both system pump and sample pump for second manner (mode B) which first chromatography column is bypassed and flow only goes through second chromatography column.

FIG. 5.4 is an example of fluid flow path in ÄKTA Pure/Avant using both system pump and sample pump for third manner (mode C) which allows a flow through the first chromatography column while second chromatography column is bypassed.

FIG. 6.1 is a conventional fluid flow path in ÄKTA Pure/Avant using system pump only.

FIG. 6.2 is an example of fluid flow path in ÄKTA Pure/Avant using system pump only for first manner (mode A) which allows a flow from the first chromatography column to the second chromatography column.

FIG. 6.3 is an example of fluid flow path in ÄKTA Pure/Avant using system pump only for second manner (mode B) which first chromatography column is bypassed and flow only goes through second chromatography column.

FIG. 6.4 is an example of fluid flow path in ÄKTA Pure/Avant using system pump only for third manner (mode C) which allows a flow through the first chromatography column while second chromatography column is bypassed.

FIG. 9 shows the response contour plots of a) the static binding capacity (μg A1AT/μl resin) of TOYOPEARL NH2 750F b) the purity of A1AT (%) in flow-through at different binding conditions from HPLC-SEC analysis in one example.

FIG. 11 shows the response contour plots of the static binding capacity (μg A1AT/μl resin) of a) TOYOPEARL SuperQ-650 M b) HyperCel Star AX and c) Poros XQ based on eluate tested HPLC-SEC analysis in one example.

FIG. 12 shows the performance of tandem column configuration in terms of a) purity (%) and b) residual HCP (ppm) using filtered cell culture supernatant (FCCS) or clarified cell culture supernatant (FCCS-AC) with different volumes of TOYOPEARL NH2 750F column in one example.

FIG. 14 compares the performance of different tandem column configurations in terms of a) purity (%), b) residual HCP(ppm) and c) residual DNA (ppb) using filtered cell culture supernatant (FCCS) or clarified cell culture supernatant (FCCS-AC) by varying a selection of a second column in one example.

EXAMPLES

Figure 1:
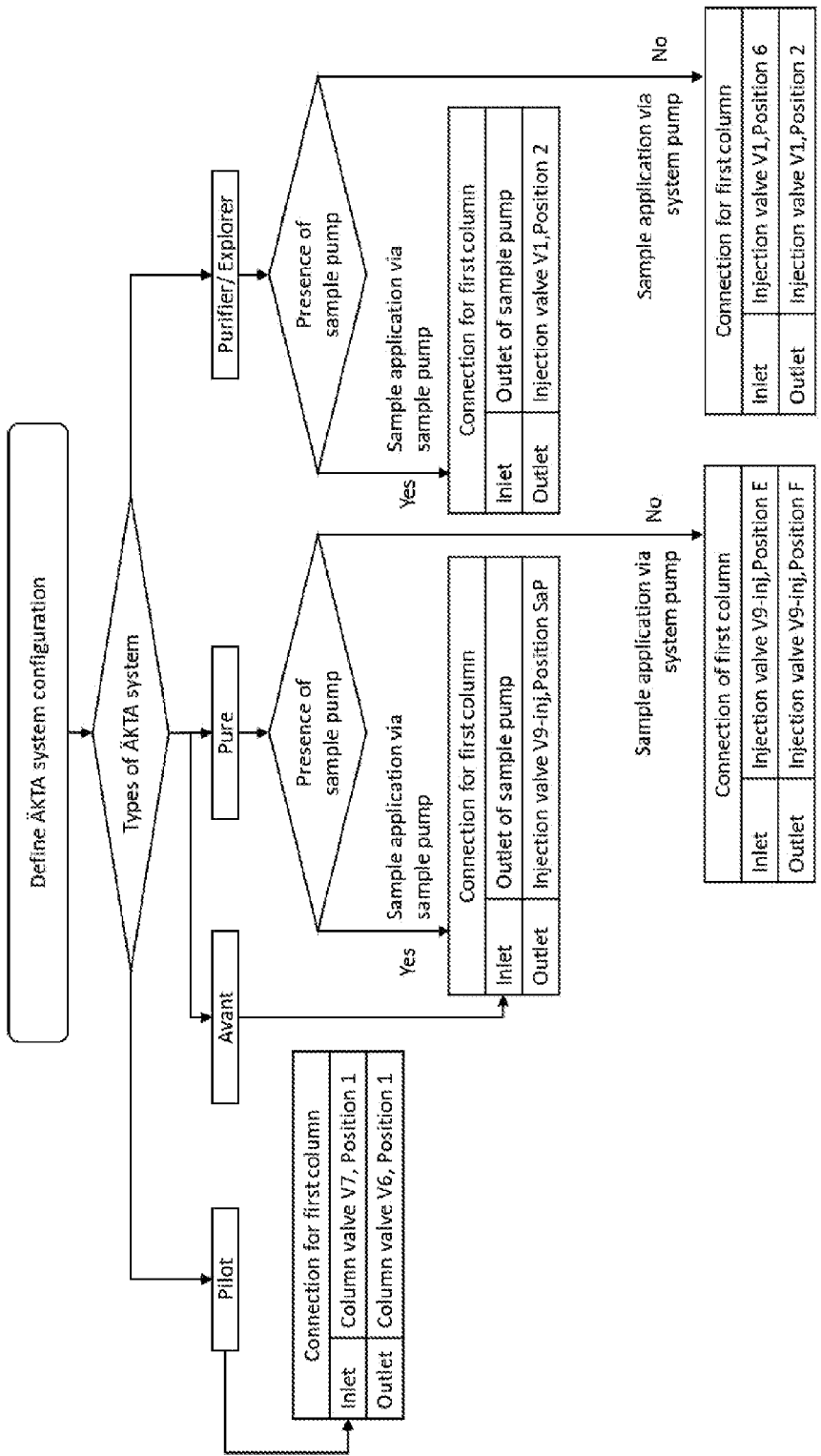
FIG. 1 is a flow chart showing the tandem configurations in different ÄKTA systems in accordance with embodiments of the method.

Example embodiments of the disclosure will be better understood and readily apparent to one of ordinary skill in the art from the following discussions and if applicable, in conjunction with the figures. It should be appreciated that other modifications related to structural, electrical and optical changes may be made without deviating from the scope of the invention. Example embodiments are not necessarily mutually exclusive as some may be combined with one or more embodiments to form new exemplary embodiments.

Chromatography Configurations

There are two main types of chromatography: (1) positive chromatography/bind & elute chromatography/capture; and (2) negative chromatography/flow-through chromatography. When there is more than one chromatographic step, the steps typically involve: (1) a capture (initial recovery) step; (2) an intermediate step; and (3) a polishing step.

In process development, product recovery is prioritized over purity in the capture step. Therefore, bind & elute chromatography (as opposed to flow-through chromatography) is almost always preferred as it is able to concentrate and reduce the volume of intermediate products for further purification. Even though flow-through chromatography may have its advantage of removing aggregates, it is rarely used in the capture step.

This disclosure describes a combination (amalgamation) of flow-through and bind & elute chromatography in a single step purification that gives high purity and high yield. Advantageously, the tandem column configuration can be applied in existing Fast Protein Liquid Chromatography (FPLC) system, resulting in excellent performance in terms of purity and recovery. No modification of hardware is required in order to switch on or off the individual columns connected in series.

The function of an injection valve in an ÄKTA system (e.g. ÄKTA Pure) is typically to channel sample from sample pump or sample in sample loop to a chromatography column located downstream (see FIG. 3.1, 4.1, 5.1 and 6.1 for a conventional fluid flow path of an FPLC). However, in the present disclosure, the inventors have found a new arrangement whereby a chromatography column was added in between the sample pump and an injection valve or replaced the sample loop. As a result, the sample is channeled from either the system pump or sample pump to the first chromatography column connected to the injection valve, before reaching the column valve or the second chromatography column located downstream. See FIG. 1 on a guide of how first chromatography column can be connected to an injection valve.

On the other hand, a column valve typically used for bypassing a chromatography column or to change the position of a chromatography column in some examples. The column valve enables multiple columns to be attached at different positions. However, only single column position may be used at one time. Currently, where tandem columns are used, they are connected to the same position and the first column is removed when necessary. Alternatively, an additional column valve is commonly installed to achieve bypassing. However, this is not desirable. For modulus system such as ÄKTA Pure, column valve (V9-C in FIGS. 5 and 6) may not be present. However, the column can still be connected at this area. Mode A and B as disclosed herein would still be applicable when second chromatography column is in line.

In some examples, this disclosure describes bypassing first chromatography column. In some examples, it is not necessary to bypass the second chromatography column when flow-through chromatography is paired with bind & elute chromatography. Therefore, embodiments of the method may desirably work on FPLC system without existing column valve.

The tandem configuration described is applicable to different models of ÄKTA systems of different scales from laboratory to pilot scale. Conventionally, injection valve is used to inject a sample into a column connected at column valve. For "inject" mode in an ÄKTA system (e.g. ÄKTA Purifier 100), fluid may flow from a first position (e.g. see position 6 in FIG. 23.1) to a second position (e.g. see position 2 in FIG. 23.1) which leads to a column valve located downstream. However, during "load" mode, this flow path is bypassed. By making use of the special configuration of the injection valve, a column installed between the first and second positions can be switched on and off without additional column valve. This enables embodiments of the method to be applicable on different scales of ÄKTA systems. Embodiments of the method is scalable from 1 ml column using ÄKTA Purifier/Explorer or ÄKTA Pure/Avant to 2 L column using ÄKTA Pilot with the potential to be applicable on manufacturing scale.

The flowchart shown in FIG. 1 provides an example of an appropriate installation of columns in series. Sample application via sample pump is recommended for systems with existing sample pump to minimise hold up volume. Nevertheless, sample application via system pump is also compatible with all systems with or without sample pump.

To illustrate, in one example, to operate tandem configuration on ÄKTA Purifier/Explorer with a sample pump, the first column is connected to the outlet of sample pump and position 2 on the injection valve while the second column is connected to the column valve as per normal (FIG. 2 and Table 2 below). Either column in this tandem configuration can be flow-through chromatography or bind & elute chromatography using any purification techniques available. The operation will be valid as long as the suitable purification mechanisms are paired together with appropriate buffer conditions.

In one example, the first column was connected to an injection valve and operated in flow-through mode while the second column was connected to a column valve located downstream and operated in bind and elute mode. During column equilibration, the injection valve was changed to "Inject" mode while column valve was changed to the selected "Column position". Equilibration buffer was allowed to flow from a sample pump to the first column connected to an injection valve, followed by the second column connected to a column valve and all the sensors located downstream. Once the pH and conductivity stabilize, sample valve was switched to the sample line in which the sample was loaded to these two columns connected in series. When a desired amount of sample was applied to the system, the sample pump switched to equilibration buffer line to push the remaining sample caused by system dead volume to the column. In this sample application phase, the first column bound the impurities while the second column bound the target protein. The unbound components were collected as flow-through.

After completing the sample application, the sample pump was stopped and the injection valve was changed to "Load" mode in order to bypass the column. Equilibration buffer from the system pump was directed from the injection valve, bypassing the first column, to the second column position at column valve. This is to further remove all the unbound components from the column. UV absorbance was observed to approach baseline indicating the absence of proteins.

Finally, during elution, system pump was switched to elution buffer. The target protein was dissociated from the column and collected as an eluate. It is crucial to bypass the first column, especially during the elution phase as the elution buffer would cause bounded impurities to dissociate, thus contaminating the eluate from the second column when pooled together. This would significantly compromise the process performance in terms of purity.

Under the same binding conditions, the first column operating in flow-through mode was able to capture impurities such as CHO host cell proteins, host DNA/RNA and aggregates. This allows the supernatant to be pre-treated before entering the second column, where target protein in the supernatant binds predominantly.

During elution, the first column was bypassed with only the second column in line. The target protein was eluted by changing the buffer condition, and both columns can be regenerated under the same conditions.

Embodiments of the method may be particularly useful when applied in the capture step. The following examples will therefore demonstrate embodiments of the method in the context of the capture step. However, it will be understood that embodiments of the method described herein can be applied and/or adapted for any of the purification steps mentioned above (including intermediate step and polishing step) without departing from the spirit of the invention.

Purification of Alpha-1 antitrypsin (A1AT) expressed in CHO cell culture is carried out in the following examples. A1AT is an acidic protein with theoretical isoelectric point (pI) of 5.37 and molecular weight (MW) of 52 kDa.

Process Design with Tandem Chromatography Column

The chromatography system as disclosed herein may include four possible combinations (see Table 1 below).

TABLE 1

Possible tandem chromatography combinations

| Combination | Purification mode of first chromatography column | Purification mode of second chromatography column |
| --- | --- | --- |
| 1 | Flow-through chromatography | Bind & elute chromatography |
| 2 | Bind & elute chromatography | Flow-through chromatography |
| 3 | Bind & elute chromatography | Bind & elute chromatography |
| 4 | Flow-through chromatography | Flow-through chromatography |

Figure 7:
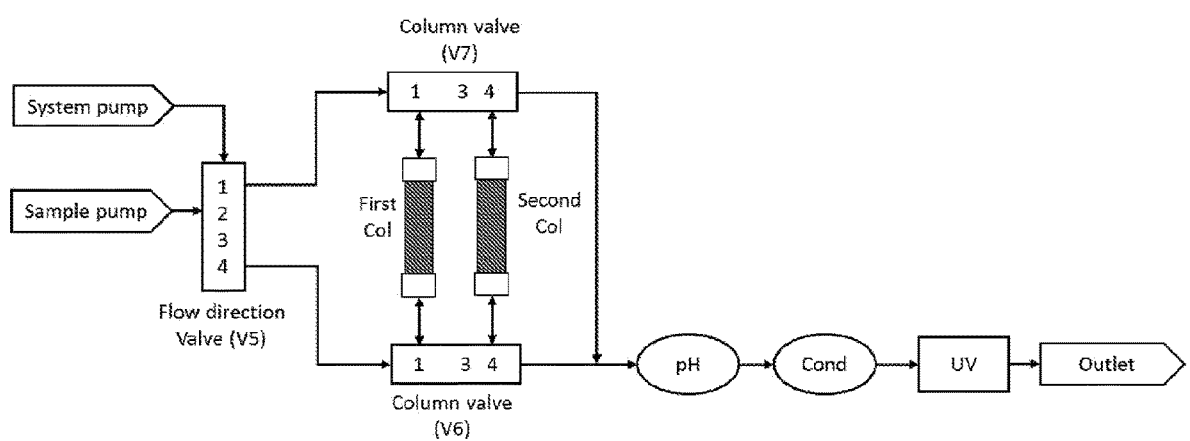
FIG. 7 illustrates a fluid flow path in ÄKTA Pilot in accordance with an embodiment of the method. As the column valve of ÄKTA pilot comes with the function to operate columns in series and no injection valve is available, both columns are installed at the column valve

Examples of hardware installation of columns the corresponding fluid flow path on ÄKTA Explorer/Purifier/Pure/Avant can be found in FIG. 3 to FIG. 6 while hardware installation of columns on ÄKTA Pilot can be found on FIG. 7.

i) First Column is Flow-Through Mode and Second Column is Bind & Elute Mode

The sample flows from first column (via injection valve at "INJECT" command) to second column (via column valve at "Column position" command);

Subsequently, first column is bypassed (via injection valve at "LOAD" command) and elution buffer will only dissociate target from second column.

Sample application phase of the first column will overlap with sample application phase of second column

TABLE 2

Operating command for tandem column operated on ÄKTA Explorer/Purifier/Pure/Avant when flow-through chromatography is paired with bind & elute chromatography with sample application via sample pump

| | Phase of $1^{st}$ column | Phase of $2^{nd}$ column | Inlet | Injection valve command | First column status | Column valve command | Second column status | Outlet | Fluid flow path |
| --- | --- | --- | --- | --- | --- | --- | --- | --- | --- |
| 1 | Equilibration | Equilibration | Sample pump - equilibration buffer | Inject | In line | Selected column position | In line | Waste | First manner (mode A) |
| 2.1 | Sample application | Sample application | Sample pump - sample | Inject | In line | Selected column position | In line | Fractionator | FIG. 3.2 FIG. 5.2 |

TABLE 2-continued

Operating command for tandem column operated on ÄKTA Explorer/Purifier/Pure/Avant when flow-through chromatography is paired with bind & elute chromatography with sample application via sample pump

| | Phase of 1st column | Phase of 2nd column | Inlet | Injection valve command | First column status | Column valve command | Second column status | Outlet | Fluid flow path |
|---|---|---|---|---|---|---|---|---|---|
| 2.2 | Complete sample application | Complete sample application | Sample pump - equilibration buffer | Inject | In line | Selected column position | In line | Fractionator | |
| 3 | Idle | Wash | System pump - wash buffer or equilibration buffer (only if equilibration buffer is same as wash buffer) | Load | Bypass | Selected column position | In line | Waste | Second manner (mode B) FIG. 3.3 FIG. 5.3 |
| 4 | Idle | Elution | System pump - elution buffer | Load | Bypass | Selected column position | In line | Fractionator | |

TABLE 3

Operating command for tandem column operated on ÄKTA Explorer/Purifier/Pure/Avant when flow-through chromatography is paired with bind & elute chromatography with sample application via system pump

| | Phase of 1st column | Phase of 2nd column | Inlet | Injection valve command | First column status | Column valve command | Second column status | Outlet | Fluid flow path |
|---|---|---|---|---|---|---|---|---|---|
| 1 | Equilibration | Equilibration | System pump - equilibration buffer | Inject | In line | Selected column position | In line | Waste | First manner (mode A) |
| 2.1 | Sample application | Sample application | System pump - sample | Inject | In line | Selected column position | In line | Fractionator | FIG. 4.2 FIG. 6.2 |
| 2.2 | Complete sample application | Complete sample application | System pump - equilibration buffer | Inject | In line | Selected column position | In line | Fractionator | |
| 3 | Idle | Wash | System pump - wash buffer or equilibration buffer (only if equilibration buffer is same as wash buffer) | Load | Bypass | Selected column position | In line | Waste | Second manner (mode B) FIG. 4.3 FIG. 6.3 |
| 4 | Idle | Elution | System pump - elution buffer | Load | Bypass | Selected column position | In line | Fractionator | | ii) First Column is Bind & Elute and Second Column is Flow-Through Mode

Sample will flow to first column only (via injection valve at "INJECT" command) while second column (via column valve at "column bypass" command) is bypassed during sample application and wash;

During elution, target will dissociate from the first column (via injection valve at "INJECT" command) and flow to second column (via column valve at "selected column position");

Elution phase of first column will overlap with the sample application phase of second column.

TABLE 4

Operating command for tandem column operated on ÄKTA Explorer/Purifier/Pure/Avant when bind & elute chromatography is paired with flow-through chromatography with sample application via sample pump

| | Phase of 1st column | Phase of 2nd column | Inlet | Injection valve command | First column status | Column valve command | Second column status | Outlet | Fluid flow path |
|---|---|---|---|---|---|---|---|---|---|
| 1 | Equilibration | Equilibration | Sample pump - equilibration buffer | Inject | In line | Selected column position | In line | Waste | First manner (mode A) FIG. 3.2 FIG. 5.2 |

TABLE 4-continued

Operating command for tandem column operated on ÄKTA Explorer/Purifier/Pure/Avant when bind & elute chromatography is paired with flow-through chromatography with sample application via sample pump

| | Phase of 1st column | Phase of 2nd column | Inlet | Injection valve command | First column status | Column valve command | Second column status | Outlet | Fluid flow path |
|---|---|---|---|---|---|---|---|---|---|
| 2.1 | Sample application | Idle | Sample pump - sample | Inject | In line | Column Bypass | Bypass | Fractionator | Third manner |
| 2.2 | Complete sample application | Idle | Sample pump - equilibration buffer | Inject | In line | Column Bypass | Bypass | Fractionator | (mode C) FIG. 3.4 FIG. 5.4 |
| 3 | Wash | Idle | Sample pump - wash buffer or equilibration buffer (only if equilibration buffer is same as wash buffer) | Inject | In line | Column Bypass | Bypass | Waste | |
| 4 | Elution | Sample application | Sample pump - elution buffer | Inject | In line | Selected column position | In line | Fractionator | First manner (mode A) FIG. 3.2 FIG. 5.2 |

TABLE 5

Operating command for tandem column operated on ÄKTA Explorer/Purifier/Pure/Avant when bind & elute chromatography is paired with flow-through chromatography with sample application via system pump

| | Phase of 1st column | Phase of 2nd column | Inlet | Injection valve command | First column status | Column valve command | Second column status | Outlet | Fluid flow path |
|---|---|---|---|---|---|---|---|---|---|
| 1 | Equilibration | Equilibration | System pump - equilibration buffer | Inject | In line | Selected column position | In line | Waste | First manner (mode A) FIG. 4.2 FIG. 6.2 |
| 2.1 | Sample application | Idle | System pump - Sample | Inject | In line | Column Bypass | Bypass | Fractionator | Third manner |
| 2.2 | Complete sample application | Idle | System pump - equilibration buffer | Inject | In line | Column Bypass | Bypass | Fractionator | (mode C) FIG. 4.4 FIG. 6.4 |
| 3 | Wash | Idle | System pump - wash buffer or equilibration buffer (only if equilibration buffer is same as wash buffer) | Inject | In line | Column Bypass | Bypass | Waste | |
| 4 | Elution | Sample application | System pump - elution buffer | Inject | In line | Selected column position | In line | Fractionator | First manner (mode A) FIG. 4.2 FIG. 6.2 | iii) First Column is Bind & Elute Mode and Second Column is Bind & Elute Mode

Sample will flow to first column only (via injection valve at "INJECT" command) while second column (via column valve at "column bypass" command) is bypassed during sample application and wash;

During elution, target will dissociate from the first column (via injection valve at "INJECT" command) and flow to second column (via column valve at "selected column position");

During 2nd elution, first column will be bypassed (via injection valve at "load" command);

Elution phase of first column will overlap with the sample application phase of second column.

TABLE 6

Operating command for tandem column operated on ÄKTA Explorer/Purifier/Pure/Avant when bind & elute chromatography is paired with bind & elute chromatography with sample application via sample pump

| | Phase of 1st column | Phase of 2nd column | Inlet | Injection valve command | First column status | Column valve command | Second column status | Outlet | Fluid flow path |
|---|---|---|---|---|---|---|---|---|---|
| 1 | Equilibration | Equilibration | Sample pump - equilibration buffer 1 | Inject | In line | Selected column position | In line | Waste | First manner (mode A) FIG. 3.2 FIG. 5.2 |
| 2.1 | Sample application | Idle | Sample pump - sample | Inject | In line | Column Bypass | Bypass | Fractionator | Third manner (mode C) FIG. 3.4 FIG. 5.4 |
| 2.2 | Complete sample application | Idle | Sample pump - equilibration buffer 1 | Inject | In line | Column Bypass | Bypass | Fractionator | |
| 3 | Wash | Idle | Sample pump - wash buffer 1 or equilibration buffer 1 (only if equilibration buffer is same as wash buffer) | Inject | In line | Column Bypass | | Waste | |
| 4 | Elution | Sample application | Sample pump - elution buffer | Inject | In line | Selected column position | In line | Fractionator | First manner (mode A) FIG. 3.2 FIG. 5.2 |
| 5 | Idle | Wash | System pump - wash buffer 2 | Load | Bypass | Selected column position | In line | Waste | Second manner (mode B) |
| 6 | Idle | Elution | System pump - elution buffer 2 | Load | Bypass | Selected column position | In line | Fractionator | FIG. 3.3 FIG. 5.3 |

TABLE 7

Operating command for tandem column operated on ÄKTA Explorer/Purifier/Pure/Avant when bind & elute chromatography is paired with bind & elute chromatography with sample application via system pump

| | Phase of 1st column | Phase of 2nd column | Inlet | Injection valve command | First column status | Column valve command | Second column status | Outlet | Fluid flow path |
|---|---|---|---|---|---|---|---|---|---|
| 1 | Equilibration | Equilibration | System pump - equilibration buffer 1 | Inject | In line | Selected column position | In line | Waste | First manner (mode A) FIG. 4.2 FIG. 6.2 |
| 2.1 | Sample application | Idle | System pump - sample | Inject | In line | Column Bypass | Bypass | Fractionator | Third manner (mode C) FIG. 4.4 FIG. 6.4 |
| 2.2 | Complete sample application | Idle | System pump - equilibration buffer 1 | Inject | In line | Column Bypass | Bypass | Fractionator | |
| 3 | Wash | Idle | System pump - wash buffer 1 or equilibration buffer 1 (only if equilibration buffer is same as wash buffer) | Inject | In line | Column Bypass | Bypass | Waste | |
| 4 | Elution | Sample application | System pump - elution buffer | Inject | In line | Selected column position | In line | Fractionator | First manner (mode A) FIG. 4.2 FIG. 6.2 |
| 5 | Idle | Wash | System pump - wash buffer 2 | Load | Bypass | Selected column position | In line | Waste | Second manner (mode B) |
| 6 | Idle | Elution | System pump - elution buffer 2 | Load | Bypas | Selected column position | In line | Fractionator | FIG. 4.3 FIG. 6.3 | iv) First Column is Flow-Through Mode and Second Column is Flowthrough Mode

The operator is free to install both columns at column valve;
Sample application phase of first column will overlap with the sample loading phase of second column Materials and Methods A. Chemicals, Biological Material and Chromatography Resins

| | | |
|---|---|---|
| Chemicals | 2-(N-Morpholino)ethanesulfonic Acid (MES) | Sigma-Aldrich/ Merck |
| | 2-[4-(2-Hydroxyethyl)-1-piperazinyl]-ethanesulfonic acid (HEPES) | |
| | Tris(hydroxymethyl)aminomethane (Tris) | |
| | Sodium chloride (NaCl) | |
| | Acetic acid | |
| | Hydrochloric acid (HCl) | |
| | Sodium hydroxide (NaOH) | |
| | Magnesium chloride (MgCl2) | |
| | Arginine | |
| | Ethylenediaminetetraacetic acid (EDTA) | |
| | Sodium azide | |
| Proteinase K | Roche | |
| Alpha 1 Antitrypsin reference standard | Native human alpha 1 Antitrypsin protein (Abcam) | |
| Filtered cell culture supernatant (FCCS) | Alpha 1 Antitrypsin was expressed by mammalian cell culture in Chinese hamster ovary. To remove cell debris, cell culture harvest was first centrifuged at 4000 × g for 20 min at room temperature, followed by filtration through 0.22 μm membrane (Nalgene ® Rapid-Flow Filters, Thermo Scientific). The filtered cell culture supernatant (FCCS) was then stored at 2-8° C. for short-term usage or −80° C. for long-term storage. FCCS was measured to be at approximately pH7.0 13 mS/cm. A1AT concentration and purity in FCCS varied from batch to batch. | |
| Clarified cell culture supernatant (FCCS-AC) | 150 ml of FCCS was mixed with 20 mg of Activated charcoal (Sigma-Aldrich Cat. No. 161551) per ml of sample for 4 h. Subsequent filtration was done using SartoClear CAP PC1 filter (Sartorius) and 0.22 μm membrane (Nalgene ® Rapid-Flow Filters, Thermo Scientific) FCCS was measured to be at approximately pH7.0 10 mS/cm. A1AT concentration and purity in FCCS-AC varied from batch to batch. | |
| Chromatographic resins | TOYOPEARL SuperQ-650 M (Tosoh Bio-science) TOYOPEARL NH2-750F (Tosoh Bio-science) HyperCel STAR AX (Pall) Poros XQ (Thermo Scientific) Alpha-1 Antitrypsin Select (GE Healthcare) | |

B. Experimental methods

—High Throughput Screening Plate

A 96-well filter plate with 0.2 μm hydrophilic polypropylene (GHP) pore-membrane (Pall) and 350 μl wells (Axygen) was used for screening with the help of Multi-Well Plate Vacuum Manifold (Pall). Each incubation step was performed under shaking at room temperature using rotatory shaker (Microplate Genie) at low frequency.

50 μl of working slurry (5 μl of settled resins) were transferred into each well using 12-channel pipette and the liquid was filtered off. 2×200 μl of equilibration buffer were added and incubated for 10 min. For each well, an appropriate amount of supernatant was loaded. The filter plate was then covered and incubated for 60 min or 120 min. Afterwards, a wash step was carried out with 3×200 μl of equilibration buffer and shaking for 5 min. Lastly, 2×100 μl of elution buffer were used with 10 min incubation time. The filtrate during elution was collected in a standard 96-well plate.

—Chromatography Instrumentation and Operation

Depending on the desired bed volume, chromatographic resins were packed in house using Tricorn 5 or Tricorn 10 columns (GE healthcare) and attached to ÄKTA FPLC (GE Healthcare). For conventional batch mode, a single column was connected to the column valve. As for tandem column configuration, the first column was connected to the injection valve and the second column was connected to the column valve. Column volume (CV) is defined as the volume of the column connected to column valve. pH, conductivity and UV absorbance (A280 and A254) of the solution were monitored by built-in probes in ÄKTA FPLC. In the context of tandem column configuration, CV is defined based on the volume of bind & elute column.

Generally, the column/columns was first conditioned with 5 CV of equilibration buffer to achieve desired pH and conductivity. A known amount of target protein was loaded to the column/columns via either sample pump or system pump. In order to achieve complete loading, 10 ml of wash buffer was introduced to overcome the dead volume of the system before column valve. Subsequently, 10 CV of additional wash buffer was added to help to remove the unbound material from the column.

For flow-through (FT) chromatography in which impurities were bound to the column instead of target protein, flow-through was collected. In contrast, for bind & eluate (B&E) chromatography in which the target protein bound to the column, either step or gradient elution was performed to dissociate the target protein from the column and sample was subsequently collected as a purified product. In the context of anion exchanger and affinity chromatography, proteins were eluted with increasing conductivity.

Buffers were prepared using the chemicals listed in part A. 1M HCl or 5M NaOH was used to adjust the buffer pH to the desirable condition. If required, pH of sample was adjusted using 1M Tris or 1M Acetic acid while the conductivity was lowered using MilliQ water.

—Design of Experiment (DoE) Using MODDE

For optimization of process parameters, a central composite face (CCF) design was applied using MODDE 12.1 (Umetrics). Based on the response collected, a contour plot was generated to determine the optimal operating condition.

C. Analytical Methods of Target and Impurities

—Analytical Size Exclusion Chromatography Using HPLC

| | |
|---|---|
| Column | TSK-GEL G2000SWxlcolumn (Tosoh Bio-science) |
| Flow rate | 0.6 mL/min |
| Buffer | 50 mM MES pH 6.0, 20 mM EDTA, 200 mM arginine & 0.05% Sodium azide |
| Injection volume | 50 ul |
| Calibration | UV absorbance ($A_{280}$) of known quantity (0.05, 0.10, 0.20, 0.40, 0.60, 0.80 and 1.00 mg/ml) of native human alpha 1 Antitrypsin protein (abcam) was used as calibration curve. Base on the calibration, monomeric peak at retention time of 13 to 14 min is used to quantify the amount of A1AT in the unknown sample. Any peaks appeared before the main peak are considered as high molecular weight species (HMW) while any peaks appeared after the main peak are considered as low molecular weight species (LMW). Hence, the percentage purity of main peak is calculated based on the UV absorbance of monomeric peak over UV absorbance of all peaks (FIG. 13). |

—A1AT

| | |
|---|---|
| Kit | EnzChek ™ Elastase Assay (Molecular Probes) |
| Protocol | Based on the manufacturer's protocol (for 200 µl per well)<br>1. Add 50 µl of A1AT standard or samples which ranges from 0.25 µM to 0.002 µM in final solution<br>2. Add 100 µl of 0.5 U/ml of pancreatic elastase (final concentration of 0.25 U/ml<br>3. Incubate at room temperature for 30 min<br>4. Add 50 µl of 100 µg/mL DQ elastin working solution (final concentration of 25 µg/mL)<br>5. Incubate at room temp for 30 min protected from light<br>6. Measure final fluorescence with excitation at 485 nm and emission at 530 nm |
| Background fluorescence obtained with no-enzyme control | 1. 150 µl of reaction buffer<br>2. 50 µl of 100 µg/mL DQ elastin |
| Maximal fluorescence obtained in absence of inhibitor | 1. 50 µl of reaction buffer<br>2. 100 µl of 0.5 U/ml of pancreatic elastase<br>2. 50 µl of 100 µg/mL DQ elastin |

—Residual Host Cell Proteins ELISA

| | |
|---|---|
| Kit | CHO Host Cell Proteins 3rd Generation (Cygnus Technologies) |
| Protocol | Based on the manufacturer's protocol<br>1. Add 50 µl of standards and sample<br>2. Add 100 µl of anti-CHO:HRP<br>3. Incubate at room temperature for 2 h and shake at 250 rpm<br>4. Wash each well with wash solution<br>5. Add 100 µl of TMB substrate<br>6. Incubate 30 min at room temperature<br>7. Measure final absorbance at 450/650 nm. |

—Residual DNA

| | | |
|---|---|---|
| Protein digestion | | 1. In a 0.2 ml PCR tube, add 160 µl of sample, 1.6 µl of proteinase K, 6.4 µl of MilliQ water and 8 µl of 10% v/v SDS<br>2. Incubate 16 h at 50° C.<br>3. incubate for 10 min at 95° C. |
| DNA extraction | Kit | QIAamp viral RNA Mini Kit (without addition of carrier RNA) (QIAGEN) |
| | Protocol | Based on the manufacturer's protocol<br>1. In 1.5 µl tube, add 560 µl of Buffer AVL without carrier RNA into a 1.5 ml tube and 140 µl of digested sample |

|  |  |  |
|---|---|---|
|  |  | 2. Incubate at room temperature for 10 min<br>3. Add 560 µl of isopropanol and incubate for another 10 min<br>4. Pipet 630 µl of mixture to the QIAamp Mini column and centrifuge at 14,000 rpm for 1 min; repeat this step once<br>5. Add 500 µl of Buffer AW1 and centrifuge at 14,000 rpm for 1 min<br>6. Add 500 µl of Buffer AW2 and centrifuge twice at 14,000 rpm for 3 min<br>7. Add 40 µl of MilliQ water and centrifuge at 14,000 rpm for 1 min; repeat this step once |
| DNA quantification | Kit | Quant-iT ™ PicoGreen ™ dsDNA Assay Kit (Molecular Probes) |
|  | Protocol | Based on the manufacturer's protocol<br>1. Add 100µl of standard with concentration of 50, 5, 0.5, 0.05 ng/ml and diluted sample<br>2. Add 100 µl of diluted PicoGreen reagent<br>3. Measure final fluorescence with excitation at 502 nm and emission at 523 nm |

Example 1—Unconventional Behaviour of Anion Exchange Resin, TOYOPEARL NH2 750F

Example 1.1 Abnormal Behaviour of TOYOPEARL NH2 750F with Other Anion Exchange Resins In this example, the use of various anion exchangers as a potential first flow-through column was examined. The experimental protocol is set out in the table below.

| Experimental protocol | |
|---|---|
| Method | High throughput screening (refer to the materials and methods section above)<br>70 µl of filtered cell culture supernatant (FCCS) (pH7.0, 13.43 mS/cm) containing 2.13 mg/ml of A1AT with a purity of 29.65% (by HPLC-SEC) was loaded to each well containing different types of anion exchange resins. With 60 min incubation time. |
| Purpose | To identify the performance for different types of anion exchanger |
| Equilibration buffer | 50 mM Tris pH 8.2 |
| Wash buffer | 50 mM Tris pH 8.2 |
| Elution buffer | 50 mM Tris pH 8.2 0.5 M NaCl |
| Starting material | 70 µl of filtered cell culture supernatant (FCCS) (pH7.0, 13.43 mS/cm) containing 2.13 mg/ml of A1AT with a purity of 29.65% (by HPLC-SEC) |
| Evaluation | Eluate of each condition was tested using HPLC-SEC for A1AT quantification |

Figure 8:
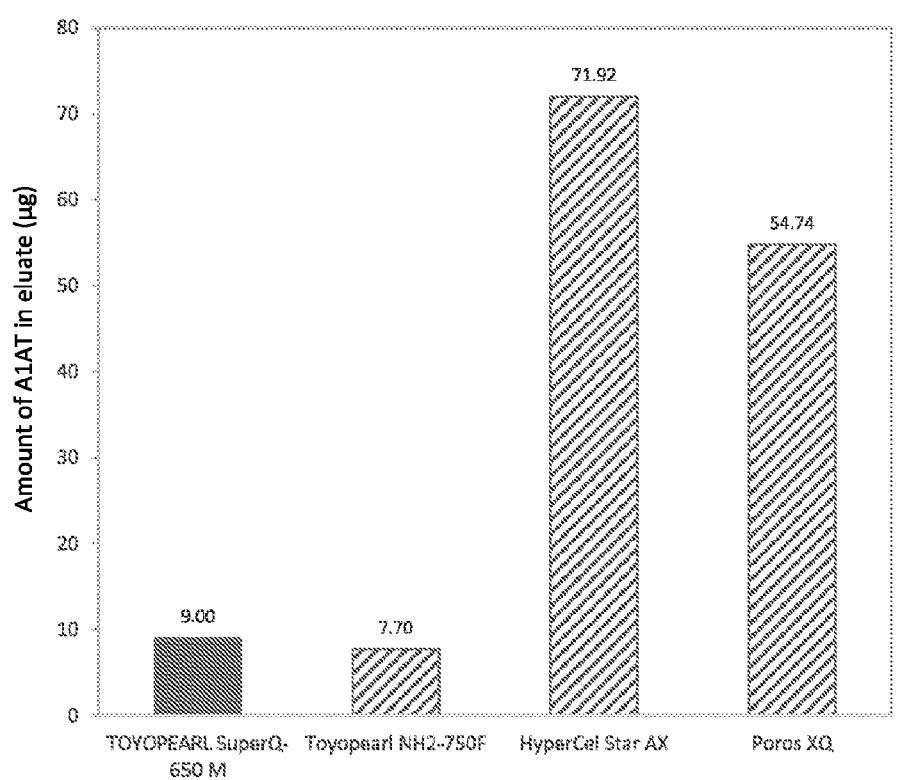
FIG. 8 shows the amount of AAT in the eluate(μg) using conventional anion exchanger (TOYOPEARL SuperQ-650 M) and high salt tolerance anion exchanger (Toyopearl NH2-750F, HyperCel Star AX and Poros XQ) in one example.

The results are shown in FIG. 8.

In general, at a binding condition with pH greater than pI of A1AT (pH 5.3), an anion exchanger is able to capture A1AT from filtered cell culture supernatant (FCCS). As FCCS has a high conductivity of 13.43 mS/cm, conventional anion exchanger such as TOYOPEARL SuperQ-650 M did not have significant binding to A1AT as conductivity is required to be equal or less than 5 mS/cm. In contrast, the high salt-tolerant anion exchangers, HyperCel Star AX and Poros XQ, were able to bind 71.92 µg and 54.7 µg of A1AT for 5 µl of resin respectively.

However, TOYOPEARL NH2-750F did not follow the trend expected for high salt-tolerant anion exchanger. At a condition suitable for anion exchanger to operate in bind & eluate mode, TOYOPEARL NH2 750F surprisingly showed a binding capacity that was even lower than conventional, non-high salt-tolerant anion exchanger. It only captured 7.70 µg of A1AT as compared to 9.00 µg by TOYOPEARL SuperQ-650 M.

Example 1.2 Performance of TOYOPEARL NH2 750F at Different Binding Conditions

An investigation was next carried out to determine whether the performance of TOYOPEARL NH2-750F is affected by conditions such as pH and conductivity.

The experimental protocol is set out in the table below.

| Experimental protocol | |
|---|---|
| Method | High throughput screening (refer to the materials and methods section above) Concentrated FCCS was spiked into each type of equilibration buffer to create 2.00 mg/ml in various binding conditions. Subsequently, 150 µl of FCCS with a purity of 63.22% (by HPLC-SEC) was loaded into respective wells with 120 min incubation time. Independent variables a) Loading amount/volume per ml of resin b) Loading pH and conductivity Fixed variable a) Loading amount/volume per ml of resin b) Quality of starting material c) Type of resin: NH2 750F Dependent variable a) Purity b) Static binding capacity per ul of resin (SBC) DoE Central composite face design consisted of a full factorial design and 2 center points (3 ^ + 2 = 11 points) |
| Purpose | To determine the performance of TOYOPEARL NH2 750F at different binding conditions of pH and conductivity |
| Equilibration buffer | 50 mM MES pH6.0, 50 mM HEPES pH7.5 or 50 mM pH9.0 Conductivity adjusted to 5, 10 or 15 mS/cm |
| Starting material | FCCS in various binding condition at a concentration of 2.00 mg/ml and 63.22% purity. |
| Evaluation | Flow-through of each condition was tested using HPLC-SEC for A1AT quantification and purity. Static binding capacity was calculated from the amount of A1AT in flow-through subtracted from the amount of A1AT loaded per µl of TOYOPEARL NH2 750F |

The results are shown in Table 8 below and FIG. 9.

TABLE 8

CCF Factors and response to evaluate the performance of TOYOPEARL NH2 750F at different binding conditions in terms of pH and conductivity TOYOPEARL NH2 750F

| Factors | | Response | |
|---|---|---|---|
| pH | Cond mS/cm | Purity % | Static Binding Capacity µg/µl |
| 6.0 | 5 | 96.22 | 10.70 |
| 6.0 | 10 | 93.81 | 11.72 |
| 6.0 | 15 | 93.57 | 4.81 |
| 7.5 | 5 | 94.12 | 25.01 |
| 7.5 | 10 | 92.28 | 8.39 |
| 7.5 | 15 | 92.65 | 10.48 |
| 9.0 | 5 | 91.15 | 7.98 |
| 9.0 | 10 | 86.38 | 4.08 |
| 9.0 | 15 | 85.05 | 0.46 |
| 7.5 | 10 | 92.82 | 12.30 |
| 7.5 | 10 | 93.06 | 11.19 |

TOYOPEARL NH2 750F showed insignificant static binding capacities of 2 to 14 µg A1AT per µl of resin at a pH condition ranging from pH 6.0 to 9.0 with conductivity ranging from 5 mS/cm to 15 mS/cm. Even at favourable conditions of high pH 7.25 and low conductivity of 5 mS/cm, TOYOPEARL NH2-750F showed an inability to bind A1AT, with an observed static binding capacity of 14 µg A1AT/µl resin. Nevertheless, it was effective in removing aggregates, giving an improvement of A1AT purity from 63.22% to 85% or to 95% depending on the binding conditions for pH ranging from 6.0 to 9.0 and conductivity below 15 mS/cm. Hence, TOYOPEARL NH2 750F is considered to operate in pseudo flow-through mode in the range of condition suggested.

In this example, conductivity below 5 mS/cm was not tested, but it is expected to give a comparable performance as that of 5 mS/cm based on the understanding of the behaviour of ion-exchange chromatography. Binding capacity is expected to increase with decreasing conductivity; thus, the resin is expected to still be effective in binding impurities at conductivity less than 5 mS/cm. The prediction given by modelling in MODDE also agrees with this assumption (see Table 9 below).

TABLE 9

Prediction for the performance of TOYOPEARL NH2-750F by MODDE

| pH | Conductivity mS/cm | Purity % | Lower % | Upper % | Static Binding Capacity µg/µl | Lower µg/µl | Upper µg/µl |
|---|---|---|---|---|---|---|---|
| | | | | | | | |

Comparing 5 mS/cm with lower conductivity of 4 mS/cm which was not tested

| pH | Cond | Purity | Lower | Upper | SBC | Lower | Upper |
|---|---|---|---|---|---|---|---|
| 6.0 | 5 | 96.24 | 94.30 | 98.17 | 11.92 | 8.19 | 15.66 |
| 6.0 | 4 | 96.58 | 94.50 | 98.65 | 12.49 | 8.45 | 16.54 |
| 7.5 | 5 | 94.69 | 93.03 | 96.35 | 14.15 | 10.29 | 18.01 |
| 7.5 | 4 | 95.03 | 93.21 | 96.85 | 14.72 | 10.50 | 18.94 |
| 9.0 | 5 | 89.23 | 87.29 | 91.17 | 7.02 | 3.28 | 10.76 |
| 9.0 | 4 | 89.57 | 87.50 | 91.65 | 7.59 | 3.54 | 11.63 |

Example 1.3 Breakthrough Curve of TOYOPEARL NIH2-750F

As TOYOPEARL NH-2 750F had limited ability to bind A1AT but was efficient in binding aggregates, further investigation was done to determine the impact of loading amount, flow rate and the quality of starting material. The experimental protocol is set out below.

| | Experimental protocol |
|---|---|
| Method | Chromatography instrumentation and operation (refer to the materials and methods section above) Using conventional batch mode with a single column connected to a column valve Independent variables a) Loading amount/ volume per ml of resin b) Flow rate c) Quality of starting material Fixed variable a) pH and conductivity: pH8.2 10 mS/cm b) Type of resin: NH2 750F Dependent variable a) HMW % which relates to purity b) Recovery which relates to binding of NH2 750F (i.e., higher binding -> greater loss at A1AT -> lower recovery) |
| Purpose | To determine the performance of TOYOPEARL NH2 750F in high molecule weight protein (HMW) removal and recovery using different starting material and different flowrate |
| Column | 1.0 ml of Toyopearl NH2-750F packed in Tricorn 5/50 column |
| Equilibration buffer | 50 mM Tris pH 8.2 10 mS/cm (75 mM NaCl) |
| Starting material | Filtered cell culture supernatant (FCCS) containing approximately 0.5 mg/ml of A1AT with HMW > 40% Clarified cell culture supernatant (FCCS-AC) containing approximately 0.5 mg/ml of A1AT with HMW > 25% |
| Evaluation | Flow-through of each condition was tested using HPLC-SEC for A1AT quantification and purity quantification |

Figure 10:
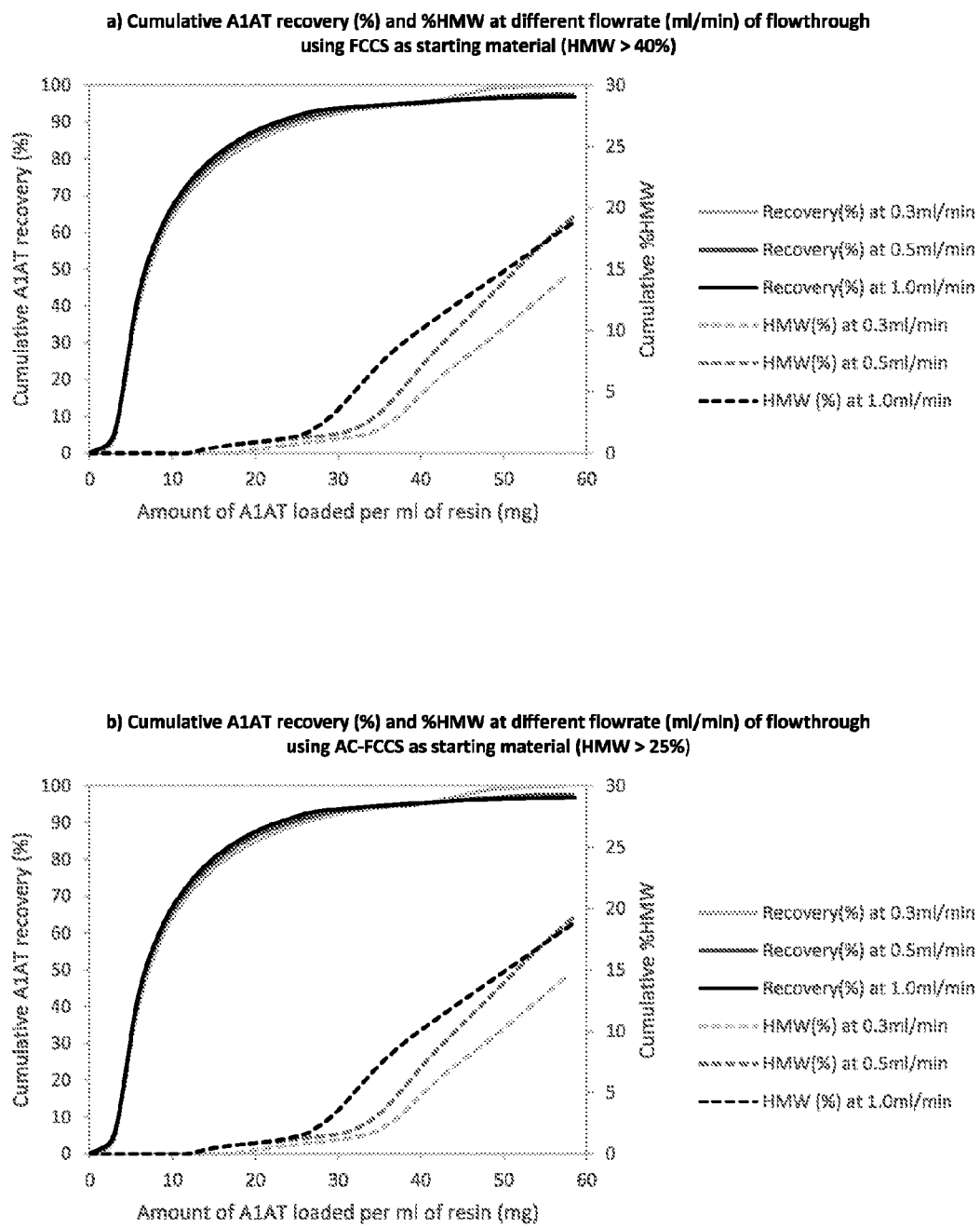
FIG. 10 shows a breakthrough curve of 1.0 ml of TOYOPEARL NH2 750F using a) filtered cell culture supernatant (FCCS) with HMW >40% and b) Clarified cell culture supernatant (FCCS-AC) with HMW >25% at different flow-rate in one example. The cumulative A1AT recovery and % HMW at different flowrate (ml/min) of flow-through are plotted.

The results are shown in FIG. 10.

In general, a trade-off relationship was observed between A1AT recovery and A1AT purity for experiments done using both FCCS and FCCS-AC as starting material. At low loading volume, more binding sites were available to capture the impurities in the supernatant. In the meantime, being an anion exchange resin, TOYOPEARL NH2 750F would also bind to A1AT concurrently, resulting in low A1AT recovery. However, with increasing loading amount per ml of resin, the loss of AAT became less significant, but the purity of A1AT was compromised. Hence, TOYOPEARL NH2 750F is considered to operate in pseudo flow-through mode at high loading volume.

Particularly for FCCS-AC, TOYOPEARL NH2 750F was able to purify a greater amount per ml of resin as compared to FCCS in flow-through mode. This is reasonable as a certain amount of impurities had been removed during activated charcoal treatment.

Depending on the purpose of purification, the requirement of purity and tolerance of process loss may differ. In the context of a capture step which prioritises recovery over purity, conditions which yield moderate or even low purity will be sufficient. For instance, to keep HMW 51.0%, 1.0 ml of TOYOPEARL NH2 750F could handle up to 22 mg of FCCS with a maximal recovery of 88.0% or 53 mg of FCCS-AC with a maximal recovery of 90.5%. On the other hand, if this method is implemented in polishing step or in the situation that no subsequent purification step will be conducted, high or moderate purity will be recommended to maximise purity within this unit operation. For instance, to keep HMW≤0.1%, the column should not be loaded with more than 12 mg of FCCS or 24 mg of FCCS-AC. This is summarized in Table 10 below.

TABLE 10

Process evaluation of various process conditions

| Purity requirement | Amount of A1AT in FCCS per ml of resin (mg) | Corresponding recovery (%) |
|---|---|---|
| High purity (HMW ≤ 0.1%) | ≤12 | ≤72.0 |
| Moderate purity (HMW ≤ 1.0%) | ≤22 | ≤88.0 |
| Low purity (HMW ≤ 10.0%) | ≤42 | ≤95.5 |

| Purity requirement | Amount of A1AT in FCCS-AC per ml of resin (mg) | Corresponding recovery (%) |
|---|---|---|
| High purity (HMW ≤ 0.1%) | ≤24 | ≤83.0 |
| Moderate purity (HMW ≤ 1.0%) | ≤53 | ≤90.5 |
| Low purity (HMW ≤ 10.0%) | ≤80 | ≤93.5 |

Validation of moderate and low purity process conditions was further explained in Example 3.

Example 2—Static Binding Capacity (SBC) of Anion Exchange Resins, TOYOPEARL SuperQ-650 M, HyperCel STAR AX & Poros XQ Since the capture step focuses on sample volume reduction, a binding & eluate column is determined to be a reasonable choice to be connected in series with a first flow-through column. Furthermore, bind & eluate chromatography also helps to separate the target protein from media components. Example 2 explained how process parameters such as pH and conductivity will affect the binding capacity of various anion exchangers operated in bind & elute mode.

| | Experimental protocol |
|---|---|
| Method | High throughput screening (refer to the materials and methods section above) Purified A1AT was concentrated and spiked into each type of equilibration buffer to create 5.00 mg/ml in various binding conditions. Subsequently, 150 μl or 300 μl of purified A1AT was loaded to respective wells with 120 min incubation time. Independent variables a) Loading pH and conductivity b) Type of resin Fixed variables a) Loading amount/ volume per ml of resin b) Quality of starting material Dependent variable a) Static binding capacity per μl of resin (SBC) DoE Central composite face design consisted of a full factorial design and 2 center points (3^2 + 2 = 11 points) For all resins, pH ranged from pH6.0 to 9.0 For conventional anion exchanger, TOYOPEARL SuperQ-650 M, lower conductivity ranged from 4 to 10 mS/cm For high salt tolerance anion exchangers, HyperCel STAR AX and Poros XQ, higher conductivity ranged from 5 to 15 mS/cm |
| Purpose | To determine the binding capacity of different resins at various loading condition |
| Starting material | 150 μl of purified A1AT at 5 mg/ml with 97.43% purity was added to each well containing TOYOPEARL SuperQ-650 M or Poros XQ 300 μl of purified A1AT at 5 mg/ml with 97.43% purity was added to each well containing HyperCel STAR AX |
| Evaluation | Eluate of each condition was tested using HPLC-SEC for A1AT quantification to determine the static binding capacity |

The results are shown in FIG. 11 and Table 11 below.

TABLE 11

CCF Factors and response to evaluate the performance of anion exchangers at different binding conditions in terms of pH and conductivity

| a) TOYOPEARL SuperQ-650 M | | | b) HyperCel STAR AX | | | c) Poros XQ | | |
|---|---|---|---|---|---|---|---|---|
| Factors | | Response | Factors | | Response | Factors | | Response |
| pH | Cond mS/cm | SBC µg/µl | pH | Cond mS/cm | SBC µg/µl | pH | Cond mS/cm | SBC µg/µl |
| 6.0 | 4 | 27.75 | 6.0 | 5 | 112.49 | 6.0 | 5 | 27.53 |
| 6.0 | 7 | 3.27 | 6.0 | 10 | 69.73 | 6.0 | 10 | 2.13 |
| 6.0 | 10 | 0.00 | 6.0 | 15 | 24.44 | 6.0 | 15 | 0.00 |
| 7.5 | 4 | 63.72 | 7.5 | 5 | 158.28 | 7.5 | 5 | 100.38 |
| 7.5 | 7 | 27.86 | 7.5 | 10 | 130.92 | 7.5 | 10 | 39.15 |
| 7.5 | 10 | 3.85 | 7.5 | 15 | 76.81 | 7.5 | 15 | 2.98 |
| 9.0 | 4 | 86.42 | 9.0 | 5 | 152.15 | 9.0 | 5 | 161.39 |
| 9.0 | 7 | 54.62 | 9.0 | 10 | 125.30 | 9.0 | 10 | 86.60 |
| 9.0 | 10 | 23.00 | 9.0 | 15 | 67.11 | 9.0 | 15 | 23.83 |
| 7.5 | 7 | 23.75 | 7.5 | 10 | 118.29 | 7.5 | 10 | 44.02 |
| 7.5 | 7 | 24.43 | 7.5 | 10 | 119.23 | 7.5 | 10 | 44.56 |

As shown in FIG. 11 and Table 11, the selected resin can bind A1AT at the various suggested conditions. Conventional anion exchanger TOYOPEARL SuperQ-650 M exhibited affinity to A1AT only at conductivity lower than 10 mS/cm with pH ranging from 6.0 to 9.0. In contrast, high salt-tolerant anion exchanger HyperCel STAR AX and Poros XQ showed affinity to A1AT at higher conductivity at 15 mS/cm and below with pH ranging from 6.0 to 9.0. As a result, high salt-tolerant anion exchangers had a wider operating range than conventional anion exchanger.

In this example, conductivity below 4 mS/cm for conventional anion exchanger or 5 mS/cm for high salt-tolerant anion exchanger was not tested. However, conductivity below 4 mS/cm is expected to give a comparable performance as that of 4 mS/cm or 5 mS/cm based on the understanding of the behaviour of ion-exchange chromatography. Binding capacity is expected to increase with decreasing conductivity; thus, the resin is expected to be still effective in binding A1AT at conductivity less than 4 mS/cm or 5 mS/cm. The prediction given by modelling in MODDE also agrees with this assumption (see Table 12 below)

TABLE 12

Prediction for the performance of TOYOPEARL SuperQ-650 M, HyperCel STAR AX, Poros XQ by MODDE

| | pH | Conductivity mS/cm | Static Binding Capacity µg/µl | Lower µg/µl | Upper µg/µl |
|---|---|---|---|---|---|
| Comparing of 4 mS/cm or 5 mS/cm with lower conductivity of 3 mS/cm or 4 mS/cm which was not tested | | | | | |
| TOYOPEARL SuperQ-650 M | 6.0 | 4 | 24.87 | 12.65 | 37.09 |
| | 6.0 | 3 | 30.29 | 15.42 | 45.16 |
| | 7.5 | 4 | 55.96 | 48.41 | 63.51 |
| | 7.5 | 3 | 64.35 | 55.09 | 73.61 |
| | 9.0 | 4 | 87.05 | 74.83 | 99.27 |
| | 9.0 | 3 | 98.41 | 83.54 | 113.28 |
| HyperCel STAR AX | 6.0 | 5 | 111.31 | 100.22 | 122.40 |
| | 6.0 | 4 | 119.80 | 107.92 | 131.67 |
| | 7.5 | 5 | 163.13 | 153.64 | 172.63 |
| | 7.5 | 4 | 171.62 | 161.21 | 182.02 |
| | 9.0 | 5 | 157.28 | 146.19 | 168.37 |
| | 9.0 | 4 | 165.77 | 153.89 | 177.64 |

TABLE 12-continued

Prediction for the performance of TOYOPEARL SuperQ-650 M, HyperCel STAR AX, Poros XQ by MODDE

| | pH | Conductivity mS/cm | Static Binding Capacity µg/µl | Lower µg/µl | Upper µg/µl |
|---|---|---|---|---|---|
| Poros XQ | 6.0 | 5 | 24.30 | 10.58 | 38.01 |
| | 6.0 | 4 | 27.54 | 12.07 | 43.01 |
| | 7.5 | 5 | 92.16 | 83.69 | 100.64 |
| | 7.5 | 4 | 100.91 | 91.30 | 110.52 |
| | 9.0 | 5 | 160.03 | 146.31 | 173.75 |
| | 9.0 | 4 | 174.28 | 158.81 | 189.75 |

Unlike affinity resin, the binding capacity of anion exchange resin was found to be affected by pH and conductivity. This example provides an indication of the appropriate working range of TOYOPEARL SuperQ-650 M, HyperCel STAR AX and Poros XQ.

Example 3—Purification of Filtered Cell Culture Supernatant (FCCS) and Clarified FCCS (FCCS-AC) Using TOYOPEARL NH2 750F in Series with HyperCel Star AX Example 3 examines how process parameters such as loading amount and quality of starting material may affect performance when using TOYOPEARL NH2 750F in series with HyperCel STAR AX. The experimental protocol is set out in the table below.

| | Experimental protocol |
|---|---|
| Method | Chromatography instrumentation and operation (refer to the materials and methods section above) Using a tandem column configuration with the first column connected to an injection valve and the second column connected to a column valve Independent variables a) Quality of starting material b) Loading amount/ volume per ml of resin Fixed variable a) Type of resin: TOYOPEARL NH2 750F & HyperCel STAR AX |

| | Experimental protocol |
|---|---|
| | b) Loading pH & conductivity |
| | Dependent variables |
| | a) Recovery |
| | b) Purity |
| Purpose | To evaluate the performance of tandem column configuration using different starting material and different volume of TOYOPEARL NH2-750F |
| Evaluation | Eluate of each experiment was tested on SEC-HPLC and residual HCP ELISA |

Table 13 below summarizes the different configurations used.

TABLE 13

Experimental conditions for various configuration of tandem chromatography FCCS

| Valve: Name of column (size) | | Experimental conditions |
|---|---|---|
| Injection valve: #1 TOYOPEARL NH2-750F (0.6 ml) or #2 TOYOPEARL NH2-750F (1.0 ml) Column valve: HyperCel STAR AX (1.0 ml) | Equilibration buffer | 50 mM Tris pH 8.2 10 mS/cm (75 mM NaCl) |
| | Wash buffer | 50 mM Tris pH 8.2 10 mS/cm (75 mM NaCl) |
| | Elution buffer | 10CV gradient elution to 50 mM Tris pH 8.2 1M NaCl |
| | Flowrate | 0.5 ml/min |
| | Sample | ~20 mg filtered cell culture supernatant (FCCS) titrated to pH 8.2 10 mS/cm |
| Injection valve: #3 TOYOPEARL NH2-750F (0.3 ml) or #4 TOYOPEARL NH2-750F (0.6 ml) Column valve: HyperCel STAR AX (1.0 ml) | Equilibration buffer | 50 mM Tris pH 8.2 10 mS/cm (75 mM NaCl) |
| | Wash buffer | 50 mM Tris pH 8.2 10 mS/cm (75 mM NaCl) |
| | Elution buffer | 10CV gradient elution to 50 mM Tris pH 8.2 1M NaCl |
| | Flowrate | 0.5 ml/min |
| | Sample | ~20 mg clarified cell culture supernatant (FCCS-AC) titrated to pH 8.2 10 mS/cm |

The results are shown in Table 14 and FIG. 12.

TABLE 14

Purification table of for various configuration of tandem chromatography FCCS or FCCS-AC

| | A1AT Conc mg/ml | HMW % | Monomer % | LMW % | Vol ml | A1AT mg | Recovery % | HCP ppm | HCP removal Fold reduction |
|---|---|---|---|---|---|---|---|---|---|
| Filtered cell culture supernatant (FCCS) | 1.68 | 47.98 | 41.66 | 10.36 | | | | 240,061 | |
| Purified sample from Experiment #1 (0.6 ml TOYOPEARL NH2-750F) | 3.72 | 6.34 | 89.82 | 3.83 | 6.15 | 22.90 | 100.54 | 42,035 | 5.71 |
| Purified sample from Experiment #2 (1.0 ml TOYOPEARL NH2-750F) | 4.51 | 1.44 | 98.18 | 0.38 | 4.30 | 19.40 | 88.18 | 33,982 | 7.06 |
| Clarified cell culture supernatant (FCCS-AC) | 0.80 | 11.57 | 88.43 | 0 | | | 89.33 | 10,172 | |
| Purified sample from Experiment #3 (0.3 ml TOYOPEARL NH2-750F) | 4.82 | 1.40 | 98.60 | 0 | 3.87 | 18.66 | 87.02 | 421 | 24.15 |
| Purified sample from Experiment #4 (0.5 ml TOYOPEARL NH2-750F) | 5.13 | 0.39 | 99.61 | 0 | 3.57 | 18.31 | 84.79 | 352 | 28.89 |

With single unit operation using 0.6 ml of TOYOPEARL NH2 750F (i.e. 37.97 mg A1AT/ml resin) in series with 1.0 ml of HyperCel STAR AX to purify FCCS, the purity of eluate improved from 41.66% to 89.82% and residual HCP reduction from 240,061 ppm to 42,035 ppm. When the volume of TOYOPEARL NH2 750F increased to 1.0 ml (i.e. 22.00 mg A1AT/ml resin), the eluate had higher purity of 98.18% and residual HCP of 33,982 ppm. However, the recovery dropped from 100.54% to 88.18%, which correlated to the conclusion drawn from Example 1.

The tandem column configuration was also effective when applied to FCCS-AC. With single unit operation using 0.3 ml of TOYOPEARL NH2 750F (i.e. 71.46 mg A1AT/ml resin) in series with 1.0 ml of HyperCel STAR AX, the purity of eluate improved from 88.43% to 98.60% and residual HCP reduction from 10,172 ppm to 421 ppm. When the volume of TOYOPEARL NH2 750F increased to 0.5 ml (i.e. 43.19 mg A1AT/mi resin), the eluate had higher purity of 99.61% and residual HCP of 351 ppm. Similarly, the recovery decreased from 87.02% to 84.79%.

Figure 13:
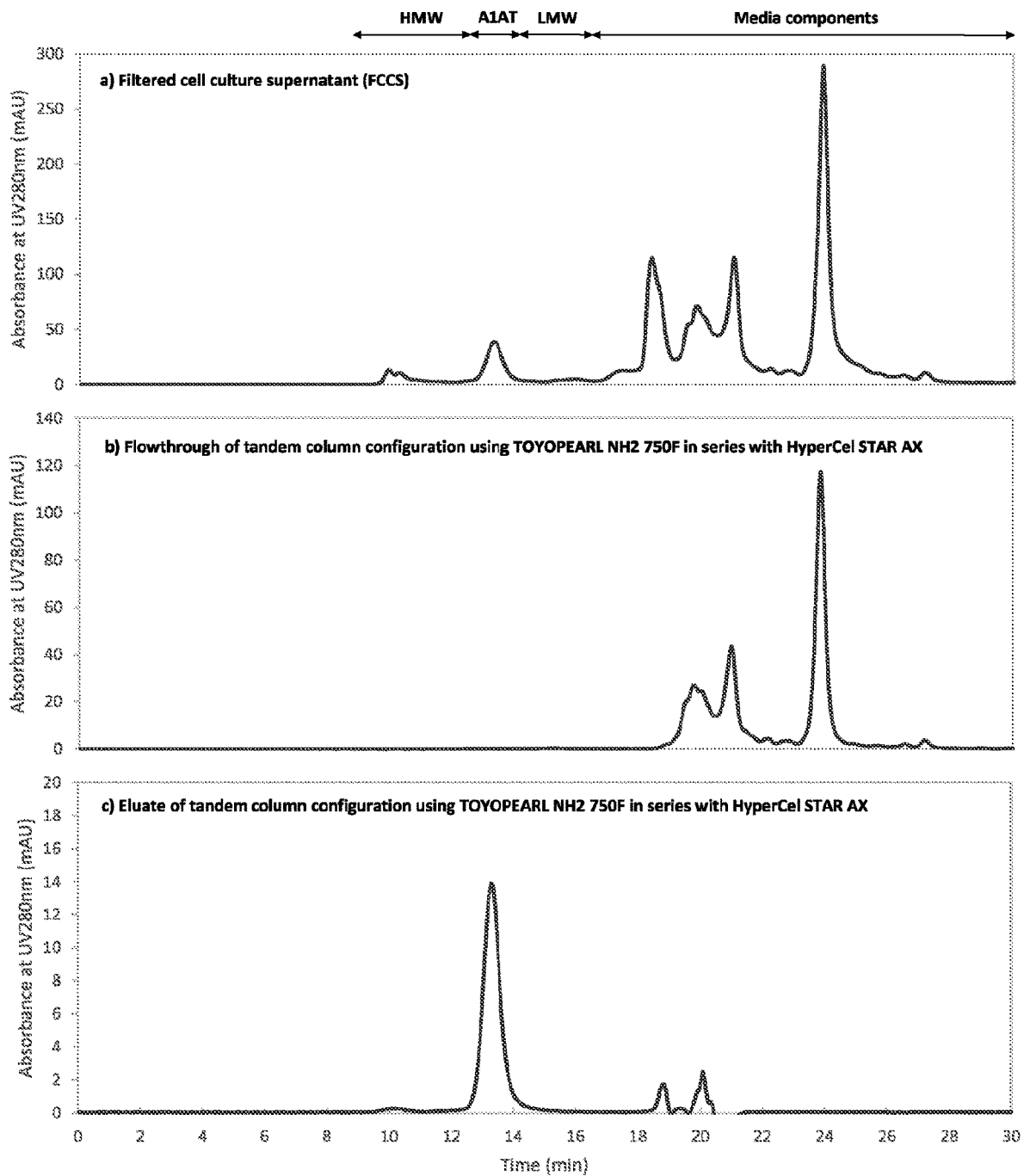
FIG. 13 shows the HPLC-SEC analysis results of a) filtered cell culture supernatant (FCCS), b) flow-through and c) eluate of tandem column configuration using TOYOPEARL NH2 750F in series with HyperCel STAR AX in one example.

Chromatographs of HPLC-SEC were summarized on FIG. 13, indicating the improvement of A1AT monomeric purity before and after purification using tandem column chromatography.

Example 4—Purification of Filtered Cell Culture Supernatant (FCCS) and Clarified FCCS (FCCS-AC) Using Different Combinations of Tandem Columns Example 4 explores different potential combinations of tandem columns. In particular, the application of conventional anion exchange resin (TOYOPEARL SuperQ-650 M), high salt-tolerant anion exchange resin (HyperCel STAR AX & Poros XQ) or affinity resin (Alpha-1 Antitrypsin Select) as second chromatography column was studied. The experimental protocol is set out in the table below.

| | Experimental protocol |
|---|---|
| Method | Chromatography instrumentation and operation (refer to the materials and methods section above) Using a tandem column configuration with the first column connected to the injection valve and the second column connected to the column valve |
| Purpose | To evaluate the performance of tandem column configuration using different selections of the second column |
| Evaluation | Eluate of each experiment was tested on SEC-HPLC and residual HCP ELISA and DNA assay |

FCCS with pH 7.0 at 13 mS/cm and FCCS-AC with pH 7.0 at 10 mS/cm were used. Therefore, in this example, 5.0 mS/cm was further validated for TOYOPEARL SuperQ-650 M to minimise sample dilution while maximising binding capacity at pH9.0. As dilution of the sample would increase processing time in the sample application phase, minimal sample dilution is preferred. Similarly, 10 mS/cm was validated for high salt-tolerant anion exchangers with optimal pH8.2 for HyperCel STAR AX and pH9.0 for Poros XQ. Nevertheless, it is understood that the operating condition is not limited to the validated conditions.

Based on modelling done in Example 1 and 2, a prediction was made to evaluate the suitability of the selected conditions. As summarized in Tables 15 and 16 below, the selected condition was able to achieve purity above 85%. In addition, the static binding capacity of TOYOPEARL NH2 750F was significantly lower than that of TOYOPEARL SuperQ-650 M, HyperCel STAR AX and Poros XQ. Hence, the process loss of AAT would be minimized.

TABLE 15

Prediction of TOYOPEARL NH2 750F as first chromatography column operated in flow-through mode based on modelling done in Example 1.2

| pH | Conductivity mS/cm | Purity % | Lower % | Upper % | Static Binding Capacity µg/µl | Lower µg/µl | Upper µg/µl |
|---|---|---|---|---|---|---|---|
| 9.0 | 5 | 89.23 | 87.29 | 91.17 | 7.02 | 3.28 | 10.76 |
| 8.2 | 10 | 90.93 | 89.81 | 92.04 | 9.14 | 6.84 | 11.44 |
| 9.0 | 10 | 87.53 | 85.95 | 89.11 | 4.17 | 1.24 | 7.10 |
| 7.4 | 10 | 93.21 | 91.99 | 94.43 | 11.45 | 8.85 | 14.04 |

TABLE 16

Prediction of TOYOPEARL SuperQ-650 M, HyperCel STAR AX or Poros XQ as second chromatography column operated in bind & elute mode based on modelling done in Example 2

| | pH | Conductivity mS/cm | Static Binding Capacity µg/µl | Lower µg/µl | Upper µg/µl |
|---|---|---|---|---|---|
| TOYOPEARL SuperQ-650 M | 9.0 | 5 | 75.69 | 65.78 | 85.59 |
| HyperCel STAR AX | 8.2 | 10 | 125.15 | 118.75 | 131.55 |
| Poros XQ | 9.0 | 10 | 88.78 | 80.30 | 97.25 |

As the static mode is representative of dynamic mode to a limited extent, further validation was done based on the condition listed in Table 17 below.

TABLE 17

Experimental conditions for various combination of tandem chromatography FCCS or FCCS-AC

| Valve: Name of column (size) | Experimental conditions | |
|---|---|---|
| Injection valve: #1 TOYOPEARL NH2-750F (1.0 ml) for FCCS or #4 TOYOPEARL NH2-750F (0.5 ml) for FCCS-AC Column valve: HyperCel STAR AX (1 ml) | Equilibration buffer | 50 mM Tris pH 8.2 10 mS/cm (75 mM NaCl) |
| | Wash buffer | 50 mM Tris pH 8.2 10 mS/cm (75 mM NaCl) |
| | Elution buffer | 10CV gradient elution to 50 mM Tris pH 8.2 1M NaCl |
| | Flowrate | 0.5 ml/min |
| | Sample | ~20 mg FCCS or FCCS-AC titrated to pH 8.2 10 mS/cm |
| Injection valve: #2 TOYOPEARL NH2-750F (1.0 ml) for FCCS or #5 TOYOPEARL NH2-750F (0.5 ml) for FCCS-AC Column valve: TOYOPEARL SuperQ-650 M (1 ml) | Equilibration buffer | 50 mM Tris pH 9.0 5 mS/cm (30 mM NaCl) |
| | Wash buffer | 50 mM Tris pH 9.0 5 mS/cm (30 mM NaCl) |
| | Elution buffer | 10CV gradient elution to 50 mM Tris pH 9.0 1M NaCl |
| | Flowrate | 0.5 ml/min |
| | Sample | ~20 mg FCCS or FCCS-AC titrated to pH 9.0 5 mS/cm |
| Injection valve: #3 TOYOPEARL NH2-750F (1.0 ml) for FCCS or #6 TOYOPEARL NH2-750F (0.5 ml) for FCCS-AC Column valve: Poros XQ (1 ml) | Equilibration buffer | 50 mM Tris pH 9.0 10 mS/cm (75 mM NaCl) |
| | Wash buffer | 50 mM Tris pH 9.2 10 mS/cm (75 mM NaCl) |
| | Elution buffer | 10CV gradient elution to 50 mM Tris pH 9.0 1M NaCl |
| | Flowrate | 0.5 ml/min |
| | Sample | ~20 mg FCCS or FCCS-AC titrated to pH 9.0 10 mS/cm |
| Injection valve: #4 TOYOPEARL NH2-750F (1.0 ml) for FCCS or #8 TOYOPEARL NH2-750F (0.5 ml) for FCCS-AC Column valve: Alpha-1 Antitrypsin Select (4 ml) | Equilibration buffer | 20 mM Tris pH 7.4 10 mS/cm (75 mM NaCl) |
| | Wash buffer | 50 mM Tris pH 7.4 10 mS/cm (75 mM NaCl) |
| | Elution buffer | 10CV gradient elution to 2 mM Tris pH 7.4 2M MgCl2 |

TABLE 17-continued

Experimental conditions for various combination of tandem chromatography FCCS or FCCS-AC

| Valve: Name of column (size) | Experimental conditions |
|---|---|
| Flowrate | 0.5 ml/min |
| Sample | ~20 mg FCCS or FCCS-AC titrated to pH 7.4 10 mS/cm |

Figure 15:
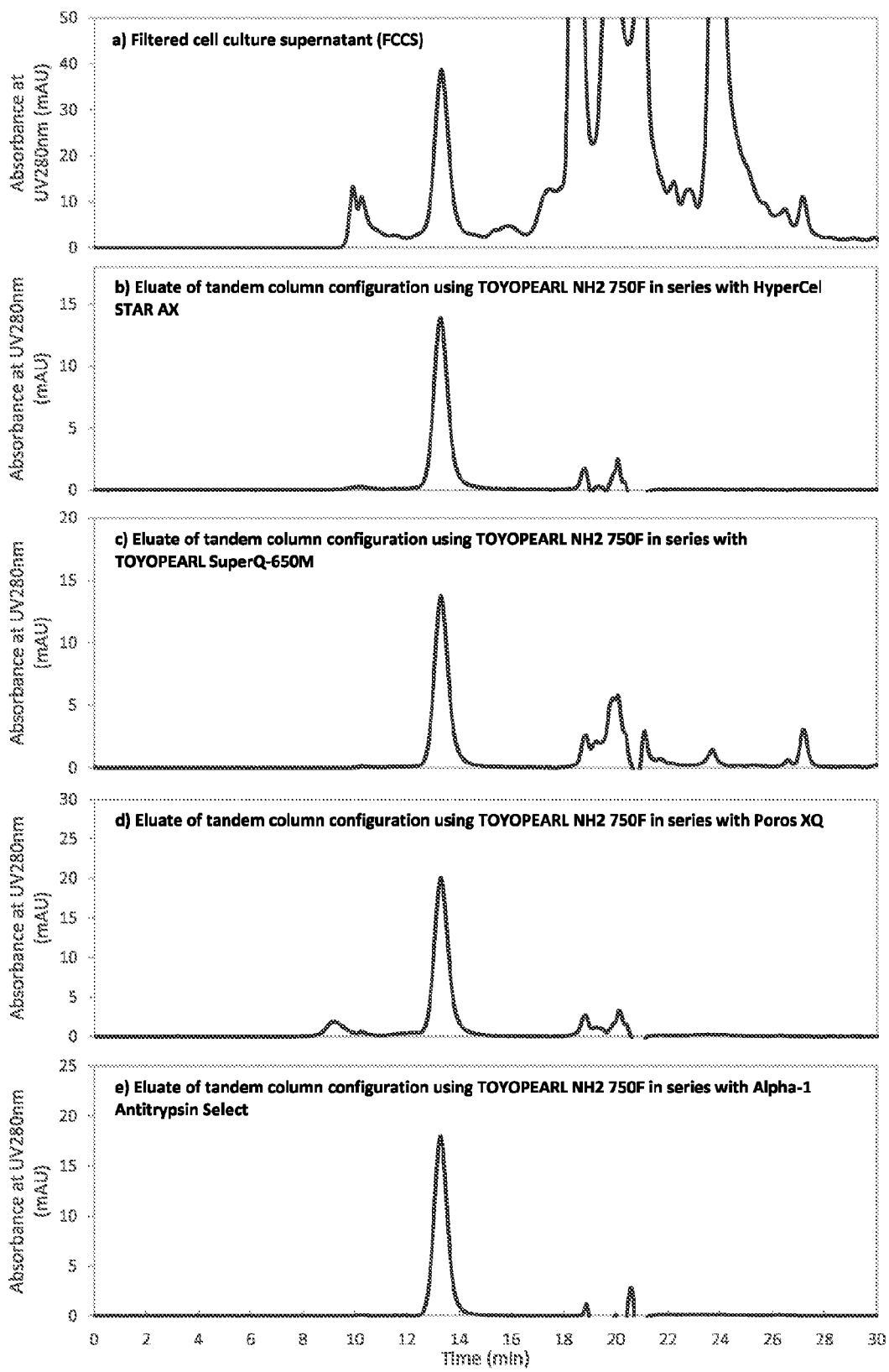
FIG. 15 shows the HPLC-SEC analysis results of a) filtered cell culture supernatant and eluate of tandem column configuration using TOYOPEARL NH2 750F in series with b) HyperCel STAR AX, c) TOYOPEARL SuperQ-650M, d) Poros XQ and e) Alpha-1 Antitrypsin Select in one example.
Figure 16:
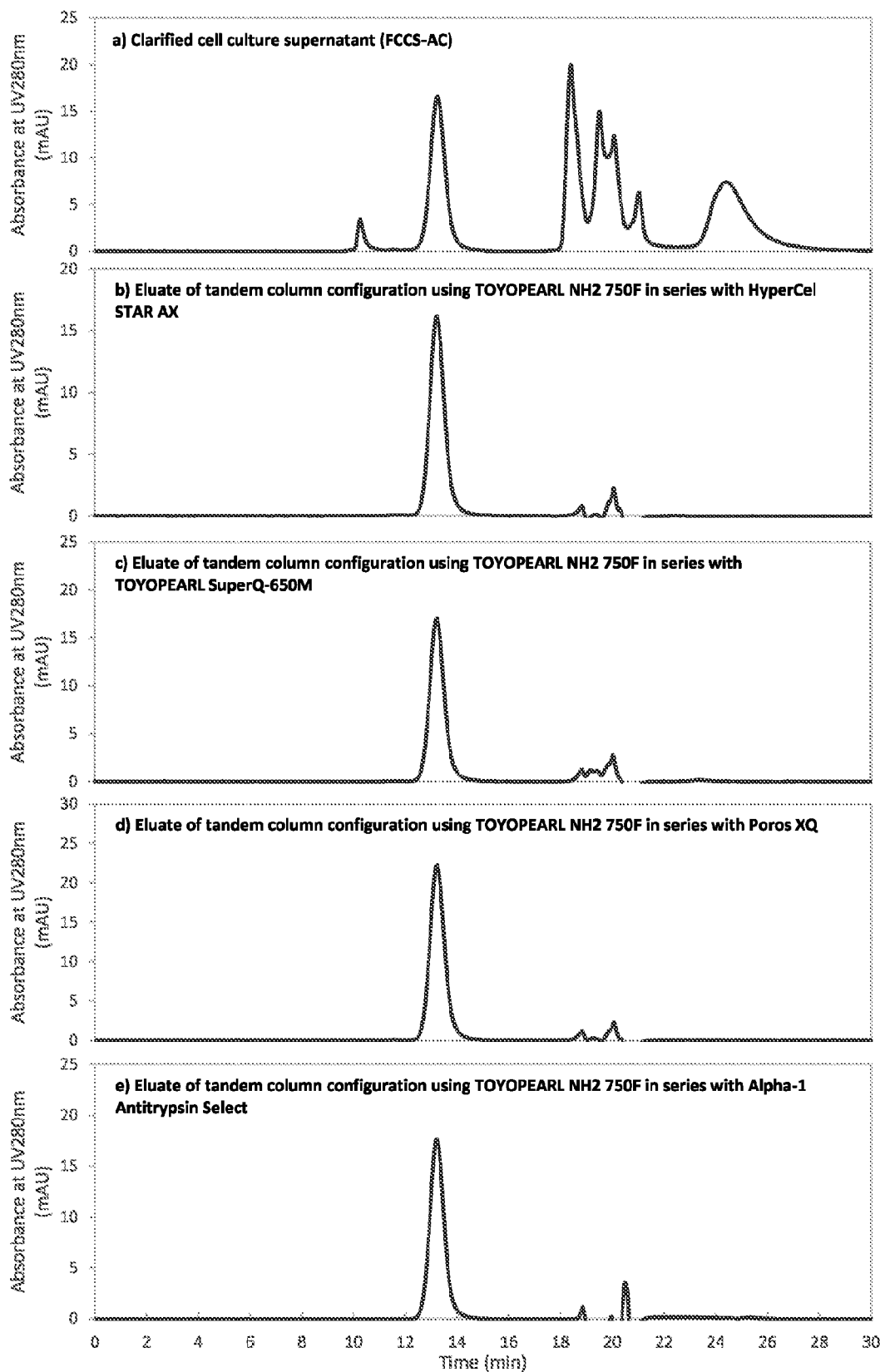
FIG. 16 shows the HPLC-SEC analysis results of a) clarified cell culture supernatant, and eluate of tandem column configuration using TOYOPEARL NH2 750F in series with b) HyperCel STAR AX, c) TOYOPEARL SuperQ-650M, d) Poros XQ and e) Alpha-1 Antitrypsin Select in one example.
Figure 17:
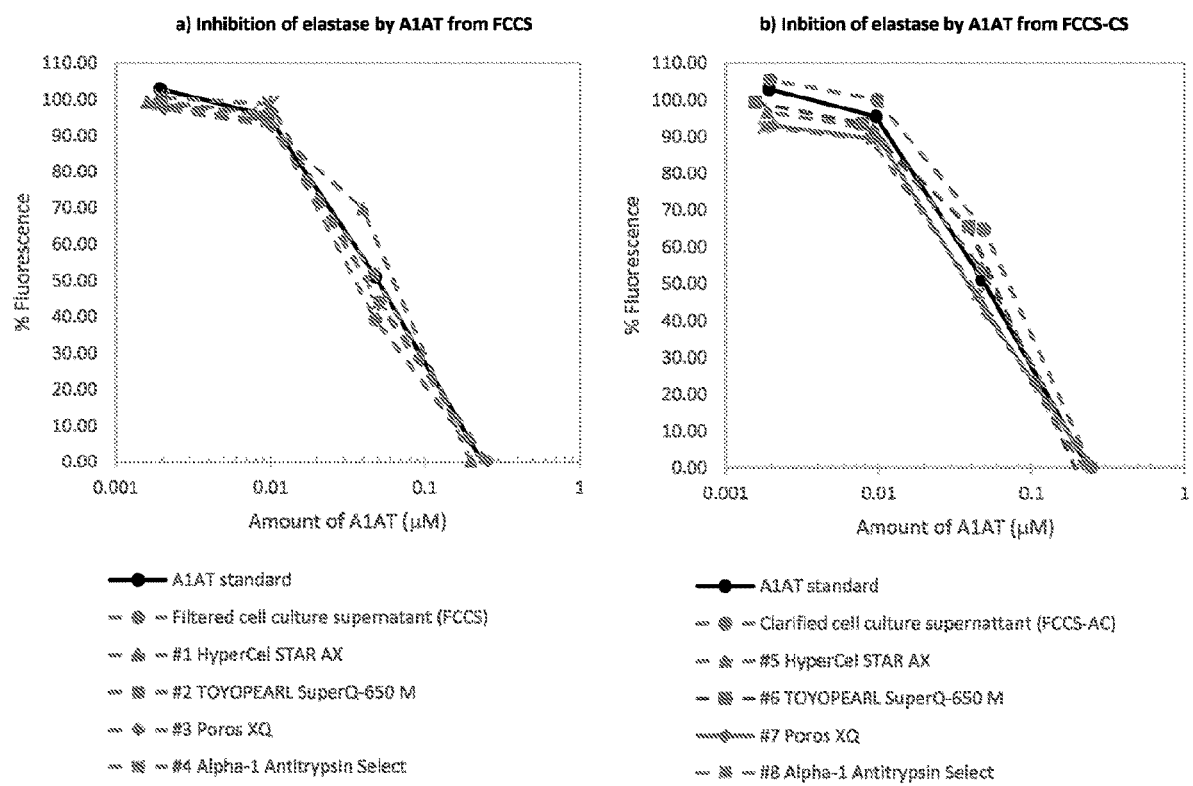
FIG. 17 shows the inhibition of elastase by A1AT from a) filtered cell culture supernatant (FCCS) and b) clarified cell culture supernatant (FCCS-AC) in one example. All values were adjusted for background fluorescence with 25 μg/ml of DQ elastin. The final fluorescence percentage was calculated based on fluorescence obtained in the absence of inhibitor with 0.25 U/ml of pancreatic elastase and 25 μg/ml of DQ elastin.

The results are shown in Table 18 and FIGS. 14-16.

TABLE 18

Purification table for various combination of tandem chromatography FCCS or FCCS-AC

| | A1AT Conc mg/ml | HMW % | Monomer % | LMW % | Vol ml | A1AT mg | Recovery % | HCP ppm | HCP removal Fold reduction | DNA ppb | DNA removal Fold reduction |
|---|---|---|---|---|---|---|---|---|---|---|---|
| Filtered cell culture supernatant (FCCS) | 2.01 | 28.30 | 56.13 | 15.58 | | | | 207,297 | | 1,848,783 | |
| Purified sample from Experiment #1 (HyperCel STAR AX) | 4.13 | 2.62 | 97.38 | — | 4.10 | 16.95 | 83.79 | 41,639 | 4.98 | 10,874 | 170.01 |
| Purified sample from Experiment #2 (TOYOPEARL SuperQ-650 M) | 2.43 | 1.83 | 98.17 | — | 7.35 | 17.88 | 86.27 | 40,892 | 5.07 | 11,155 | 165.74 |
| Purified sample from Experiment #3 (Poros XQ) | 3.55 | 15.27 | 84.41 | 0.32 | 5.50 | 19.54 | 96.23 | 37,513 | 5.53 | 36,924 | 50.07 |
| Purified sample from Experiment #4 (Alpha-1 Antitrypsin Select) | 1.49 | 0.62 | 99.38 | — | 11.81 | 17.54 | 86.80 | 811 | 255.56 | 32,771 | 56.41 |
| Clarified cell culture supernatant (FCCS-AC) | 1.02 | 10.87 | 87.90 | 1.23 | | | | 10,816 | | 37,489 | |
| Purified sample from Experiment #5 (HyperCel STAR AX) | 4.86 | 0.34 | 99.66 | — | 3.65 | 17.75 | 83.64 | 427 | 25.35 | 2,059 | 18.21 |
| Purified sample from Experiment #6 (TOYOPEARL SuperQ-650 M) | 4.05 | 0.23 | 99.77 | — | 3.53 | 14.31 | 75.64 | 486 | 22.25 | 2,745 | 13.66 |
| Purified sample from Experiment #7 (Poros XQ) | 5.32 | 0.56 | 99.44 | — | 3.30 | 17.56 | 84.14 | 472 | 22.94 | 1,872 | 20.02 |
| Purified sample from Experiment #8 (Alpha-1 Antitrypsin Select) | 1.55 | 0.14 | 99.86 | — | 10.91 | 16.86 | 80.11 | 9 | 1235.13 | 7,968 | 4.71 |

With the appropriate operating condition, tandem column configuration was able to work on different combinations of the second bind & elute columns such as HyperCel STAR AX, TOYOPEARL SuperQ-650 M, Poros XQ or Alpha-1 Antitrypsin Select. For conventional or high salt-tolerant anion exchanger, the operating conditions were selected based on the static binding capacity explained in Example 2. As for affinity chromatography, the conditions were based on the manufacturer's recommendation as it was less affected by pH and conductivity.

A1AT activity before and after purification was further determined by inhibition of pancreatic elastase. From FIG.

17, purification did not adversely alter the activity of A1AT as no significant reduction of elastase inhibition was observed for A1AT purified using different combinations of tandem columns. 50% inhibition of 0.25 U/ml elastase could be achieved using >0.06 μM of A1AT added.

Example 5—Comparative Study 1: Effect of Tandem Column Configuration on Effective Dynamic Binding Capacity (DBC) of Anion Exchanger The performance of a tandem column configuration was compared against that of single column configuration in this example. The experimental protocol is set out in the table below.

| | Experimental protocol |
|---|---|
| Method | Chromatography instrumentation and operation (refer to the materials and methods section above) Single column installed on column valve Or Using tandem column configuration with the first column connected to the injection valve and the second column connected to the column valve |
| Purpose | To evaluate the performance of tandem column configuration |
| Evaluation | Flowthrough of each condition was tested using HPLC-SEC for A1AT quantification and purity quantification |

The experimental conditions used are laid out in Table 19 below.

TABLE 19

Experimental conditions for binding efficiency evaluation

| Configuration | Valve: Name of column (size) | Experimental conditions | |
|---|---|---|---|
| Single anion exchange column in conventional batch mode | Column valve: HyperCel STAR AX (1 ml) | Equilibration buffer Flowrate | 50 mM Tris pH 8.2 12.5 mS/cm (100 mM NaCl) 0.3 ml/min |
| Tandem columns | Injection valve: TOYOPEARL NH2-750F (2 ml) Column valve: HyperCel STAR AX (1 ml) | Equilibration buffer Flowrate | 50 mM Tris pH 8.2 12.5 mS/cm (100 mM NaCl) 0.3 ml/min |

Figure 18:
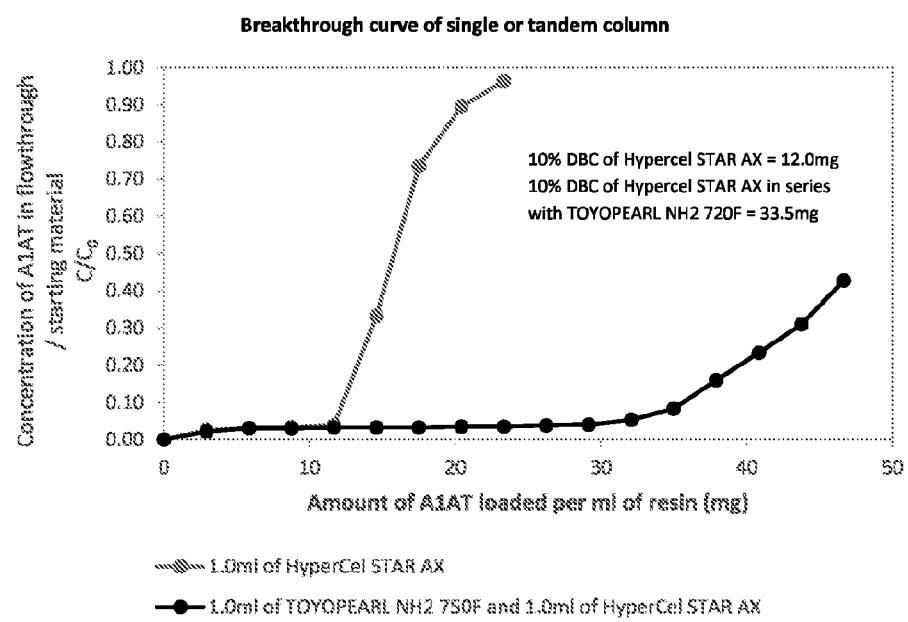
FIG. 18 shows the breakthrough curve of single anion exchange column vs two anion exchange columns in series in one example.

The results are shown in FIG. 18.

Typically, the dynamic binding capacity of anion exchanger is constant under the same binding condition. As discussed previously, anion exchange chromatography has low selectivity such that it will bind to negatively charged impurities such as host cell proteins and DNA. Pre-treatment to remove impurities by the first column in tandem configuration helps to fully utilise the binding sites in the second column to capture target protein. Therefore, a significant increase in effective binding capacity of target protein was achieved, resulting in improved productivity. From FIG. 18, 1.0 ml of HyperCel STAR AX had an effective dynamic binding capacity (10% breakthrough) of 12.0 mg A1AT. However, when TOYOPEARL NH2 720F was placed upstream, effective DBC increased to 33.5 mg A1AT. Hence, the productivity per cycle of the tandem column was 2.79 times greater than that of the single column.

To match the yield achieved by 1.0 ml TOYOPEARL NH2 720F and 1.0 ml HyperCel STAR AX, conventional batch mode with single column would require 3 cycles of 1.0 ml HyperCel STAR AX, 1 cycle of 3.0 ml HyperCel STAR AX or 1 cycle of 1.0 ml TOYOPEARL NH2 750F followed by 1 cycle of 1.0 ml HyperCel STAR AX. This will result in longer processing duration or higher consumable cost. In contrast, the tandem configuration has better utilisation of resin or shorter processing time with an amalgamation of 2 purification steps. Hence, this method would advantageously lead to higher productivity and reduction of production cost. The shortcomings of single column configuration against tandem column configuration are summarized in Table 20 below.

TABLE 20

Potential disadvantages of conventional batch mode process with a single column

| Conventional batch mode (To match with 1.0 ml TOYOPEARL NH2 720F and 1.0 ml HyperCel STAR AX) | Potential disadvantage as compared to the present method |
|---|---|
| 3 cycles of 1.0 ml HyperCel STAR AX | Longer processing duration |
| 1 cycle of 3.0 ml HyperCel STAR AX | Higher consumable cost; May face hardware restriction when the largest column available is not sufficient to process 1 batch of drug |
| 1 cycle of 1.0 ml TOYOPEARL NH2 750F followed by 1 cycle of 1.0 ml HyperCel STAR AX | Longer processing duration |

Example 6—Comparative Study 2: Comparison with Conventional Purification Methods in a Single Unit Operation In this example, a tandem configuration is further compared with a single column affinity chromatography using conventional batch mode and anion exchange chromatography using conventional batch mode. The experimental protocol is set out in the table below.

| | Experimental protocol |
|---|---|
| Method | Chromatography instrumentation and operation (refer to the materials and methods section above) Single column installed on column valve Or Using a tandem column configuration with the first column connected to the injection valve and the second column connected to the column valve |
| Purpose | To evaluate the performance of a single unit operation |
| Evaluation | Eluate of each condition was tested using HPLC-SEC for A1AT quantification and purity quantification and ELISA for residual HCP |

The experimental conditions employed are laid out in Table 21 below.

TABLE 21

Experimental conditions for different configuration of single unit operation using FCCS

| Configuration | Valve: Name of column (size) | Experimental conditions and results | |
|---|---|---|---|
| Affinity chromatography (AC) using conventional batch mode | Column valve: Alpha-1 Antitrypsin Select (1.0 ml) | Equilibration buffer | 50 mM Tris pH 8.2 12.5 mS/cm (100 mM NaCl) |
| | | Elution buffer | 50 mM Tris pH 8.2 2M MgCl2 |
| | | Flowrate | 0.3 ml/min |
| | | Sample | ~8 mg of filtered cell culture supernatant (FCCS) at pH 8.2 12.5 mS/cm |
| Anion exchange chromatography (HC) using conventional batch mode | Column valve: HyperCel STAR AX (1.0 ml) | Equilibration buffer | 50 mM Tris pH 8.2 12.5 mS/cm (100 mM NaCl) |
| | | Elution buffer | 50 mM Tris pH 8.2 1M NaCl |
| | | Flowrate | 0.3 ml/min |
| | | Sample | ~10 mg of filtered cell culture supernatant (FCCS) at pH 8.2 12.5 mS/cm |
| Tandem column using anion exchange chromatography (AXTC) | Injection valve: TOYOPEARL NH2-750F (2.0 ml) Column valve: HyperCel STAR AX (1.0 ml) | Equilibration buffer | 50 mM Tris pH 8.2 12.5 mS/cm (100 mM NaCl) |
| | | Elution buffer | 50 mM Tris pH 8.2 1M NaCl |
| | | Flowrate | 0.3 ml/min |
| | | Sample | ~30 mg of filtered cell culture supernatant (FCCS) at pH 8.2 12.5 mS/cm |

Figure 19:
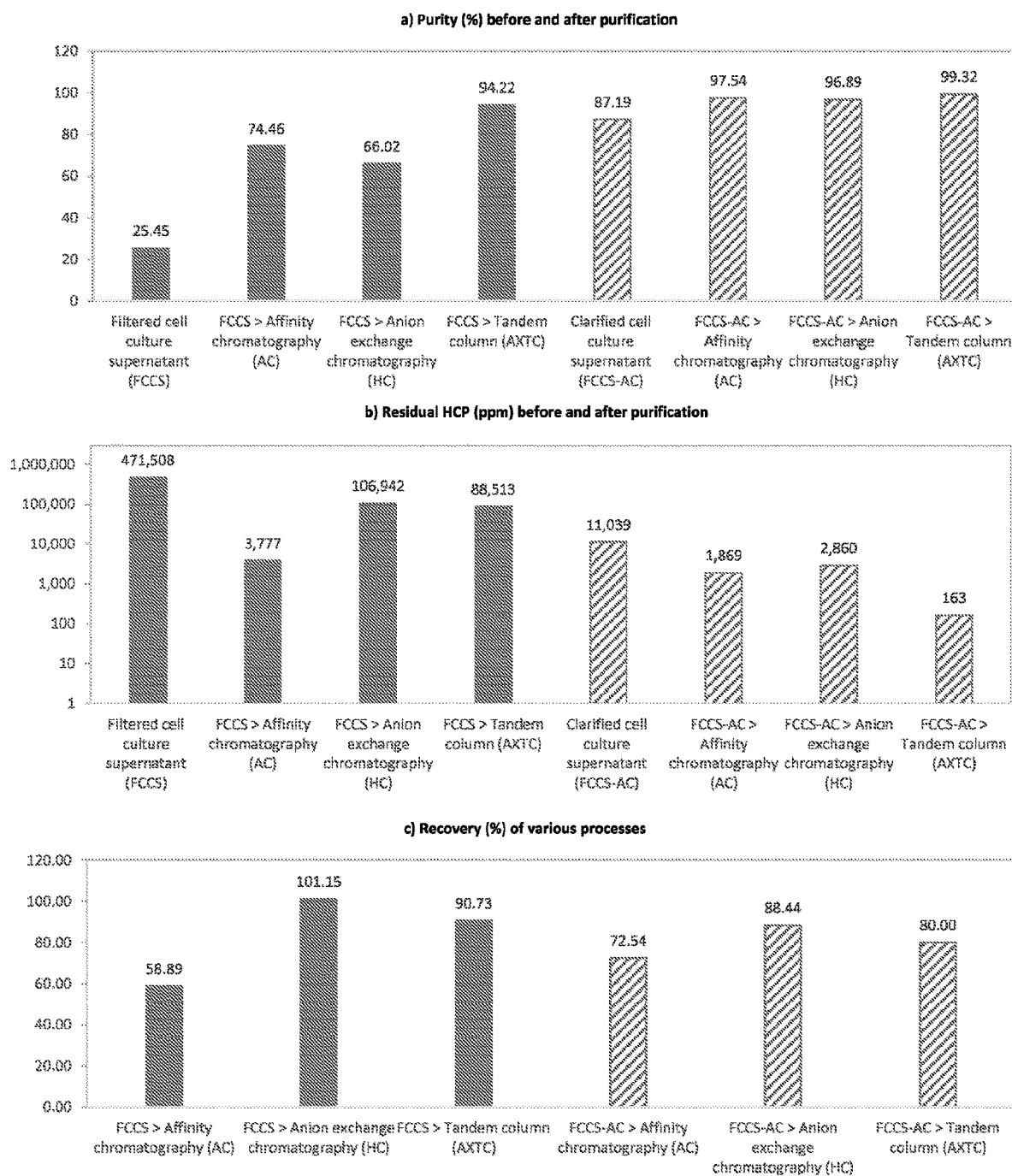
FIG. 19 shows the performance of tandem column configuration compared to other single-unit operations in terms of a) purity (%), b) residual HCP (ppm) and c) recovery (%) of various processes in one example.
Figure 20:
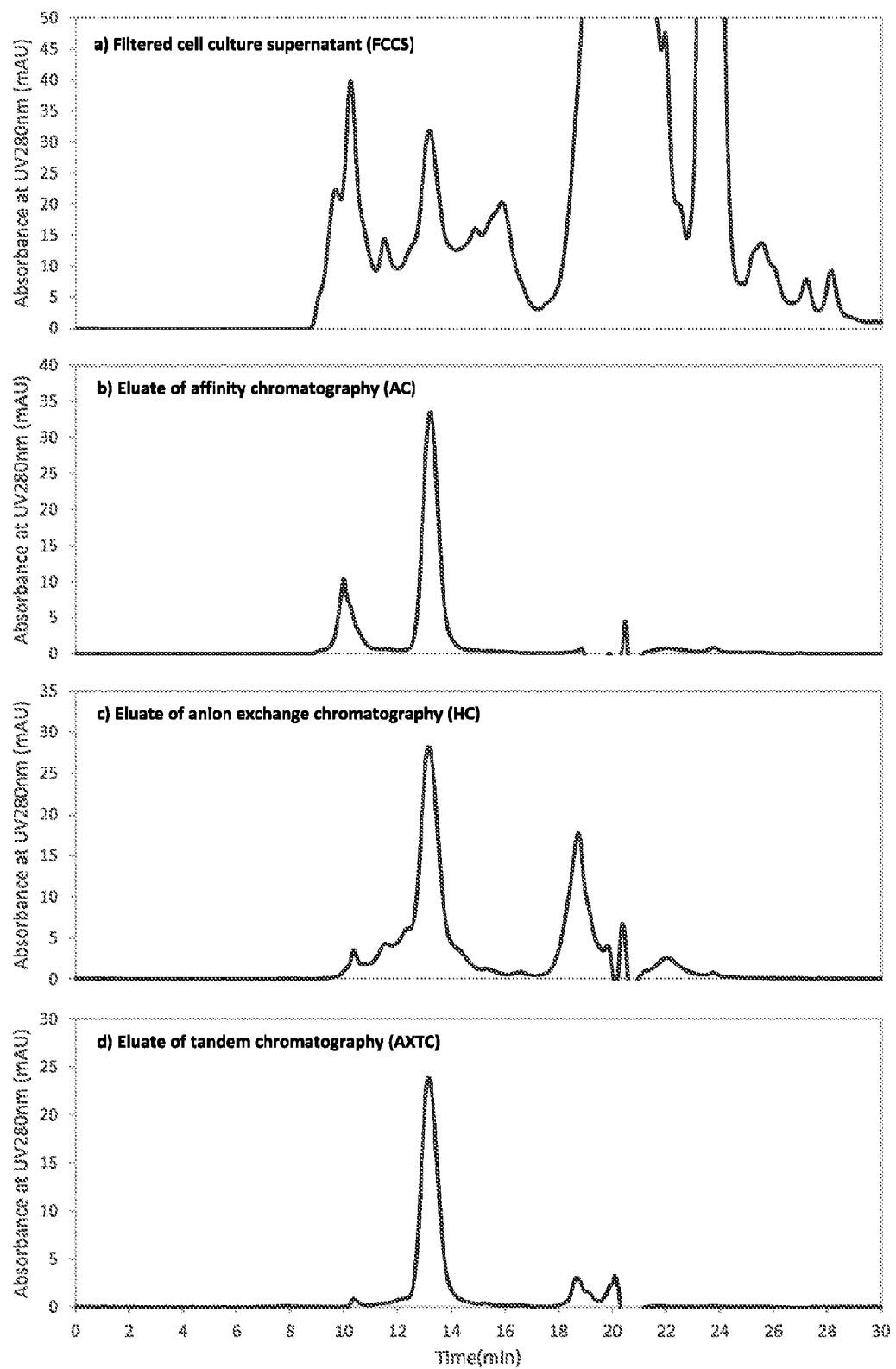
FIG. 20 shows the HPLC-SEC analysis results of a) filtered cell culture supernatant and eluate of b) affinity chromatography (AC), c) anion exchange chromatography (HC) and d) tandem chromatography (AXTC) in one example.
Figure 21:
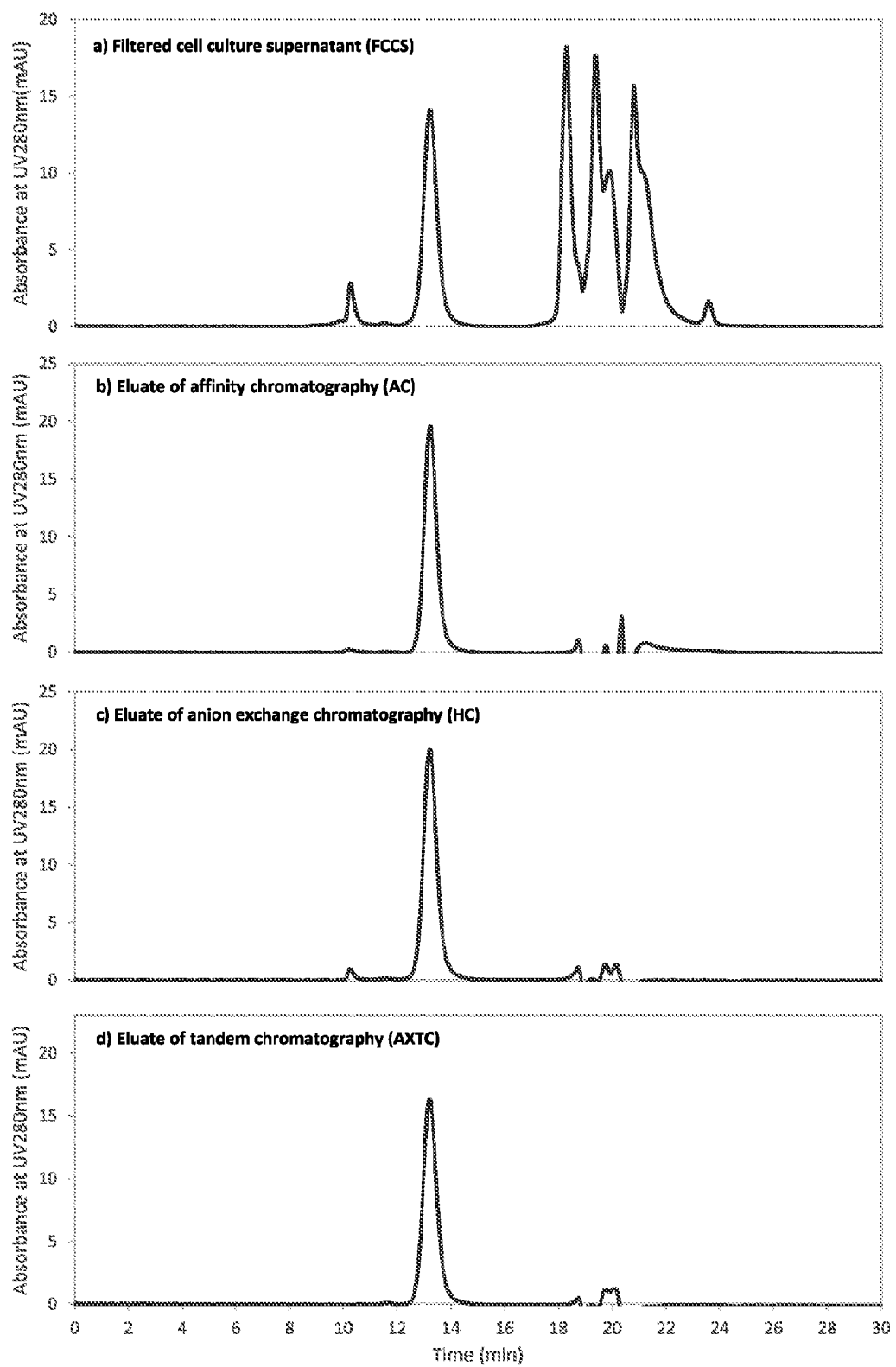
FIG. 21 shows the HPLC-SEC analysis results of a) clarified cell culture supernatant and eluate of b) affinity chromatography (AC), c) anion exchange chromatography (HC) and d) tandem chromatography (AXTC) in one example.

The results are shown in Table 22 below, and FIGS. 19 to 21.

TABLE 22

Purification table of various configuration of single unit operation using FCCS

| | A1AT Conc mg/ml | HMW % | Monomer % | LMW % | Vol ml | A1AT mg | Recovery % | HCP ppm | HPC removal Fold reduction |
|---|---|---|---|---|---|---|---|---|---|
| Filtered cell culture supernatant (FCCS) | 0.62 | 44.52 | 25.45 | 30.03 | | | | 471,508 | |
| Affinity chromatography (AC) | 1.96 | 23.88 | 74.46 | 1.66 | 2.42 | 4.74 | 58.9 | 3,777 | 124.85 |
| Anion exchange chromatography (HC) | 0.79 | 22.93 | 66.02 | 11.04 | 13.00 | 10.32 | 101.1 | 106,942 | 4.41 |
| Tandem column (AXTC) | 4.56 | 4.02 | 94.22 | 1.76 | 6.00 | 27.38 | 90.7 | 88,513 | 5.33 |

A1AT can be purified using affinity chromatography or anion exchange chromatography. Although affinity chromatography exhibits high selectivity with only 3,777 ppm of residual HCP, the percentage of HMW remains high at 23.88% as it is inefficient in removing aggregated proteins, resulting in a low A1AT purity of 74.46%. For anion exchange chromatography with low selectivity, A1AT purity in the eluate was only 66.02% and the residual HCP was only removed by 4.41 folds. However, with tandem column configuration, A1AT purity was shown to improve to 94.22% with a further reduction of residual HCP to 88,513 ppm. Therefore, tandem column configuration is a solution to anion exchanges with low selectivity and a potential replacement of affinity chromatography.

The performances of the different configurations were further compared using clarified FCCS-AC as a starting material. The experimental conditions employed are laid out in Table 23 below.

TABLE 23

Experimental conditions for different configuration of single unit operation using FCCS-AC

| Configuration | Valve: Name of column (size) | Experimental conditions | |
|---|---|---|---|
| Affinity chromatography (AC) using conventional batch mode | Column valve: Alpha-1 Antitrypsin Select (1.0 ml) | Equilibration buffer | 50 mM Tris pH 8.2 12.5 mS/cm (100 mM NaCl) |
| | | Flowrate | 0.3 ml/min |
| | | Sample | ~5 mg of clarified cell culture supernatant (FCCS-AC) at pH 8.2 12.5 mS/cm |
| Anion exchange chromatography (HC) using conventional batch mode | Column valve: HyperCel™ STAR AX (1.0 ml) | Equilibration buffer | 50 mM Tris pH 8.2 12.5 mS/cm (100 mM NaCl) |
| | | Elution buffer | 50 mM Tris pH 8.2 1M NaCl |
| | | Flowrate | 0.3 ml/min |
| | | Sample | ~9 mg of clarified cell culture supernatant |

TABLE 23-continued

Experimental conditions for different configuration of single unit operation using FCCS-AC

| Configuration | Valve: Name of column (size) | Experimental conditions | |
|---|---|---|---|
| Tandem column using anion exchange chromatography (AXTC) | Injection valve: TOYOPEARL NH2-750F (0.5 ml) Column valve: HyperCel™ STAR AX (1.0 ml) | Equilibration buffer<br>Elution buffer<br>Flowrate<br>Sample | (FCCS-AC) at pH 8.2 12.5 mS/cm<br>50 mM Tris pH 8.2 12.5 mS/cm (100 mM NaCl)<br>50 mM Tris pH 8.2 1M NaCl<br>0.3 ml/min<br>~14 mg of clarified cell culture supernatant (FCCS-AC) at pH 8.2 12.5 mS/cm |

The results are shown in Table 24 below, and FIGS. 19 to 21.

TABLE 24

Purification table of various configuration of single unit operation using FCCS-AC

| | A1AT Conc mg/ml | HMW % | Monomer % | LMW % | Vol ml | A1AT mg | Recovery % | HCP ppm | HPC removal Fold reduction |
|---|---|---|---|---|---|---|---|---|---|
| Clarified cell culture supernatant (FCCS-AC) | 0.79 | 12.81 | 87.19 | — | | | | 11,039 | |
| Affinity chromatography (AC) | 1.50 | 2.46 | 97.54 | — | 2.29 | 3.44 | 72.54 | 1,869 | 5.91 |
| Anion exchange chromatography (HC) | 2.71 | 3.11 | 96.89 | — | 3.00 | 8.14 | 88.44 | 2,860 | 3.86 |
| Tandem column (AXTC) | 4.54 | 0.68 | 99.32 | — | 2.45 | 11.11 | 80.00 | 163 | 67.70 |

When FCCS-AC was used as the starting material, tandem column performed the best in both aggregate and HCP removal. The final purified sample had a purity of 99.32% with only 163 ppm of residual HCP, which could not be achieved using other modes of single unit operation.

Given the same process duration, tandem chromatography has proven to achieve the highest aggregate removal as compared to other process methods. Within a single unit operation, the tandem configuration was able to achieve 94.22% purity using filtered cell culture supernatant or 99.32% using clarified cell culture supernatant.

The examples demonstrate the direct capture and purification of recombinant Alpha-1 antitrypsin (A1AT) in CHO cell culture in accordance with embodiments of the methods. A high salt tolerant anion exchanger TOYOPEARL NH2 750F was found to exhibit abnormal performance in that it could not bind A1AT readily even under favourable conditions. Hence, it was treated as pseudo flow-through mode and positioned as the first column in tandem chromatography to remove/pre-capture undesirable impurities or components in the cell culture supernatant such as CHO host cell protein, HCP, DNA and aggregates. To avoid installation of an additional column valve, TOYOPEARL NH2-750F is connected to injection valve while a second anion exchanger column (e.g. HyperCel™ STAR AX) or affinity column (e.g. Alpha-1 Antitrypsin Select) is connected to column valve located downstream. The intermediate product from first column was transported instantaneously to the second column (operating in bind & elute chromatography) in line whereby A1AT was captured either by an anion exchange chromatography or affinity chromatography. Subsequently, the first column was bypassed while the captured A1AT was dissociated from the second column by an elution buffer/ increasing the conductivity of buffer. Both columns can be regenerated under the same conditions. As a result, this process design led to an overall improvement of product purity and productivity in a single unit operation. In addition, the undesirable impurities or components did not bind to the second column, leaving more binding sites available for A1AT. Therefore, second column will have increased effective dynamic binding capacity of A1AT.

Example 1, 2 and 3 summarized the process design and optimization of tandem column chromatography while Example 4 explored on different potential combination of tandem column chromatography. This invention had proven to improve product purity significantly in a unit operation. For instance, using TOYOPEARL NH2 750F in series with HyperCel STAR AX, the monomer purity of A1AT had improved from 56.13% in filtered cell culture supernatant (FCCS) to 97.38% with a process recovery of 83.79% or 87.90% in clarified cell culture supernatant (FCCS-AC) to 99.66% with a process recovery of 83.64% (from Table 18). From comparative studies in Example 5 and 6, tandem column configuration was proved to improve the selectivity of anion exchange chromatography. the effective dynamic binding efficiency of HyperCel™ STAR AX was also demonstrated to increase from 11.67 mg to 32.08 mg of AAT per ml of resin. In addition, tandem column configuration has the capability to achieve better product quality within the same process duration and conditions. Using filtered cell culture supernatant with 25.45% purity, tandem chromatography could produce A1AT with 94.22% purity as compared to 66.02% in single anion exchangers (from table 22).

Traditionally, protein purification is operated in batch mode with a single column used in each unit operation and first chromatographic step is preferred to bind & elute chromatography. Disclosed herein is a new approach to process development while maintaining key purification principles using existing hardware. Hence, it is applicable to different FPLC systems with the potential to scale up to manufacturing process. Furthermore, an amalgamation of flow-through and bind & elute chromatography in tandem configuration has been proven herein to enhance purity and productivity in a single step purification. When applied in the capture step, embodiments of the method are able to achieve >90% purity from a starting material of less than 50% purity in a single unit operation. Embodiments of the method may also be applicable to other target proteins or other selection of chromatographic resins.

Embodiments of the method are expected to be particularly beneficial for purification of target proteins, including acidic proteins, which presently depend on costly affinity resin or target proteins for which affinity resin is not available and presently rely on low-resolution purification methods. Embodiments of the method are therefore applicable to a wide range of target proteins with various combinations of chromatographic resin.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

Applications

Embodiments of the method disclosed herein involve a tandem column configuration that can maximise process efficiency with improved productivity and product quality in single unit operation. Tandem column configuration can be achieved by connecting two columns in series without hardware modification, with first chromatography column installed at injection valve and second chromatography column installed at column valve. In the process condition whereby first column operated in flow-through chromatography and the second column operated in bind & elute chromatography, first column will remove impurities, to thereby allowing the second column to have more binding sites available for target protein (instead of impurities). As a result, embodiments of the method employing tandem chromatography are able to improve overall/enhance the selectivity, binding efficiency and productivity in a single step purification process.

Typically, an anion exchanger binds to any molecules with negative net surface charge, and thus, the process is not specific to any target proteins. Advantageously, embodiments of the method are able to improve the overall selectivity and binding efficiency of an anion exchanger. By connecting two anion exchanger columns in series, through direct capture and purification, embodiments of the method are demonstrated able to purify the acidic recombinant protein A1AT from a cell culture supernatant at high recovery and purity.

Embodiments of the method can advantageously capture target proteins with no or minimal dilution. Embodiments of the method using high salt tolerant anion exchanger can be advantageously applied to supernatant with conductivity greater than 10 mS/cm which is challenging for conventional anion exchanger that requires conductivity to be lower than 5 mS/cm.

Further, embodiments of the method use scalable chromatographic resin that allows the method to be applicable in the manufacturing scale.

In particular, embodiments of the method have demonstrated a capability to resolve current challenges faced in production of A1AT, such as low resolving capability of ion exchange in capture step, a small operating window use of conventional anion exchange as the ionic strength of binding buffer and sample has to be less than 5 mS/cm and costly affinity chromatography with high selectivity but low binding capacity.

The invention claimed is:

1. A chromatography system consisting of two valves, wherein:
   a first valve is in fluid connection to a first chromatography column and/or a second valve;
   the second valve is in fluid connection to a second chromatography column and the first valve;
   wherein the first valve and the second valve are operable to provide:
   i) a mode A that selectively allows a fluid to flow from the first chromatography column to the second chromatography column;
   ii) a mode B that selectively allows the fluid to bypass the first chromatography column; and/or
   iii) a mode C that selectively allows the fluid to bypass the second chromatography column,
   wherein the first valve is positioned parallel to the first chromatography column; and
   wherein the first valve is an injection valve, optionally the second valve is a column valve.

2. The system of claim 1, wherein the first valve in fluid connection to the first chromatography column and the second valve in fluid connection to the second chromatography column are in tandem arrangement.

3. The system of claim 1, wherein the first valve is operable to selectively allow fluid flow
   to flow through the first chromatography column; or
   to bypass the first chromatography column,
   optionally wherein an outlet of the first valve is linked to an inlet of the second valve;
   optionally wherein the second valve is operable to selectively allow fluid flow to flow through the second chromatography column or to bypass the second chromatography;
   optionally wherein:
   i) in the mode A, the first valve directs the fluid to flow from the first chromatography column connected to the first valve to the second chromatography column connected to the second valve;
   ii) in the mode B, wherein the first valve directs the fluid to bypass the first chromatography column, thereby directing the fluid to flow from the first valve to the second chromatography column connected to the second valve; and
   iii) in the mode C, wherein the first valve directs the fluid to flow through the first chromatography column connected to the first valve to the second valve that directs the solution to bypass the second chromatography column.

4. The system of claim 1, wherein the first chromatography column is a flow-through chromatography column or a bind & elute chromatography column and the second chromatography column is a flow-through chromatography column or a bind & elute chromatography column.

5. The system of claim 1, wherein the first chromatography column is a flow-through chromatography column and the second chromatography column is a bind & elute chromatography column, optionally wherein the system directs fluid to flow in mode A and in mode B, sequentially.

6. The system of claim 1, wherein the second valve is a column valve,
optionally wherein the first chromatography column is a bind & elute chromatography column and the second chromatography column is a flow-through chromatography column,
optionally wherein the system directs fluid to flow in mode C and in mode A, sequentially,
optionally wherein the first chromatography column is a bind & elute chromatography column and the second chromatography column is a bind & elute chromatography column,
optionally wherein the system directs fluid to flow in mode C, in mode A and in mode B, sequentially.

7. The system of claim 1, wherein the first chromatography column and/or the second chromatography column is an affinity or non-affinity chromatography, or
wherein the first chromatography column and/or the second chromatography column is an anion exchange chromatography,
optionally wherein the first chromatography column is a high salt tolerant anion exchanger and/or the second chromatography column is a conventional anion exchange chromatography, high salt tolerant anion exchange chromatography and/or an affinity chromatography.

8. The system of claim 1, wherein the first chromatography column is a high salt tolerant anion exchanger, optionally the second chromatography column is a bind & elute chromatography column selected from the group consisting of a conventional anion exchanger, a high salt tolerant anion exchanger, and an affinity chromatography,
optionally wherein the first chromatography column is a high salt tolerant anion exchanger and the second chromatography column is selected from the group consisting of a conventional anion exchanger, a high salt tolerant anion exchanger, and an affinity chromatography.

9. A method of purifying a target from sample, comprising:
a) providing a system according to claim 1, and
b) collecting the target from the system.

10. The method of claim 9, wherein the first chromatography column is a flow-through chromatography column or a bind & elute chromatography column and the second chromatography column is a flow-through chromatography column or a bind & elute chromatography column,
optionally wherein the first chromatography column is a flow-through chromatography column and the second chromatography column is a bind & elute chromatography column,
optionally wherein when the system directs fluid to flow in mode A and in mode B, sequentially, the target is collected in mode B by disassociating the target from the second chromatography column.

11. The method of claim 9, wherein the first chromatography column is a bind & elute chromatography column and the second chromatography column is a flow-through chromatography column,
optionally wherein when the system directs fluid to flow in mode C and in mode A, sequentially, the target is collected in mode A by dissociating target from the first chromatography column and flow through the second chromatography column, or
wherein the first chromatography column is a bind & elute chromatography column and the second chromatography column is a bind & elute chromatography column,
optionally wherein when the system directs fluid to flow in mode C, in mode A and in mode B, sequentially, the target is collected in mode B by disassociating the target from the second chromatography column.

12. The method of claim 9, wherein the target is a target protein, optionally an acidic protein.

13. The method of claim 9, wherein the target is a recombinant acidic protein, optionally an alpha-1 antitrypsin (A1AT).

14. The system of claim 1, wherein the purification is 90%, or 91%, or 92%, or 93%, or 94% or 95%, or 96%, 97%, 98%, or 99% pure.

15. The method of claim 9, wherein the sample is a supernatant (such as cell culture supernatant).

16. The method of claim 9, wherein the first valve, the second valve, the first chromatography column and the second chromatography column are integrated in a single closed- and self-contained apparatus.

17. The method of claim 9, wherein the purification is 90%, or 91%, or 92%, or 93%, or 94% or 95%, or 96%, 97%, 98%, or 99% pure.

18. The system of claim 1, wherein the first valve, the second valve, the first chromatography column and the second chromatography column are integrated in a single closed- and self-contained apparatus.

* * * * *